US012161523B2

(12) United States Patent
Christensen et al.

(10) Patent No.: US 12,161,523 B2
(45) Date of Patent: Dec. 10, 2024

(54) HARDENABLE DENTAL COMPOSITIONS COMPRISING BASIC CORE MATERIAL ENCAPSULATED IN AN INORGANIC SHELL AND DISPENSING DEVICES THEREWITH

(71) Applicant: Solventum Intellectual Properties Company, Maplewood, MN (US)

(72) Inventors: Randilynn B. Christensen, Pine Springs, MN (US); Kenton D. Budd, Woodbury, MN (US); Afshin Falsafi, Woodbury, MN (US); Mahmut Aksit, Woodbury, MN (US); Jana Ninkovic, St. Paul, MN (US); Jie J. Liu, Cottage Grove, MN (US); Mark B. Agre, Rochester, MN (US); Masayuki Nakamura, Woodbury, MN (US); Jason W. Bjork, Cottage Grove, MN (US); Bradley D. Craig, Lake Elmo, MN (US); Richard P. Rusin, Woodbury, MN (US); Paul J. Homnick, Lake Elmo, MN (US); Joel D. Oxman, Minneapolis, MN (US); Yizhong Wang, Woodbury, MN (US); Paul R. Klaiber, Mahtomedi, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 948 days.

(21) Appl. No.: 15/734,357

(22) PCT Filed: Jun. 5, 2019

(86) PCT No.: PCT/IB2019/054690

§ 371 (c)(1),
(2) Date: Dec. 2, 2020

(87) PCT Pub. No.: WO2019/234661

PCT Pub. Date: Dec. 12, 2019

(65) Prior Publication Data

US 2021/0228315 A1 Jul. 29, 2021

Related U.S. Application Data

(60) Provisional application No. 62/681,558, filed on Jun. 6, 2018.

(51) Int. Cl.
*A61C 5/64* (2017.01)
*A61C 5/68* (2017.01)
(Continued)

(52) U.S. Cl.
CPC .................. *A61C 5/64* (2017.02); *A61C 5/68* (2017.02); *A61K 6/17* (2020.01); *A61K 6/61* (2020.01);
(Continued)

(58) Field of Classification Search
CPC ............. A61C 5/64; A61C 5/68; C08L 33/08; C08L 33/10; A61K 6/849–882; A61K 6/889; C08K 9/10
See application file for complete search history.

(56) References Cited

U.S. PATENT DOCUMENTS

| | | |
|---|---|---|
| 3,066,112 A | 11/1962 | Bowen |
| 3,729,313 A | 4/1973 | Smith |

(Continued)

FOREIGN PATENT DOCUMENTS

| | | |
|---|---|---|
| GB | 1534261 | 11/1978 |
| JP | H03-267067 | 11/1991 |

(Continued)

OTHER PUBLICATIONS

A Guide to Silane Solutions—Mineral and Filler Treatment, Dow Corning Corporation, 2009, 3 pages.

(Continued)

*Primary Examiner* — Kregg T Brooks
*Assistant Examiner* — David R. Foss

(57) ABSTRACT

A hardenable (e.g. dental) compositions is described comprising an encapsulated material. The encapsulated material comprises a basic core material and an inorganic shell material having certain viscosity criteria. Also described are dispensing devices and kits are described comprising a hardenable (e.g. dental) composition comprising a liquid material and an encapsulated material wherein the encapsulated material comprises a basic core material and an inorganic shell material comprising a metal oxide surrounding the core. The dispensing devices and kits can facilitate the
(Continued)

methods of applying the hardenable composition. The hardenable or hardened (e.g. cured) composition can provide various technical effects such as a delayed release of a basic core material, a delayed increase in basicity, promoting remineralization of a tooth or bone structure, and increasing the average alkaline phosphatase (ALP) activity of pulp cells. In some embodiments, the composition is a dental (e.g. sealant) composition for application to a tooth structure.

20 Claims, 3 Drawing Sheets

(51) Int. Cl.

| | |
|---|---|
| ***A61K 6/17*** | (2020.01) |
| ***A61K 6/61*** | (2020.01) |
| ***A61K 6/62*** | (2020.01) |
| ***A61K 6/71*** | (2020.01) |
| ***A61K 6/818*** | (2020.01) |
| ***A61K 6/851*** | (2020.01) |
| ***A61K 6/853*** | (2020.01) |
| ***A61K 6/876*** | (2020.01) |
| ***A61K 6/887*** | (2020.01) |
| ***C08K 9/10*** | (2006.01) |
| *A61K 6/889* | (2020.01) |
| *C08L 33/10* | (2006.01) |

(52) U.S. Cl.

CPC .................. *A61K 6/62* (2020.01); *A61K 6/71* (2020.01); *A61K 6/818* (2020.01); *A61K 6/851* (2020.01); *A61K 6/853* (2020.01); *A61K 6/876* (2020.01); *A61K 6/887* (2020.01); *A61K 6/889* (2020.01); *C08K 9/10* (2013.01); *C08L 33/10* (2013.01)

(56) References Cited

U.S. PATENT DOCUMENTS

| | | | | |
|---|---|---|---|---|
| 4,150,012 | A | 4/1979 | Joos | |
| 4,209,434 | A | 6/1980 | Wilson | |
| 4,503,169 | A | 3/1985 | Randklev | |
| 4,632,672 | A | 12/1986 | Kvitrud | |
| 4,871,786 | A | 10/1989 | Aasen | |
| 5,100,320 | A | 3/1992 | Martin | |
| 5,130,347 | A | 7/1992 | Mitra | |
| 5,149,368 | A | 9/1992 | Liu | |
| 5,154,762 | A | 10/1992 | Mitra | |
| 5,156,885 | A | 10/1992 | Budd | |
| 5,332,429 | A | 7/1994 | Mitra | |
| 5,545,676 | A | 8/1996 | Palazzotto | |
| 5,848,894 | A | 12/1998 | Rogers | |
| 6,030,606 | A | 2/2000 | Holmes | |
| 6,387,981 | B1 | 5/2002 | Zhang | |
| 6,444,725 | B1 | 9/2002 | Trom | |
| 6,444,726 | B1 | 9/2002 | Brunt | |
| 6,572,693 | B1 | 6/2003 | Wu | |
| 6,613,383 | B1 | 9/2003 | George | |
| 6,685,966 | B1 | 2/2004 | Dominique | |
| 6,730,156 | B1 | 5/2004 | Windisch | |
| 7,036,944 | B2 | 5/2006 | Budd | |
| 7,090,721 | B2 | 8/2006 | Craig | |
| 7,090,722 | B2 | 8/2006 | Budd | |
| 7,156,911 | B2 | 1/2007 | Kangas | |
| 7,241,437 | B2 | 7/2007 | Davidson | |
| 7,396,862 | B2 | 7/2008 | Weimer | |
| 7,649,029 | B2 | 1/2010 | Kolb | |
| 8,236,871 | B2 | 8/2012 | Hecht | |
| 8,414,930 | B2 | 4/2013 | Liu | |
| 8,449,904 | B1 | 5/2013 | Jung | |
| 8,455,554 | B2 | 6/2013 | Kessler | |
| 8,647,510 | B2 | 2/2014 | Kolb | |
| 8,722,759 | B2 | 5/2014 | Craig | |
| 9,193,849 | B2 | 11/2015 | Stelzig | |
| 9,427,290 | B2 | 8/2016 | Boehm | |
| 2003/0195273 | A1 | 10/2003 | Mitra | |
| 2004/0224087 | A1 | 11/2004 | Weimer | |
| 2005/0252413 | A1 | 11/2005 | Kangas | |
| 2006/0051427 | A1 | 3/2006 | Talton | |
| 2007/0183984 | A1 | 8/2007 | Haas | |
| 2008/0058442 | A1 | 3/2008 | Hermansson | |
| 2008/0152598 | A1 | 6/2008 | Basic | |
| 2009/0227700 | A1* | 9/2009 | Uchida | A61K 6/887 522/76 |
| 2010/0272764 | A1 | 10/2010 | Latta | |
| 2011/0129794 | A1* | 6/2011 | Pauser | A61C 5/62 433/90 |
| 2011/0213036 | A1 | 9/2011 | Park | |
| 2012/0295214 | A1 | 11/2012 | Wang | |
| 2015/0013568 | A1 | 1/2015 | Lim | |
| 2015/0272834 | A1 | 10/2015 | Sun | |
| 2015/0291778 | A1 | 10/2015 | Musick | |
| 2016/0270879 | A1 | 9/2016 | Boehm | |
| 2017/0063829 | A1 | 3/2017 | Raounak | |
| 2017/0216152 | A1 | 8/2017 | Hecht | |

FOREIGN PATENT DOCUMENTS

| | | |
|---|---|---|
| RU | 2429814 | 9/2011 |
| WO | WO 1997-035916 | 10/1997 |
| WO | WO 2001-030304 | 5/2001 |
| WO | WO 2001-030305 | 5/2001 |
| WO | WO 2001-030307 | 5/2001 |
| WO | WO 2003-063804 | 8/2003 |
| WO | WO 2005-039508 | 5/2005 |
| WO | WO 2015-187490 | 12/2015 |
| WO | WO 2016-005822 | 1/2016 |
| WO | WO 2016-205181 | 12/2016 |
| WO | WO 2017-180545 | 10/2017 |
| WO | WO 2018-057503 | 3/2018 |
| WO | WO 2018-102484 | 6/2018 |
| WO | WO 2019-234633 | 12/2019 |

OTHER PUBLICATIONS

Adamson, "S 32. Aminoalkyl Tertiary Carbinols And Derived Products. Part I. 3-Amino-1: 1-Diphenylpropan-1-ols", Journal of the Chemical Society, 1949, Part 1, pp. S144-S155.

Ana, "Effects of Added Bioactive Glass on the Setting and Mechanical Properties of Resin-Modified Glass Ionomer Cement", Biomaterials, Aug. 2003, vol. 24, No. 18, pp. 3061-3067.

Arkles, "Silane Coupling Agents: Connecting Across Boundaries," v2.0, Gelest Inc., 2006, 12 pages.

Baechle, "Fluidized Bed Sputtering for Particle and Powder Metallization", Army Research Laboratory, Apr. 2013, ARL-TR-6435, pp. 1-34.

Hirano, "Treatment of Inorganic Filler Surface by Silane-Coupling Agent: Investigation of Treatment Condition and Analysis of Bonding State of Reacted Agent", International Journal of Chemical, Molecular, Nuclear, Materials and Metallurgical Engineering, Jan. 2012, vol. 6, No. 1, pp. 1-5.

Mishra, Handbook of Encapsulation and Controlled Release (2015), 329-344.

Nasanova, "Multifunctional Particle Coating by Plasma Process and Its Application to Pollution Control", RSC Advances, Jun. 2014, vol. 4, No. 56, pp. 29866-29876.

Sarkar, "A Modified Portland Cement for Dental Use: Its Interaction with Simulated Oral Environment", Transactions of the Indian Ceramic Society, Nov. 2014, vol. 4, No. 56, pp. 200-204.

Sulzer, "MIXPAC™ the Diversity of our Dental Applications", 24 pages.

International Search Report for PCT International Application No. PCT/US2017/063829, mailed on Mar. 15, 2018, 5 pages.

International Search Report for PCT International Application No. PCT/IB2019/054644, mailed on Sep. 17, 2019, 6 pages.

(56) References Cited

OTHER PUBLICATIONS

International Search Report for PCT International Application No. PCT/IB2019/054690, mailed on Oct. 21, 2019, 5 pages.

* cited by examiner

HARDENABLE DENTAL COMPOSITIONS COMPRISING BASIC CORE MATERIAL ENCAPSULATED IN AN INORGANIC SHELL AND DISPENSING DEVICES THEREWITH

CROSS REFERENCE TO RELATED APPLICATIONS

This application is a national stage filing under 35 U.S.C. 371 of PCT/IB2019/054690, filed 5 Jun. 2019, which claims the benefit of U.S. Provisional Application No. 62/681,558, filed 6 Jun. 2018, the disclosures of which are incorporated by reference in their entireties herein.

BACKGROUND

Various cements suitable for use for medical and dental have been described. See for example Mitra et al. U.S. Pat. No. 5,154,762; WO 2016/005822; and US2008/0058442.

SUMMARY

Figure 1:
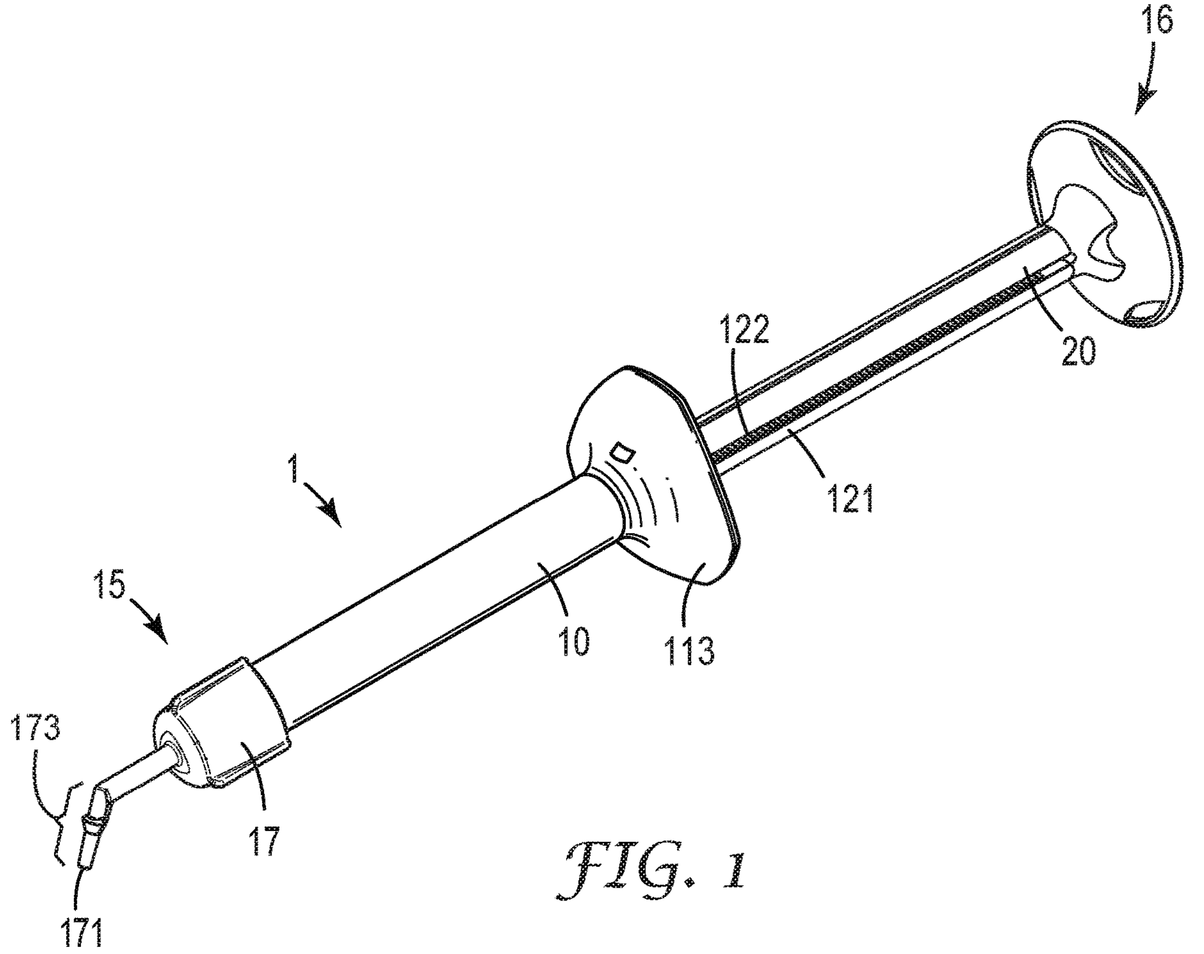
FIG. 1 is a perspective view of an illustrative syringe.

In some embodiments, hardenable (e.g. dental) compositions are described comprising an encapsulated material. The encapsulated material comprises a basic core material and an inorganic shell material comprising a metal oxide surrounding the core.

In some embodiments, the described hardenable (e.g. dental) compositions have certain viscosity criteria.

In one embodiment, a two part hardenable composition is described comprising a first part comprising a composition comprising a liquid material and an encapsulated material wherein the encapsulated material comprises a basic core material and an inorganic shell material comprising a metal oxide surrounding the core; and a second part comprising a composition comprising a liquid material. The composition of the first part has a first viscosity, the composition of the second part has a second viscosity; and the first and second viscosity are the same or have a difference that is no greater than 85, 80, 75, 70, 65, 60, 55, 50, 45, 40, 35, 30, 25, 20, 15, or 10% of the higher viscosity part.

In another embodiment, a two part hardenable composition is described comprising a first part comprising a composition having a viscosity is no greater than 6500 cps comprising a liquid material and an encapsulated material wherein the encapsulated material comprises a basic core material and an inorganic shell material comprising a metal oxide surrounding the core; and a second part comprising a composition having a viscosity no greater than 6500 cps comprising a liquid material.

In another embodiment, the hardenable composition is described comprising a one part composition comprising a liquid material and an encapsulated material wherein the encapsulated material comprises a basic core material and an inorganic shell material comprising a metal oxide surrounding the core; wherein the one part composition has a viscosity of less than 25,000 cps as determined with a Brookfield viscometer and type-A T-bar spindle at 23° C. and shear rate of 100 $s^{-1}$ or the one part composition has a viscosity greater than 40,000 cps.

The viscosity of the (e.g. lower viscosity) hardenable compositions may be determined with a Brookfield viscometer and type-A T-bar spindle at 23° C. and shear rate of 100 $s^{-1}$. In some embodiments, the viscosity criteria is amenable to the end use of the hardenable (e.g. dental) compositions and/or dispensing devices for such compositions and/or methods of applying such compositions.

In other embodiments, two part hardenable (e.g. dental) compositions are described comprising a redox curing system.

In one embodiment, a hardenable composition is described comprising a first part comprising an encapsulated material wherein the encapsulated material comprises a basic core material and an inorganic shell material comprising a metal oxide surrounding the core; a non-aqueous second part; and a redox curing system. The second part may comprise a (e.g. liquid) polymerizable resin.

In another embodiment, a hardenable composition is described comprising a first part comprising an encapsulated material wherein the encapsulated material comprises a basic core material and an inorganic shell material comprising a metal oxide surrounding the core and a reducing agent; and a second part comprising an oxidizing agent selected from peroxide compounds, persulfate compounds, perborate compounds, and perchlorate compounds.

In other embodiments, dispensing devices and kits are described comprising a hardenable (e.g. dental) composition comprising a liquid material and an encapsulated material wherein the encapsulated material comprises a basic core material and an inorganic shell material comprising a metal oxide surrounding the core. The dispensing devices and kits can facilitate the methods of applying the hardenable composition.

In some embodiments, the hardenable or hardened composition contacts water, an acidic component, or a biological fluid during use.

In typical embodiment, upon combining the first and second part, the composition initially has an acidic or neutral pH. The shell is degradable by water or the acidic component of the second part. The basic core material releases —OH upon degradation of the shell, thereby increasing the pH.

In some embodiments, the basic core material is hardenable, such as in the case of calcium silicate. In some embodiments, the composition further comprises at least one second filler, such as fluoroaluminosilicate (FAS) glass and/or a nanoscopic particulate filler. In some embodiments, the first and/or second part comprises a polymerizable (e.g. liquid) material.

Also described are various methods of use that comprise providing the hardenable or hardened (e.g. cured) composition as described herein and applying the composition to a tooth or bone structure.

In some embodiments, the composition comprises a polymerizable material and the method further comprises hardening by exposing the composition to a radiation source and/or by use of a redox curing system. The hardenable or hardened (e.g. cured) composition can provide various technical effects such as a delayed release of a basic core material, a delayed increase in basicity, promoting remineralization of a tooth or bone structure, and increasing the average alkaline phosphatase (ALP) activity of pulp cells. In some embodiments, the composition is a dental (e.g. sealant) composition for application to a tooth structure. In other embodiments, the composition is a dental restorative.

DETAILED DESCRIPTION

Presently described are encapsulated materials. The encapsulated materials are suitable for use in a biological carrier material, such as a hardenable dental composition. The encapsulated material comprises a chemically basic core material and an inorganic shell material surrounding the core. The shell material and thickness of the shell can be selected to permit controlled and/or delayed release or reaction of the basic core material. In some embodiments, the release of the basic core material is utilized for increasing basicity after an extended period of time.

The encapsulated filler comprises a basic core material. The basic core material, as well as the materials (e.g. compounds) from which the core is formed, are generally solid at 25° C.

The basic core can be a single particle or a plurality of smaller associated particles. As used herein, the term "associated" refers to a grouping of two or more primary particles that are aggregated and/or agglomerated. Similarly, the term "non-associated" refers to groupings of two or more primary particles that are free from aggregation and/or agglomeration.

In some embodiments, the basic core may comprise a plurality of aggregated particles. "Aggregation" or "aggregated" refers to a strong association between primary particles. For example, the primary particles may be chemically bound to one another. The breakdown of aggregates into smaller particles (e.g., primary particles) is typically not achieved during fabrication of the core material and encapsulation thereof such that the aggregated core particles remain as aggregates. Similarly, the term "non-aggregated" refers to primary particles that are free of strong associations with other primary particles.

In other embodiments, the basic core may comprise a plurality of agglomerated particles. As used herein, the term "agglomeration" or "agglomerated" refers to a weak association of primary particles. For example, the primary particles may be held together by charge or polarity. The breakdown of agglomerates into smaller particles (e.g., primary particles) can occur during fabrication of the core material and encapsulated thereof. Similarly, the term "non-agglomerated" refers to primary particles that are free of weak associations with other primary particles.

The average (e.g. primary, associated, or agglomerated) particle size of the core is typically at least 0.2, 0.5, 1, 2, 3, 4, or 5 micrometers and typically no greater than 1 mm, 750 micrometers, or 500 micrometers, as measured using, for example, a sedimentation analyzer. In some embodiments, such as in the case of hardenable dental compositions, the basic core material typically has an average (e.g. primary, associated, or agglomerated) particle size of no greater than 250, 200, 150, 100 or 50 micrometers. In some embodiments, the basic (e.g. core) material typically has an average (e.g. primary, associated, or agglomerated) particle size of no greater than 45, 40, 35, 30, 25, or 20 micrometers. Since the shell is typically thin, the encapsulated material can also fall within the average particle sizes just described.

The core material is basic. Chemically basic materials are materials that donate electrons, accept protons and typically provide hydroxyl ions in aqueous solution.

Cores of the encapsulated material are considered to be basic if they possess or exhibit one or more characteristics described below including comprising a sufficient amount of a high pKa component, providing a basic pH when added to deionized water (according to the test method further described in the examples), or providing a basic pH when added to an acidic buffer (according to the test method further described in the examples).

Basic materials function to react with acids and acidic buffer solutions producing an increase in pH. The change in pH, and the rate of pH change depend on the strength of the basic components, the chemical and physical form of the basic components therein, and the amount of the basic components within the core material.

In some embodiments, the core of the encapsulated material is strongly basic. Strongly basic materials comprise and are prepared from a sufficient amount of a strongly basic material (e.g. compound), typically having a pKa in the range of about 11-14. Examples of strongly basic compounds include oxides and hydroxides of alkali and alkaline earth metals, as well as strongly basic salts, such as alkali phosphates. Specific examples of strongly basic core compounds include oxides and hydroxides of Na, K, Ca, Sr, and Ba; silicates of Na, K, Ca, Sr, and Ba; and aluminates of Na, K, Ca, Sr, and Ba. Strongly basic silicates and glasses typically comprise at least 1, 2, or 3 moles of strongly basic core compound (e.g. CaO) per mole of silica on a cation molar basis. Likewise, strongly basic aluminate typically comprise at least 1, 2, or 3 moles of strongly basic core compound (e.g. CaO) per mole of alumina on a cation molar basis.

In some embodiments, the strongly basic material can be a heterogenous physical mixture of at least one strongly basic compound in combination with less basic or neutral materials. For example, the strongly basic material may be a physical mixture of silica and sodium hydroxide. Sodium hydroxide is a strongly basic material, having a pKa of 13.8. A 0.1 N aqueous solution of sodium hydroxide has a pH of 13. On a weight percent basis, one gram of a mixture of 96 wt.-% silica and 4% wt.-% sodium hydroxide in a liter of water would provide a 0.1 N aqueous solution of sodium hydroxide. When the encapsulated material is a physical mixture, substantially all the strongly basic compound is accessible upon degradation of the shell. Thus, in this embodiment, the basic core material may comprise a small amount (e.g. at least 1, 2, or 3 wt.-% of a strongly basic material in order to provide a delayed pH of at least 8.5 or 9 in deioinized water (according to the test method described in the examples). However, a higher concentration of chemically basic core material may be needed to provide a delayed pH of at least 8.5 or 9 in an acid buffer solution. For example, depending on the pKa of the strongly basic material, the amount of strongly basic material, may be at least 5, 6, 7, 8, 9, or 10 wt.-% of the total encapsulated material.

In other embodiments, the core of the encapsulated material is a multicomponent crystalline compound that comprises and is prepared from at least one strongly basic material (e.g. compound) and other components (such as alkaline earth silicates). In yet other embodiments, the core of encapsulated material can be characterized as a multi-component amorphous glass prepared from at least one strongly basic material (e.g. compound). The strongly basic material (e.g. compound) can be distributed homogeneously or nonhomogeneously in the glass structure. When the core of the encapsulated material is a fused multicomponent material such as glass, the concentration of strongly basic compound (as can be determined by X-ray fluorescence (XRF) or inductively coupled plasms (ICP)) is typically at least 25, 30, 35, 40, 45, or 50 wt.-% ranging up to 75 wt.-% or greater based on the total basic core material.

In some favored embodiments, the core comprises and is prepared from CaO, having a pKa of 11.6. CaO can be utilized to provide both a delayed increase in pH in combination with providing a source of calcium ions. The amount of CaO is typically at least 5, 10, 15, 20, or 25 wt.-% and can range up to 75 wt.-% or greater. The amount of Ca is about 71% of such values.

Specific examples of strongly basic multicomponent core materials comprising CaO include Portland cements (reported to contain 60-70% wt.-% CaO); tricalcium silicate (containing about 75 wt.-% CaO); and bioactive glass, as can be obtained from 3M Advanced Material Division (containing from about 25 wt.-% of CaO, and about 25 wt.-% of $Na_2O$).

In other embodiments, the core of the encapsulated material is weakly basic. Weakly basic materials comprise a substantial amount of at least one material (e.g. compound) having a pKa in the range of at least 8, but less than 11. Examples of weakly basic core compounds include oxides of Cu, Zn, and Fe as well as and weakly basic salts, such as NaF, Ca acetate, and hydrogen phosphates.

Alternatively, a weakly basic core material may comprise or be prepared from a smaller amount of a strongly basic compound. A weakly basic core material alone cannot typically provide a sufficient amount of hydroxyl ion to adequately increase the pH of an acidic solution. However, a weakly basic core material alone may provide a sufficient amount of hydroxyl ion to adequately increase the pH of water. Further, encapsulated weakly basic core materials can be used in combination with encapsulated strongly basic core materials.

The encapsulated basic material is typically not a reducing agent of a redox curing system. In some favored hardenable (e.g. dental or medical) materials, a favored technical effect is to control the pH such that the composition is initially acidic for a sufficient amount of time to promote adhesion and then subsequently becomes basic to promote remineralization. This change in pH is sufficiently delayed such that it occurs after curing. Encapsulation of a reducing agent would delay the redox curing reaction. Further, since reducing agents are typically weak bases utilized in relatively small concentrations, encapsulating reducing agent alone would not provide the desired increase in pH.

In favored embodiments, the core material further comprises and is prepared from one or more neutral compounds, defined herein as having a pKa of at least 6, 6.5 or 7, and less than 8. In some embodiments, such neutral compounds exhibit low solubility in deionized water, and/or a weak acid solution, and/or a weak base solution. Weak acid solutions typically have a pH of less than 7, but greater than 4. Weak base solutions typically have a pH of greater than 7, but less than 10. By low solubility, it is meant that less than 100 grams per liter (i.e. 10 wt.-%) dissolve. In some embodiments, less than 50, 25, 5, or 1 gram dissolves per liter. Neutral compounds include for example silica, zirconia, titania, alumina, and combinations thereof. Although a pKa greater than 7 is slightly basic, such basicity is less than that of weakly basic core materials and significantly less than that of strongly basic core materials, as previously described.

When the core material comprises and is prepared solely from basic materials (e.g. compound(s) or a combination of basic materials with neutral materials, the basicity of the core material can be estimated based on the weight of the components). Thus, the core material comprises the amount of basic material (e.g. compound) as previously described.

However, when the core material further comprises acidic materials (e.g. compounds) it can be more difficult to estimate the basicity. Particularly for embodiments wherein it is difficult to estimate the basicity of a core material based on its composition or compositional analysis, the basicity of the core material or encapsulated core material can be defined by a change in pH of a specified amount of material in deionized water or in an acidic (e.g. buffer) solution. These tests can also be used to verify that a core material or encapsulated core material is in fact basic.

For example, fluoroaluminosilicate (FAS) glass is a homogeneous glass structure prepared from about 19 wt.-% of a strongly basic compound (SrO) with the remainder being prepared from neutral ($SiO_2$) and other compounds. With reference to Table 11, when tested in deionized water, according to the test method described in the examples, FAS glass decreases the pH to 6.5 within 15 minutes and thus would be considered a weakly acidic core material.

In some embodiments, the basicity of the core material or encapsulated core material can be determined by a change in pH of a specified amount (0.25 g) of material in 25 g of deionized water. An unencapsulated core material typically changes the pH of deionized water from neutral to a pH of at least 8.5 or 9. This typically occurs within 1, 2, 3, 4, or 5 minutes, but may take up to an hour or 24 hours. For example, with reference to Table 10, unencapsualted (e.g. bioactive glass) core material can provide a pH of 10 in water within 20 seconds. It takes a longer amount of time for the same encapsulated core material to provide such pH time since the core material cannot release hydroxyl ions until the inorganic shell material has sufficiently degraded, such as by dissolution. However, a rapid, but smaller pH change can occur in DI water even for encapsulated material if a small fraction of unencapsulated or less encapsulated material than the bulk of the sample is present.

In a favored embodiment, the basicity of the core material or encapsulated material can be determined by a change in pH of a specified amount (0.25 g) of material in a buffer solution, a solution of 15 g of deionized water and 10 g of an aqueous potassium acid phthalate buffer solution adjusted to a pH of 4.00 at 25° C. (with hydrochloric acid) (e.g. Buffer BDH5018) having a pH of 4. This test will be referred to herein as "the buffer test". When a strongly basic core material or encapsulated material is subjected to the buffer test, it also can reach a pH of at least 8.5 or 9. It is appreciated that a higher amount of hydroxyl ion is needed to change an acidic solution to a basic pH as compared to deionized water. Thus, it can take longer for this pH change to occur as compared to the same material in deionized water. In some embodiments, such pH change occurs in 5, 10 or 15 minutes, but may take up to 1 hour or 24 hour. It takes an even longer amount of time for the same encapsulated core material to provide such pH change since the core material cannot release hydroxyl ions that react with the acid until the inorganic shell material has sufficiently degraded, such as by dissolution and/or decomposition. In one embodiment, with reference to Table 8 unencapsulated (e.g. bioactive glass) core material achieves a pH of 8.5 according to the buffer test within 15 minutes and a pH of 9 within 40 minutes. The same encapsulated (e.g. bioactive glass) core material achieves a pH of 8.5 according to the buffer test within 35 minutes and the pH is continuing to rise after 1 hour.

Weakly basic core materials may provide a small increase in pH when tested according to the buffer test. For example, the pH may increase from 4 to 5. However, a weakly basic core material does not provide a sufficient amount of hydroxyl ions to cause the pH to reach a pH of at least 8.5 or 9 when tested according to the buffer test.

Thus, an encapsulated basic core material when added to water or buffer as described herein initially (i.e. immediately after submersion of the material in water or buffer) does not change the pH, but then the pH increases at various rates depending on the shell and basic core material.

In some embodiments, the basic core material is curable or self-setting when mixed with water, such as in the case of various natural and synthetic cements. Conventional natural (e.g. Portland) and synthetic cements typically comprises a major amount of calcium silicate (e.g. $3CaO—SiO_2$, $2CaO—SiO_2$) alone or in combination with one or more calcium aluminates (e.g. $3CaO—Al_2O_3$, $4CaO—Al_2O_3—Fe_2O_3$). When the basic core material is curable or self-setting, such basic core material may be the sole hardenable material of the hardenable composition. Thus, the first part of the composition may contain 100% encapsulated basic core material.

Water-based medical and dental cements as described in Mitra et al., U.S. Pat. No. 5,154,762 typically do not comprise a major amount of calcium silicate. Rather, such compositions generally comprise a particulate material that may be characterized as an acid-reactive metal oxide or acid-reactive glass filler (e.g., FAS glass). These types of fillers are not self-setting when mixed with water. However, such acid-reactive fillers can be combined with a polyfunctional acid component to provide a curable material.

In some embodiments, the encapsulated material is an encapsulated (e.g. dental) filler. Encapsulated (e.g. dental) fillers can comprise a substantial amount of neutral metal oxide that has low solubility as previously described in water or acidic solutions having a pH of 3-4. Neutral metal oxides include for example silica, zirconia, titania, and alumina. The amount of neutral metal oxide(s) can be at least 10, 15, 20, 25, 30 wt.-% ranging up to 50, 60, 70, 80, or 90 wt.-% of the total weight of the basic core material. Encapsulated calcium silicates may also be characterized as fillers due to their silica content.

The hardenable dental composition or other suitable (e.g. biological) carrier material comprises a material that promotes remineralization, such as a material that releases calcium ions, phosphorus containing ions (e.g. phosphate), fluoride ions, or a combination thereof. These materials can be present in the core of the encapsulated filler, can be provided as a second filler such as FAS glass, or can be provided as a separate component in the hardenable dental composition.

In some embodiments, the core of the encapsulated (e.g. filler) material preferably comprises a material that promotes remineralization, such as a material that releases calcium ions, phosphorus ions, fluoride ions, or a combination thereof. CaO can serve as both the highly basic material (e.g. compound) and a source of calcium ions as previously described. If the basic core material comprises a (e.g. strongly) basic material that does not release calcium ions, the core may further comprise another calcium material, such as a calcium salt (e.g. calcium glycerol phosphate). Other examples of calcium salt include calcium carbonate, calcium chloride, calcium caseinate, calcium citrate, calcium glubionate calcium gluceptate, calcium gluconate, calcium hydroxide, calcium hydroxyapatite, calcium lactate, calcium oxalate, calcium oxide, calcium pantothenate, calcium phosphate, calcium polycarbophil, calcium propionate, calcium pyrophosphate, and calcium sulfate.

In some embodiments, the core of encapsulated (e.g. dental) filler further comprises and is prepared from a material that promotes remineralization by release of fluoride ions. In other embodiments, the (e.g. dental) composition further comprises a second filler that comprises a material that promotes remineralization by release of fluoride ions. The core or second filler material comprises and is prepared from fluoride compounds such as $AlF_3$, $Na_2AlF_3$, and mixture thereof, in an amount ranging from about 5 to 40 wt.-%. In some embodiments, the amount of $AlF_3$ ranges from 10 to 30 wt.-% of the core or second filler material. In some embodiments, $Na_2AlF_3$ ranges from 2 to 10 wt.-% of the core or second filler material.

In some embodiments, the core of encapsulated (e.g. dental) filler further comprises a material that promotes remineralization by release of phosphorus ions. In other embodiments, the (e.g. dental) composition further comprises a second filler that comprises a material that promotes remineralization by release of fluoride ions. In some embodiments, the core or second filler material comprises and is prepared from phosphorus compounds such as $P_2O_5$, $AlPO_4$, and mixture thereof, in an amount ranging from 2 to 25 wt.-%. In some embodiments, the amount of $P_2O_5$ ranges from 2 to 15 wt.-% of the core or second filler material. In some embodiments, the amount of $AlPO_4$ ranges from 2 to 10 wt.-% of the core or second filler material.

The basic core can be encapsulated with an inorganic shell comprising a metal oxide with any suitable method, such as vapor deposition, atomic layer deposition (ALD), sputtering, or evaporation, which are techniques well known in the art.

In some embodiments, the method of making the encapsulating material comprises providing the basic core particles, as previously described and encapsulating the basic core particles with a (e.g. continuous, non-particulate) inorganic coating by means of least one of vapor deposition technique. Vapor deposition technique include chemical vapor deposition (CVD) such as atmospheric pressure chemical vapor deposition (APCVD), hydrolysis CVD, and plasma CVD).

Advantages of vapor deposition techniques for providing the coatings include that the coating is built up from molecular size species without interference from a solvent or liquid media. Some coating methods (e.g., ALD and CVD) tend to provide coatings composed of conformal layers on irregular materials (e.g., powder or porous particulate).

ALD and CVD are coating processes involving chemical reactions, where the chemical reactants used are referred to as chemical precursors. That is, they are precursors to the coating material (i.e., coating precursors) to be formed (e.g., a metal oxide coating). In some embodiments, a single coating precursor is used, while in other embodiments, at least two coating precursors are used. At least one coating precursor comprises at least one metal cation needed for the coating (e.g., a metal oxide coating).

A single coating precursor may be used when simple decomposition of the precursor (e.g., thermal decomposition or plasma enhanced decomposition) is sufficient to form a coating. At least two coating precursors (e.g., metal oxide precursors) are used when at least one coating precursor comprises at least one metal cation and chemically reacts with at least one additional precursor (i.e., a co-reactant) to form a coating (e.g., a metal oxide coating). The additional coating precursor is a co-reactant to the coating precursor comprising at least one metal cation. A co-reactant(s) chemically reacts with a coating precursor comprising at least one metal cation to form a coating.

ALD coatings are generally deposited one monolayer at a time via alternate pulses of a chemical precursor (e.g. a coating precursor comprising at least one metal cation), absorption of a monolayer of the precursor, removal of excess precursor, and pulsing of a co-reactant (e.g., a co-reactant to the coating precursor comprising at least one metal cation). As such, these coatings tend to be conformal and uniform. Alternatively, for example, ALD systems can also deposit thicker, non-self limiting coatings wherein significantly greater than a monolayer of each chemical reactant adsorbs into a substrate during each pulse or cycle, and results in the deposition of much larger amounts of coating.

CVD coatings can involve similar chemical reactions, but both precursors are typically supplied concurrently and continuously. Uniformity can be enhanced with continuous mixing of a powder being coated.

An effective coating method for making encapsulated materials described herein is atmospheric pressure CVD (APCVD). APCVD can be carried out in simple equipment such as glassware. In some embodiments, hydrolysis reactions are used to form (e.g. continuous) metal oxide coatings at temperatures ranging from room temperature (ranging from about 22° C.) up to about 180° C.

Exemplary precursors for ALD and CVD processes include coating precursors (e.g., metal oxide precursors) comprising at least one metal cation such as metal alkyls (e.g., trimethyl or triethyl aluminum, diethyl zinc), volatile metal chlorides (titanium tetrachloride, silicon tetrachloride, aluminum trichloride), silane, metal alkoxides (titanium isopropoxide, aluminum isopropoxide, silicon ethoxide), compounds with mixed alkyl, halide, hydride, alkoxy, and other groups, and other volatile metalorganic compounds. Exemplary co-reactants to the coating precursor comprising at least one metal cation (e.g., a metal oxide precursor comprising at least one metal cation) include water, oxygen, ozone, ammonia, and alkyl amines. In addition to metal oxides, other inorganic, nonmetallic coating materials are deposited using chemical reactions between a coating precursor and a co-reactant to the coating precursor (e.g., a metal nitride coating deposited using a metal nitride precursor comprising at least one metal cation and a co-reactant to the metal nitride precursor).

Exemplary (e.g. continuous) coatings comprise, for example, nonmetallic, inorganic materials such as metal (e.g., Al, Si, Ti, Zr, Mg, and Zn) oxides. In some embodiments, the shell material comprises at least 50, 60, 70, 80, 90 or 100 wt.-% of a single metal oxide or combination thereof. Exemplary metal oxides may include forms such as hydroxides, and hydrous oxides, as well as forms with mixed anions (e.g., oxide plus halides, hydroxyls, small amounts of alkyls or carboxylates, etc.). The shell material is predominantly inorganic having a carbon content no greater than 20, 10, 5, or 1 wt.-%. Further, the encapsulated basic material may also have a carbon content no greater than 20, 10, 5, or 1 wt.-%. The shell material may further comprise metal nitrides, metal sulfides, metal oxysulfides, and metal oxynitrides. The coatings can be amorphous, crystalline, or mixed, single or multiphase, and can contain one or more cations and one or more anions. In some embodiments, the coating is amorphous alumina with or without some hydroxyls or bound water.

The shell material may be a weakly basic material. However, the basicity of the shell material is not sufficient to produce the desired pH change, particularly according to the previously described buffer test or disk buffer test (as subsequently will be described).

In some embodiments, encapsulating the basic particle with a continuous coating is done via an APCVD coating process, wherein an alumina based coating is provided using trimethyl aluminum (TMA) and water. Precursors can be introduced into a reaction chamber by flowing a carrier gas through a bubbler of each liquid precursor. Generally, as is typical for CVD processes, the carrier gases with each component are delivered concurrently and continuously into the reaction chamber. Desirable flow rates and ratios can be adjusted to produce desired amounts and characteristics of coatings. In some embodiments, the trimethyl aluminum (TMA) flow rate and water flow rate independently range from at least 50 or 100 $cm^3$/min to 1000, 1500 or 2000 $cm^3$/min. The water flow rate is typically higher than the TMA flow rate by a factor ranging from 2× to 10× or greater. In some embodiments, flows of either precursor can be initiated or maintained individually for a period of time wherein no flow of the other precursor is present. In some embodiments, the flows of precursors can be changed or adjusted one or more times throughout a process.

In some embodiments, the ratio of a co-reactant (e.g., water) to a coating precursor comprising at least one metal cation (e.g., TMA) is higher initially than later in a process. In other embodiments, the ratio of a co-reactant (e.g., water) to a coating precursor comprising at least one metal cation is lower initially than later in a process. In some embodiments, composite particles are exposed to only a co-reactant (e.g., water) for an initial period prior to exposure to a coating precursor comprising at least one metal cation. In some embodiments, composite particles are exposed to only a coating precursor comprising at least one metal cation prior to exposure to a second reactant (e.g., a co-reactant to the coating precursor). In some embodiments, different flow conditions are maintained for at least 5 min (or in other embodiments, at least 10, 15, 20, 30, 45, 60, or 90 minutes) ranging up to 150 minutes.

In some embodiments, a coating of a first composition is deposited, followed by a coating of a second composition. For example, an alumina based coating can be deposited from TMA and water, followed by a titania based coating deposited from $TiCl_4$ and water.

In some embodiments, the shell, or in other word encapsulant, has an average thickness of at least 5, 10, 15, 20, or 25 nm. The thickness of the shell may range up to 250, 500, 750, or 1000 nm (1 micrometer). In some embodiments, such as in the case of encapsulated dental filler, the thickness of the shell typically ranges up to 50, 75, 100, 150, or 200 nm.

On a wt.-% basis the shell material is typically at least 0.1, 0.2, 0.3, 0.4, or 0.5 wt.-% of the total encapsulated material. The amount of shell material on a wt.-% basis can range up to 15 or 20 wt.-% of the total encapsulated material, but is more typically no greater than 10, 9, 8, 7, 6, or 5 wt.-%, In preferred embodiments, the shell material and thickness of the shell is selected to permit controlled and/or delayed release or reaction of the basic core material. In some embodiments, the amount of shell material on a wt.-% basis is no greater than 4.5, 4, 3.5, 3, 2 or 1 wt.-%.

In preferred embodiments, the shell is initially impermeable (i.e. material from a composition and core material cannot interact via simple diffusion through the shell). Interaction occurs after the shell is changed via interaction with other materials (e.g. degraded, corroded, or dissolved). Compositions (e.g. two-part compositions) can be designed that comprise components, such as water or acid, that degrade the shell. In other embodiments, shell degradation can take place due to coming in contact with water or an acidic component during use. In this embodiment, the source or water or acidic component can be a biological fluid (e.g. saliva or water retained in soft tissue surrounding a tooth or bone). In the case of dental sealants and restorations, it is surmised that the basic component can neutralize acids derived from bacteria or food sources that come in contact with the cured dental sealant.

With reference to Tables 4-7 of the forthcoming examples, in one embodiment, unencapsulated (e.g. Portland cement or tricalcium silicate) basic material provides a basic pH (e.g.

at least 8.5, 9, 9.5, 10, or 10.5) within 1 minute when subjected to the previously described buffer test. However, encapsulated (e.g. Portland cement or tricalcium silicate) basic material does not provide a basic pH (e.g. at least 8.5, 9, 9.5, 10, or 10.5) for 2, 3, 4, 5, 6, 7, 8, 9 or 10 minutes or greater according the buffer test. In some embodiments, the encapsulated (e.g. Portland cement) basic material does not provide a basic pH (e.g. at least 8.5, 9, 9.5, 10, or 10.5) for 15, 20, 25, 30, 35, 40, or 45 minutes. In some embodiments, the encapsulated (e.g. Portland cement) basic material does not provide a basic pH (e.g. at least 8.5, 9, 9.5, 10, or 10.5) for 100, 200, or 300 minutes.

With reference to Table 8 of the forthcoming examples, in another embodiment, unencapsulated (e.g. bioactive glass) basic material provides a basic pH (e.g. at least 8.5, 9, 9.5, 10, or 10.5) within 5 minutes when subjected to the previously described buffer test. However, encapsulated (e.g. bioactive glass) basic material does not provide a basic pH (e.g. at least 8.5, 9, 9.5, 10, or 10.5) for 30-40 minutes according the buffer test.

With reference to Table 9 of the forthcoming examples, in another embodiment, unencapsulated (e.g. Portland cement) basic material provides a basic pH of 11.5 within 20 seconds when tested in deionized water. However, encapsulated (e.g. Portland cement) basic material provides a basic pH of at least 8.5 within 20 second when tested in deionized water. With reference to Table 10 of the forthcoming examples, in another embodiment, unencapsulated (e.g. bioactive glass) basic material provides a basic pH of 10.5 within 20 seconds when tested in deionized water. However, encapsulated (e.g. bioactive glass) basic material provides a basic pH of at least 9.8 within 20 second. Thus, the change in pH of an acidic (e.g. buffer) solution can occur at a significantly slower rate than deionized water.

In preferred embodiments, the delayed release or reaction of the basic core material is utilized for increasing basicity of a (e.g. biological) carrier material, such as a hardenable dental material, at a later time such as after application to a tooth or bone structure and typically after curing. Unencapsulated basic material can produce a desirably large (yet undesirably rapid) increase in pH. The same encapsulated basic material can produce the desired increase in pH but after a longer duration of time or provide a slow, continuous release of basic material (e.g. hydroxyl ion).

The basicity of a (e.g. biological) carrier material, such as a hardenable (e.g. dental) composition. comprising encapsulated basic material can be evaluated by measuring the pH change of a disk (3.1 mm by 1.3 mm in height) of hardened (i.e. cured) material submerged in 1.5 ml of 10 mM $Na_2HPO_4$ (commonly known as PBS) buffer solution contained within a 2 ml plastic centrifuge tube. PBS buffer can be prepared by dissolving 8 g NaCl, 0.2 g of KCL, 1.44 g of $Na_2HPO_4$, and 0.24 g of $KH_2PO_4$ in 800 ml distilled $H_2O$, adjusting the pH to 7.4 with HCl, adjusting the volume to 1L with additional distilled water, and sterilizing by autoclaving. This test will subsequently be referred to as the disk buffer test.

A representative two-part hardenable (e.g. dental) composition that may be utilized for the purpose of evaluating an encapsulated (e.g. dental) basic material comprises a first part as described below and a second part comprising the encapsulated basic material. The first and second part are combined (at a 1:1 weight ratio), and radiation cured as described in further detail in the examples. In one embodiment, the second part comprises 65 wt.-% of an encapsulated basic material as described herein, 33.7 parts of hydroxyethyl methacrylate (HEMA), and 1 wt.-% of fumed silica. In another embodiment, the second part comprises 33.7 parts of hydroxyethyl methacrylate (HEMA), 16.25 to 65 wt.-% (e.g. 32.5 wt.-%) of encapsulated basic material as described herein, 0 to 32.5 wt.-% FAS glass, and 1 wt.-% of fumed silica.

First Part of Two-Part Hardenable Composition.

| Component | Weight Percent (wt.-%) in the Composition |
|---|---|
| Hydroxyethyl methacrylate (HEMA) | 12.07 |
| Butylated hydroxytoluene (BHT) | 0.03 |
| Camphorquinone (CPQ) | 0.33 |
| Deionized water | 22.01 |
| VBP | 25.83 |
| Calcium glycerylphosphate | 4.57 |
| Zr/Si Nanocluster Filler | 30.14 |
| Ytterbium fluoride | 5.02 |

In some embodiments, the concentration of encapsulated basic material is typically at least 2, 3, 4, 5, 10, 15, 20, 25, 30, 35, 40, 45, 50, 55, 60, or 65 wt.-% ranging up to 100% of the second part of the hardenable (e.g. dental) compositions. The total hardenable (e.g. dental composition) comprises half such concentration of encapsulated basic material. Hence, the concentration of encapsulated basic material is typically at least 1, 1.5, 2, 2.5, 5, 7.5, 10, 12.5, 15, 17.5, 20, 22.5, 25, 27.5, 30, or 32.5 wt.-% ranging up to 50 wt.-% of the total hardenable (e.g. dental) compositions. Although a formulation with 16.25 wt.-% of bioactive glass in the second part (8 wt-% of the total) exhibited marginal performance, it is surmised that the concentration of highly basic material (CaO, $Na_2O$) of the bioactive glass can be increased such that smaller concentrations can provide the delayed increase to a pH of at least 8.5 or 9.

With reference to Tables 12-22 of the forthcoming examples, in one embodiment, the encapsulated basic material provides a basic pH (e.g. at least 8.5, 9, 9.5, 10, or 10.5) within 46, 72, 100, 147, 260, 360 or 500 hours for compositions comprising greater than 16.25 wt.-% of encapsulated basic material.

The hardenable (e.g. dental) compositions are typically acidic (pH of 1, 2, 3, 4, 5 or 6) prior to curing due to the inclusion of acidic component(s) for a sufficient amount of time to provide good adhesion to bone or tooth structures. This time period can vary to some extent, but is acidic initially (immediately after submersion of the hardenable or hardened composition in water or buffer) and typically is acidic at least 30 seconds, 1, 2, 3, 4, or 5 minutes. In other embodiments, the hardenable or hardened (e.g. dental) compositions are initially neutral (pH of 7-7.5) and increase in basicity (pH of at least 8, 8.5, 9, 9.5, 10, 10.5 or 11) after various periods of time ranging from 1 hour to 1 day and in some embodiments ranging up to 2, 3, 4, 5, 6, or 7 days, or greater. However, when the released base neutralizes acid present in the oral environment, the hardened (e.g. dental) composition may remain neutral (pH of 7-7.5) due to the neutralization reaction proceeding at a rate equal to the rate of release of the basic (e.g. core) material.

In another embodiment, a representative non-aqueous two-part hardenable composition may be utilized for the disk buffer test, as further described in the forthcoming examples.

In some embodiments, the hardened dental composition comprising the encapsulated basic material increases the pH of the buffer solution by at least 0.05, 0.10, 0.15, 0.20, 0.25, or 0.30 within 15 or 39 hours.

In some embodiments, the hardenable (e.g. dental) composition may be characterized as a cement having multiple curing modes. In some embodiments, the cement cures through a first mechanism, via an ionic reaction between an acid and an acid reactive filler (e.g., FAS glass). Reaction of the encapsulated basic (e.g. filler) material is delayed as previously described, and is therefore typically not detrimental to the curing reaction. The cement also cures through a second mechanism, via photoinitiated free radical crosslinking of an ethylenically-unsaturated component. The cement may optionally cure through a third mechanism, via redox-initiated free radical crosslinking of the ethylenically-unsaturated component.

Such cements are typically formulated in two parts, the first part typically is a powder or liquid portion containing the encapsulated basic filler and an acid reactive (e.g. FAS-glass) filler for curing. The second part typically is an aqueous liquid portion containing an acidic polymer and water. In some cases, the encapsulated filler can be designed to provide controlled curing and subsequent continued rise in pH.

The cement may optionally contain a water-soluble reducing agent and water-soluble oxidizing agent in separate parts. If the reducing agent is present in the liquid portion, then the oxidizing agent is typically present in the powder portion, and vice-versa. Suitable reducing agents include ascorbic acid, sulfinic acid, barbituric acid and derivatives thereof, cobalt (II) chloride, ferrous chloride, ferrous sulfate, hydrazine, hydroxylamine (depending upon the choice of oxidizing agent) oxalic acid, thiourea, and salts of a dithionite or sulfite anion.

In other embodiments, the hardenable (e.g. dental) composition may lack water, such as in the case of dental sealants, the reducing agent and oxidizing agent need not be water soluble.

Suitable reducing agents include functional groups typically selected from amines, mercaptans, or mixtures thereof. If more than one functional group is present, they may be part of the same compound or provided by different compounds.

A preferred reducing agent is a tertiary aromatic amine. An example of a useful tertiary amine is

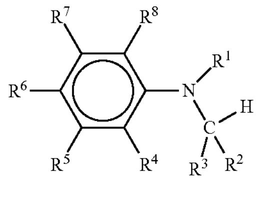

wherein each R group can be H or an organic group that does not adversely effect the initiation of hardening of the dental material. The organic groups generally do not sterically or electronically hinder the function of the reducing agent. Examples of such compounds are disclosed in WO 97/35916, published Oct. 2, 1997.

Preferably $R^1$ is an aliphatic group and $R^2$ and $R^3$ are independently (i.e., they may be the same or different) H, aromatic and/or aliphatic groups (preferably including up to 20 carbon atoms). Preferably, only one of $R^2$ and $R^3$ is an aromatic group. More preferably, $R^1$ is an alkyl group (preferably including up to 10 carbon atoms) optionally substituted with hydroxy groups, and $R^2$ and $R^3$ are H or alkyl groups (preferably including up to 10 carbon atoms) optionally substituted with hydroxyl groups. For certain preferred embodiments, $R^1$, $R^2$, and $R^3$ can also include a polymerizable functional group that will react with the functional groups of the resin. Preferably, at least one of $R^1$, $R^2$, and R includes a functional group such as an acrylate, methacrylate, acrylamide, vinyl, or other functional group present in the resins described above.

Preferably, $R^4$, $R^5$, $R^6$, $R^7$, and $R^8$ are independently H or aliphatic groups (preferably including up to 20 carbon atoms). More preferably, $R^4$, $R^5$, $R^6$, $R^7$, and $R^8$ are independently H or alkyl groups (preferably including up to 10 carbon atoms) optionally substituted with hydroxy groups. For certain preferred embodiments, $R^4$, $R^5$, $R^6$, $R^7$, and R can also include a polymerizable functional group that will react with the functional groups of the resin. Preferably, at least one of $R^4$, $R^5$, $R^6$, $R^7$, and $R^8$ includes a functional group such as an acrylate, methacrylate, acrylamide, vinyl, or other functional group present in the resins described above.

Particularly preferred aromatic tertiary amines are N,N-bis(2-hydroxyethyl)-p-toluidine (DHEPT), 2-(4-dimethylaminophenyl)ethyl alcohol (DMAPE), 4-tert butyl dimethyl aniline. Other compounds that are suitable include compounds derived from DMAPE with di- or multi-functional acid compounds such as adipic acid, sebacic acid, 1,3,5-benzene tricarboxylic acid, 1,2,4,5-benzene tetracarboxylic acid, and the like, or DMAPE with di- or multi-functional isocyanates such as hexamethylene diisocyanate, isophorone diisocyanate, and desmodur N-330 (a trifunctional isocyanate).

The tertiary amines may be polymerizable. Particularly preferred polymerizable aromatic tertiary amines include, but are not limited to, an adduct of IEM (2-isocyanatoethylmethacrylate) with N,N-bis(2-hydroxyethyl)-p-toluidine (DHEPT-di-IEM or bis-N,N-[2-(2-methacryloloxyethylaminocarbonyloxy)ethyl]-p-toluidine), an adduct of DMAPE with VDM (2-vinyl-4,4-dimethylazlactone) (DMAPE-VDM or 4-[2(2-acrylamido-2-methylpropionyloxy)ethyl)-N,N-dimethlyaniline), an adduct of a methacrylate di-ester with DHEPT (DHEPT-di-ester or bis-N,N-(2-methacryloloxyethyl)-p-toluidine), and an adduct of DHEPT with VDM (DHEPT-di-VDM or bis-N,N-[2-(2-acrylamido-2-methylpropionyloxy)ethyl]-p-toluidine).

Another preferred reducing agent is a mercaptan, that can include aromatic and/or aliphatic groups, and optionally polymerizable groups. Preferred mercaptans have a molecular weight greater than about 200 as these mercaptans have less odor. Particularly preferred mercaptans are isooctylthioglycoate (IOTG) and pentaerythritol tetrakis (3-mercaptopropionate) (PETMP).

The tertiary amines and mercaptans may be used alone or in admixture with one another. For example, the first initiator system can include one tertiary aromatic amine and one mercaptan, two tertiary aromatic amines, two mercaptans, one polymerizable tertiary aromatic amine, and the like. Other reducing agents, such as sulfinic acids, formic acid, ascorbic acid, hydrazines, and salts thereof, can also be used herein to initiate free radical polymerization. Preferably, however, the first initiator system includes a tertiary aromatic amine, a mercaptan, or a mixture thereof. Such reducing agents can function as both a component of the first initiator system and a component of the second initiator system.

When two or more reducing agents are used, they are preferably chosen such that at least one has a faster rate of activation than the other(s).

The encapsulated basic core material is typically combined with the part of the dental composition comprising the reducing agent.

Suitable oxidizing agents include peroxide compounds (i.e., peroxy compounds), including hydrogen peroxide as well as inorganic and organic peroxide compounds (e.g., "per" compounds or salts with peroxoanions). Examples of suitable oxidizing agents include, but are not limited to: peroxides such as benzoyl peroxide, phthaloyl peroxide, substituted benzoyl peroxides, acetyl peroxide, caproyl peroxide, lauroyl peroxide, cinnamoyl peroxide, acetyl benzoyl peroxide, methyl ethyl ketone peroxide, sodium peroxide, hydrogen peroxide, di-tert butyl peroxide, tetraline peroxide, urea peroxide, and cumene peroxide; hydroperoxides such as p-methane hydroperoxide, di-isopropyl-benzene hydroperoxide, tert-butyl hydroperoxide, methyl ethyl ketone hydroperoxide, and 1-hydroxy cyclohexyl hydroperoxide-1.

Other oxidizing compounds include persulfate compounds (e.g. ammonium persulfate, potassium persulfate), perborate compounds (e.g. sodium perborate), perchlorate compounds (e.g. sodium perchlorate), ozone, ozonides, etc. These oxidizing agents may be used alone or in admixture with one another.

Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The amount of reducing agent and oxidizing agent is sufficient to provide the desired degree of polymerization of the ethylenically-unsaturated component and the desired cure rate. In some embodiments, the hardenable (e.g. dental) composition cures within 5, 4, 3, 2, or 1 minute.

The amount of reducing agent is typically at least 0.01, 0.02, 0.03, 0.04, 0.05, 0.06, 0.07, 0.08, 0.09 or 1 wt.-% ranging up to 5, 5.5, 6, 6.5, 7, 7.5, 8, 8.5, 9, 9.5 or to 10 wt. % based on the total weight (including water) of the unset cement or other hardenable (e.g. dental) composition. In some embodiments, the hardenable (e.g. dental) composition comprises at least 1.5, 2.0, 2.5, 3.0, 3.5, 4.0, 4.5, or 5 wt.-% of reducing curing agent.

The amount of oxidizing agent is typically at least 0.01, 0.02, 0.03, 0.04, 0.05, 0.06, 0.07, 0.08, 0.09 or 1 wt.-% ranging up to 5, 5.5, 6, 6.5, 7, 7.5, 8, 8.5, 9, 9.5 or 10 wt. % based on the total weight (including water) of the unset cement or other hardenable (e.g. dental) composition.

In some embodiments, the hardenable (e.g. dental) composition comprises at least 1.5, 2.0, 2.5, 3.0, 3.5, 4.0, 4.5, or 5 wt.-% of oxidizing curing agent. The reducing agent or the oxidizing agent can be encapsulated with a polymer as described in Mitra et al., U.S. Pat. No. 5,154,762. When the hardenable (e.g. dental) composition cures through redox-initiated free radical crosslinking of the ethylenically-unsaturated component, the composition comprises a sufficient amount of oxidizing agent for the crosslinking reactions that is not encapsulated within an inorganic shell comprising a metal oxide. The hardenable (e.g. dental) composition may also comprise oxidizing agent encapsulated in an inorganic shell comprising a metal oxide for the purpose of increasing the pH over a duration of time.

The cements are not limited to two-part powder-liquid compositions. For example, one part anhydrous formulations can be prepared. These can be sold in dry form and prepared for use by adding water. Also, two part paste-paste formulations can be prepared by adding to the encapsulated basic and/or additional acid reactive (e.g. FAS glass) filler a suitable polymerizable liquid that does not react with that filler (e.g., 2-hydroxyethyl methacrylate, or "HEMA"), yielding a first paste. The acidic polymer described above is combined with a suitable filler that does not react with the acidic polymer (e.g., ground quartz), yielding a second paste. The two pastes are prepared for use by stirring them together.

The cements contain water at the time of use. The water can be present in the composition as sold, or added just prior to use. The water can be distilled, deionized or plain tap water. The amount of water is generally sufficient to provide adequate handling and mixing properties and to permit the transport of ions in the filler-acid reaction. The amount of water is typically at least 1, 2, 3, 4, or 5% and typically no greater than 20 or 25 of the total weight of the cements, (i.e. the combination of the first and second part and any water that is added).

The cements are typically ionically hardenable, i.e. can react via an ionic reaction to produce a hardened mass. The ionic reaction occurs predominantly between acid groups on the polymer and the acid reactive (e.g. FAS glass) filler.

In some embodiments, an acid-reactive (FAS) glass is utilized is combination with the encapsulated basic (e.g. filler) material. In some embodiments, the amount of FAS glass is at least 5, 10, 15, 20, 25, 30, 35, or 40 wt.-% ranging up to about 50, 55 or 60 wt.-% of the first part of a two-part composition. Since the first part typically represent half of the total hardenable (e.g. dental) composition, the concentration of acid-reactive (FAS) glass in the total is half the concentration just described. In addition to participation in the ionic reaction, the FAS glass releases phosphorus and fluorine ions that are known to promote remineralization.

In some embodiments, the concentration of acid-reactive (FAS) glass is greater than the concentration of encapsulated basic (e.g. filler) material. In other embodiment, the concentration of encapsulated basic (e.g. filler) material is greater than the concentration of acid-reactive (FAS) glass. In some embodiments, the weight ratio of encapsulated basic filler to unencapsulated acid-reactive (FAS) glass is typically at least or greater than 1:1, such as 1.5:1, 2:1, 2.5:1, or 3:1 ranging up to 5:1, 6:1, 7:1, 8:1, 9:1, or 10:1 in the second part of a two-part composition.

The cements can further comprise at least one ethylenically-unsaturated moiety. The ethylenically-unsaturated moiety can be present as a separate ingredient (for example, as an acrylate- or methacrylate-functional monomer) or be present as a group on another ingredient such as the acidic polymer.

The ethylenically unsaturated moiety is typically a (e.g. terminal) free radically polymerizable group including (meth)acryl such as (meth)acrylamide ($H_2C{=}CHCON—$ and $H_2C{=}CH(CH_3)CON—$) and (meth)acrylate ($CH_2CHCOO—$ and $CH_2C(CH_3)COO—$). Other ethylenically unsaturated polymerizable groups include vinyl ($H_2C{=}C—$) including vinyl ethers ($H_2C{=}CHO—$). The ethylenically unsaturated terminal polymerizable group(s) is preferably a (meth)acrylate group, particularly for compositions that are hardened by exposure to actinic (e.g. UV or blue light) radiation. Further, methacrylate functionality is typically preferred over the acrylate functionality in curable dental compositions.

In some embodiments, the ethylenically-unsaturated component is a water-miscible or water-soluble (meth)acrylate such as 2-hydroxyethyl methacrylate, hydroxymethyl methacrylate, 2-hydroxypropyl methacrylate, tetrahydrofurfuryl methacrylate, glycerol mono- or di-methacrylate, trimethylol propane trimethacrylate, ethylene glycol dimethacrylate, polyethylene glycol (e.g. 400 and other molecular weights) dimethacrylate, urethane methacrylates, acrylamide, methacrylamide, methylene bis-acrylamide or methacrylamide, and diacetone acrylamide and methacrylamide are preferred. Mixtures of ethylenically-unsaturated moieties can be used if desired. Preferably, the ethylenically-unsaturated moieties are present as groups on the acidic polymer, as described in more detail below.

The second part comprises an organic or inorganic acid component. In some embodiments, the acid component is a polycarboxylic acid such as poly(maleic)acid or poly(itaconic) acid. In other embodiments, the acid component is a polyacrylic acid or phosphorus-containing acid.

In some embodiments, the acidic component is an acidic polymer. Suitable acidic polymers include those listed at column 2, line 62 through column 3, line 6 of U.S. Pat. No. 4,209,434. Preferred acidic polymers include homopolymers and copolymers of alkenoic acids such as acrylic acid, itaconic acid and maleic acid.

In some embodiments, the acidic polymer may be characterized as a photocurable ionomer, i.e. a polymer having pendent ionic groups capable of a setting reaction and pendent free radically polymerizable groups to enable the resulting mixture to be polymerized, i.e., cured, upon exposure to radiant energy.

As described for example in U.S. Pat. No. 5,130,347, photocurable ionomers have the general formula:

$$B(X)_m(Y)_n$$

wherein

B represents an organic backbone, each X independently is an ionic group, each Y independently is a photocurable group, m is a number having an average value of 2 or more, and n is a number having an average value of 1 or more.

Preferably the backbone B is an oligomeric or polymeric backbone of carbon-carbon bonds, optionally containing non-interfering substituents such as oxygen, nitrogen or sulfur heteroatoms. The term "non-interfering" as used herein refers to substituents or linking groups that do not unduly interfere with either the photocuring reaction of the photocurable ionomer.

Preferred X groups are acidic groups, with carboxyl groups being particularly preferred.

Suitable Y groups include, but are not limited to, polymerizable ethylenically unsaturated groups and polymerizable epoxy groups. Ethylenically unsaturated groups are preferred, especially those that can be polymerized by means of a free radical mechanism, examples of which are substituted and unsubstituted acrylates, methacrylates, alkenes and acrylamides.

X and Y groups can be linked to the backbone B directly or by means of any non-interfering organic linking group, such as substituted or unsubstituted alkyl, alkoxyalkyl, aryl, aryloxyalkyl, alkoxyaryl, aralkyl, or alkaryl groups.

Preferred photocurable ionomers are those in which each X is a carboxyl group and each Y is an ethylenically unsaturated group such as a (meth)acrylate group that can be polymerized by a free radical mechanism. Such ionomers are conveniently prepared by reacting a polyalkenoic acid (e.g., a polymer of formula $B(X)_{m+n}$ wherein each X is a carboxyl group) with a coupling compound containing both an ethylenically unsaturated group and a group capable of reacting with a carboxylic acid group such as an NCO group. The resulting photocurable ionomer preferably has least one of the free radically polymerizable (e.g. (meth)acrylate group) is linked to said ionomer by means of an amide linkage. The molecular weight of the resultant photocurable ionomers is typically between about 1000 and about 100,000 g/mole.

The (e.g. photocurable ionomer) acidic polymer typically has a weight average) molecular weight of at least 5000 g/mole ranging up to about 100,000 g/mole as determined using gel permeation chromatography and polystyrene standards. In some embodiments, the (e.g. photocurable ionomer) acidic polymer has a molecular weight of less than 50,000 or 25,000 g/mole.

The concentration of acidic component, such as photocurable ionomer is typically at least 5, 6, 7, 8, 9, or 10 wt.-% and typically no greater than 30, 25, 20, or 15 wt.-% of the first part of a two-part composition. Since the first part represents only half of the total hardenable (e.g. dental) composition, the concentration of acidic component, such as photocurable ionomer, in the total is about half the concentration just described.

In some embodiments, the acid component is a hardenable component in the form of ethylenically unsaturated compounds with acid and/or acid-precursor functionality. Acid-precursor functionalities include, for example, anhydrides, acid halides, and pyrophosphates. The acid functionality can include phosphoric acid functionality, phosphonic acid functionality, sulfonic acid functionality, or combinations thereof. Typically, the adhesive compositions described herein comprise little (e.g. less than 10 wt-%, 5 wt-%, or 1 wt-%) or no ethylenically unsaturated compounds with carboxylic acid functionality when the composition comprises a radiopaque filler comprises a basic surface, such as in the case of zirconia.

Ethylenically unsaturated compounds with acid functionality include, for example, alpha, beta-unsaturated acidic compounds such as glycerol phosphate mono(meth)acrylates, glycerol phosphate di(meth)acrylates, hydroxyethyl (meth)acrylate phosphates (e.g. HEMA-P), bis((meth)acryloxyethyl) phosphate, ((meth)acryloxypropyl) phosphate, bis((meth)acryloxypropyl) phosphate, bis((meth)acryloxy) propyloxy phosphate, (meth)acryloxyhexyl phosphate, bis ((meth)acryloxyhexyl) phosphate (e.g. MHP), (meth)acryloxyoctyl phosphate, bis((meth)acryloxyoctyl) phosphate, (meth)acryloxydecyl phosphate, bis((meth)acryloxydecyl) phosphate, and caprolactone methacrylate phosphate.

In some embodiments, the (e.g. dental) compositions further comprises other (i.e. second) filler in addition to the encapsulated filler described herein. The second filler typically does not comprise a (e.g. strongly) basic core material as described herein. The second filler typically comprises neutral metal oxides having low solubility, as previously described. The second filler may also be weakly basic or weakly acidic.

In some embodiments, the second filler is an acid-reactive (FAS glass) filler, as previously described.

In some embodiments, the other filler comprises (e.g. inorganic metal oxide) nanoparticles. Such nanoparticles, or in other words "nanoscopic fillers" can be used as viscosity and thixotropy modifiers. Such nanoparticles can also contribute in part to the mechanical properties of the hardenable dental composition. Due to their size, such nanoparticles also contribute to the refractive index of the polymerizable resin.

In some embodiments, the inorganic oxide nanoparticles have a primary particle size of no greater than 100 nm. The primary particle size typically refers to the size of a discrete, unaggregated particle. In other less common embodiments, the nanoparticle may be an aggregate of two or more (e.g. fused or covalently) bonded particles, wherein the aggregate has a particle size of no greater than 100 nm. The average particle size can be determined by cutting a thin sample of hardened dental composition and measuring the particle diameter of about 50-100 particles using a transmission electron micrograph at a magnification of 300,000 and calculating the average. The nanoparticles can have a unimodal or polymodal (e.g., bimodal) particle size distribution. In some embodiments, the (e.g. zirconia) nanoparticles have an average particle size of at least about 2, 3, 4, or 5 nanometers (nm). In some embodiments, the (e.g. zirconia) nanoparticles have an average particle size no greater than about 50, 40, 30, 25, 15, or 10 nanometers (nm).

The dental composition optionally further comprises (e.g. inorganic metal oxide) nanoparticles having a relatively low refractive index, such as silica. The inclusion of the low refractive index nanoparticle can reduce the refractive index of the polymerizable resin. Suitable silica nanoparticles are commercially available from Ecolab (St. Paul, MN) under the product designation NALCO COLLOIDAL SILICAS. For example, preferred silica particles can be obtained from using NALCO products 1034A, 1040, 1042, 1050, 1060, 2327 and 2329.

Silica nanoparticles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Ecolab) and those which are low in sodium concentration and can be acidified by admixture with a suitable acid (e.g. Ludox colloidal silica made by E. I. Dupont de Nemours & Co. or Nalco 2326 from Ecolab).

In some embodiments, the dental composition comprises at least 0.5, 1, 1.5, or 2 wt.-% of low refractive index (e.g. silica) nanoparticles. The amount of low refractive index (e.g. silica) nanoparticles is typically no greater than 30, 25, 20, 15 or 5 wt.-% of the dental composition. In other embodiments, the dental composition comprises less than 1, 0.5, 0.25, 0.1, or 0.005 wt.-% of low refractive index (e.g. silica) nanoparticles or is substantially free of low refractive index (e.g. silica) nanoparticles.

When low refractive index (e.g. silica) nanoparticles are included in the dental composition, the concentration of low refractive index (e.g. silica) nanoparticles is generally less than the concentration of high refractive index (e.g. zirconia) nanoparticles. Thus, the weight or volume concentration of high refractive index (e.g. zirconia) nanoparticles is typically greater than the weight or volume concentration of low refractive index (e.g. silica) nanoparticles. In some embodiments, the weight or volume ratio of high refractive index (e.g. zirconia) nanoparticles to low refractive index (e.g. silica) nanoparticles is at least 1.1 to 1, 1.2 to 1, 1.3 to 1, 1.4 to 1, 1.5 to 1, 1.6 to 1, 1.7 to 1, 1.8 to 1, 1.9 to 1, or 2 to 1. In some embodiments, the weight or volume ratio of high refractive index (e.g. zirconia) nanoparticles to low refractive index (e.g. silica) nanoparticles is at least 2.1 to 1, 2.2 to 1, 2.3 to 1, or 2.4 to 1. In some embodiments, the weight or volume ratio of high refractive index (e.g. zirconia) nanoparticles to low refractive index (e.g. silica) nanoparticles is no greater than 100 to 1, 75 to 1, 50 to 1, 25 to 1, 10 to 1, or 5 to 1.

Some suitable low refractive index (e.g. silica) nanoparticles and high refractive index (e.g. zirconia) nanoparticles are disclosed in U.S. Pat. No. 6,387,981 (Zhang et al.) and U.S. Pat. No. 6,572,693 (Wu et al.) as well as PCT International Publication Nos. WO 01/30304 (Zhang et al.), WO 01/30305 (Zhang et al.), WO 01/30307 (Zhang et al.), WO 03/063804 (Wu et al.), U.S. Pat. No. 7,090,721 (Craig et al.), U.S. Pat. No. 7,090,722 (Budd et al.), U.S. Pat. No. 7,156,911 (Kangas et al.), U.S. Pat. No. 7,241,437 (Davidson et al.) and U.S. Pat. No. 7,649,029 (Kolb et al.).

The dental compositions described herein preferably comprise appreciable amounts of inorganic metal oxide filler. Fillers used in dental applications are typically ceramic in nature.

Fillers may be selected from one or more of a wide variety of materials suitable for incorporation in compositions used for dental applications, such as fillers currently used in dental composites and dental (e.g. crown) articles, and the like. The filler is generally non-toxic and suitable for use in the mouth. The filler can be radiopaque, radiolucent, or nonradiopaque. In some embodiments, the filler typically has a refractive index of at least 1.500, 1.510, 1.520, 1.530, or 1.540.

It is common to include up to about 5 wt-% of a component, such as $YbF_3$ to increase the radiopacity. In some embodiments, the radiopacity of the cured dental composition is at least 3 mm thickness of aluminum.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

The dental compositions described herein comprise inorganic metal oxide filler material that is larger in size than the nanoparticles. As previously described, the nanoparticles are typically discrete, unaggregated particles having a particle size of no greater than 100 nm. In contrast, the inorganic metal oxide filler is a particulate or fibrous material having at least one dimension greater than 100 nm such as at least 150 nm or at least 200 nm. In the case of particulate fillers, the average particle size of a discrete unaggregated particle or an aggregated particle is at least 200 nm. Inorganic metal oxide filler particles are very effective for improving post-cure wear properties.

In some embodiments, the filler can comprise crosslinked organic material that is insoluble in the polymerizable resin, and may optionally be filled with inorganic filler. Examples of suitable organic filler particles include filled or unfilled pulverized polycarbonates, polyepoxides, poly(meth)acrylates and the like.

In some embodiments, the dental compositions described herein comprises non-acid-reactive fillers such as quartz, fumed silica, non-vitreous microparticles of the type described in U.S. Pat. No. 4,503,169 (Randklev), as well as nanocluster fillers, such as described in U.S. Pat. No. 6,730,156 (Windisch et al.), U.S. Pat. No. 6,572,693 (Wu et al.), and U.S. Pat. No. 8,722,759 (Craig).

In typical embodiments, a suspending agent may be used, such as fumed silica. Fumed silica is commercially available as the trade designation "Cab-O-Sil" from Cabot Corporation and as the trade designation "Aerosil" from Degussa, Inc. The suspending agent can thicken the composition and thereby increase the viscosity.

The concentration of suspending agent is typically at least 0.05, 0.10, 0.15, or 0.2% by weight and may range up to 5% by weight. In some embodiments concentration of suspending agent may be reduced when higher concentrations of encapsulated basic materials are employed.

In some embodiments, the filler comprises nanoparticles in the form of nanoclusters, i.e. a group of two or more particles associated by relatively weak, but sufficient intermolecular forces that cause the particles to clump together, even when dispersed in a hardenable resin. Preferred nanoclusters can comprise a loosely aggregated substantially amorphous cluster of non-heavy metal oxide (e.g. silica) particles, and heavy metal oxide (i.e. having an atomic number greater than 28) such as zirconia. The zirconia can be crystalline or amorphous. In some embodiments, the zirconia may be present as a particle. The particles from which the nanocluster is formed preferably have an average diameter of less than about 100 nm. However, the average particle size of the loosely aggregated nanocluster is typically considerably larger.

In some embodiments, the (e.g., dental) composition further comprises a second filler comprising neutral metal oxides, such as zirconia/silica nanocluster filler. In the case of two part dental compositions, fillers comprising neutral metal oxides are present in a substantial amount in a first or second liquid containing part. In some embodiments, neutral or unreactive fillers are present in either or both of an acidic and non-acidic part, whereas acid reactive fillers (e.g. FAS glass) and/or encapsulated basic cores are present in a non-acidic part and react with an acidic part after mixing.

In some embodiments, the first part of the hardenable (e.g. dental) composition comprises a second filler comprising neutral metal oxides, such zirconia/silica nanocluster filler in an amount of at least 5, 10, 15, or 20 wt.-% ranging up to 30, 35, or 40 wt.-%. The total hardenable (e.g. dental) composition comprises about half such concentration of a second filler comprising neutral metal oxides, such as zirconia/silica nanocluster filler.

In some embodiments, a (e.g. one part) hardenable (e.g. dental restoration) composition comprises a second filler comprising neutral metal oxides, such zirconia/silica nanocluster filler in an amount of at least 5, 10, 15, 20, 25, 30, 35, 40, 45, or 50 wt.-% of the total hardenable (e.g. dental restoration) composition. The amount of second filler is typically no greater than 80, 75, 70, 65, or 60 wt.-% of the total hardenable (e.g. dental restoration) composition.

In some embodiments, the second filler may also be encapsulated with a shell material comprising a metal oxide such as described in U.S. Pat. No. 7,396,862.

Mixtures of fillers can also be used.

In typical embodiments, second fillers may comprise a surface treatment to enhance the bond between the nanoparticles and inorganic oxide filler and the resin. Various surface treatments have been described in the art including for example organometallic coupling agents and carboxylic acids such as described in U.S. Pat. No. 8,647,510 (Davidson et al.) The encapsulated basic material may also optionally comprise a surface treatment.

Suitable copolymerizable organometallic compounds may have the general formulas: $CH_2{=}C(CH_3)_mSi(OR)_n$ or $CH_2{=}C(CH_3)_mC{=}OOASi(OR)_n$; wherein m is 0 or 1, R is an alkyl group having 1 to 4 carbon atoms, A is a divalent organic linking group, and n is from 1 to 3. The organometallic coupling agent may be functionalized with reactive curing groups, such as acrylates, methacrylates, vinyl groups and the like. Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependent upon several factors such as particle size, particle type, modifier molecular weight, and modifier type. In general it is preferred that approximately a monolayer of modifier is attached to the surface of the particle.

Various ethylenically unsaturated monomers can be utilized in the dental composition. The ethylenically unsaturated monomers of the dental composition are typically stable liquids at about 25° C. meaning that the monomer do not substantially polymerize, crystallize, or otherwise solidify when stored at room temperature (about 25° C.) for a typical shelf life of at least 30, 60, or 90 days. The viscosity of the monomers typically does not change (e.g. increase) by more than 10% of the initial viscosity.

Particularly for dental restoration compositions, the ethylenically unsaturated monomers generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight monomer lacking such substituents).

The curable (e.g. dental) composition can include a wide variety of other ethylenically unsaturated compounds (with or without acid functionality), epoxy-functional (meth)acrylate resins, vinyl ethers, and the like.

The (e.g., photopolymerizable) dental compositions may include free radically polymerizable monomers, oligomers, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof.

Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri (meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable (e.g. dental) composition may contain a monomer having hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth) acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are available from a wide variety of commercial sources, such as Sigma-Aldrich, St. Louis.

In some embodiments, the first part of the two-part hardenable (e.g. dental) composition comprises a monomer having hydroxyl groups and ethylenically unsaturated groups in a single molecule, such as HEMA. In some embodiments, the amount of ethylenically unsaturated compounds with acid functionality (e.g. HEMA) is at least 5, 10, 15, 20, 25, 30, wt.-% ranging up to about 35, 40, 45 or 50 wt.-% of the first part of a two-part composition. Since the first part represents only half of the total hardenable (e.g. dental) composition, the concentration of ethylenically unsaturated compounds with acid functionality (e.g. HEMA) in the total is about half the concentration just described.

The (e.g. dental) compositions described herein may include one or more curable components in the form of ethylenically unsaturated compounds with acid functionality. Such components contain acidic groups and ethylenically unsaturated groups in a single molecule. When present, the polymerizable component optionally comprises an ethylenically unsaturated compound with acid functionality. Preferably, the acid functionality includes an oxyacid (i.e., an oxygen-containing acid) of carbon, sulfur, phosphorus, or boron. However, in some embodiments, the dental compositions are substantially free (less than 1, 0.5, 0.25, 0.1, or 0.005 wt.-%) of ethylenically unsaturated compounds with acid functionality As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates (GDMA-P), hydroxyethyl (meth)acrylate (e.g., HEMA) phosphates, bis((meth) acryloxyethyl) phosphate, ((meth)acryloxypropyl) phosphate, bis((meth)acryloxypropyl) phosphate, bis((meth) acryloxy)propyloxy phosphate, (meth)acryloxyhexyl phosphate, bis((meth)acryloxyhexyl) phosphate, (meth) acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly (meth)acrylated poly(meth)acrylic acid, poly(meth)acrylated polycarboxyl-polyphosphonic acid, poly(meth) acrylated polychlorophosphoric acid, poly(meth)acrylated polysulfonate, poly(meth)acrylated polyboric acid, and the like, may be used as components. Also monomers, oligomers, and polymers of unsaturated carbonic acids such as (meth)acrylic acids, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth) acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH), group, wherein x=1 or 2, and wherein the at least one —O—P(O)(OH), group and the at least one (meth)acryloxy group are linked together by a C5-C12 hydrocarbon group; an ethylenically unsaturated compound without acid functionality; an initiator system; and a filler.

An initiator is typically added to the mixture of polymerizable ingredients. The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

In some embodiments, the mixture of monomers is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm. Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays or with blue light. For this embodiment, suitable photoinitiators include those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl) butanone (IRGACURE 369), 2-methyl-1-[4-(methylthio) phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-6000 $mW/cm^2$. An intensity of 1000 $mW/cm^2$ for 20 seconds can generally provide the desired cure. A variety of conventional lights for hardening such compositions can be used.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water. In some embodiments, the (e.g. one-part) dental compositions comprise water, typically in an amount no greater than 5 wt.-% of the total dental composition.

If desired, the compositions can contain additives such as indicators, dyes including photobleachable dyes, pigments, inhibitors, accelerators, viscosity modifiers, wetting agents, buffering agents, radical and cationic stabilizers (for example BHT,), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. In some embodiments, a dental adhesive may be applied prior to application of the curable dental restoration material described herein. Dental adhesives are also typically hardened by curing concurrently with curing the highly filled dental restoration composition. The method of treating an oral surface may comprise providing a dental article and adhering the dental article to an oral (e.g. tooth) surface.

In one embodiment, the cured dental composition can be used for pulp capping. In this embodiment, cell proliferation of dental pulp stem cells contacted with the cured dental composition (e.g. same molded disk as utilized for the buffer disk test) was evaluated in the manner described in further detail in the examples. The average cell proliferation was at least 75% of the control (wherein no disk of cured dental composition was present). In some embodiments, the average cell proliferation was at least 80, 85, or 90% of the control. The average alkaline phosphatase (ALP) activity also increased as compared to the control. In some embodiments, the average ALP activity was at least 0.4, 0.5, 0.6, 0.7, 0.8, 0.9, 1.0 mU/mL ranging up to 1.1 or 1.2 mU/mL or greater.

In another embodiment, the cured dental composition can be used as an adhesive. The cured dental composition can exhibit adhesion as measured according to the test method described in the examples of at least 1, 2, 3, 4, 5, 6, 8, 9, or 10 MPa. In some embodiments, the adhesion can range up to 20 MPa or greater.

As used herein, "dental composition" refers to a material comprising filler capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g. two-part cements), primers (e.g., orthodontic primers), liners (applied to the base of a cavity to reduce tooth sensitivity), root repair and pulp capping, coatings such as sealants (e.g., pit and fissure) and varnishes; and resin restoratives (also referred to as direct composites) such as dental fillings, as well as crowns, bridges, and articles for dental implants. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restoration articles such as a crown, bridge, or orthodontic appliance to a tooth surface or an implant abutment.

In one embodiment, a two-part (e.g. dental sealant) composition is described wherein each part of the comprises a polymerizable resin. In some embodiments, neither part contains water or an acidic component. The polymerizable resin is typically a mixture of acrylic monomers. One common acrylic monomer is described in U.S. Pat. No. 3,066,112. Such acrylic monomer is the reaction product of bisphenol A or other bisphenol with glycidyl methacrylate, the reaction product being commonly referred to in the art as Bis-GMA monomer. Typically, this monomer is combined with various other (e.g. lower molecular weight, lower viscosity) monomers such as di(meth)acrylate monomers (e.g. tetraethyleneglycol dimethacrylate, ethyleneglycol dimethacrylate, triethyleneglycol dimethacrylate, etc.) or other (meth)acrylate monomers.

The two part (e.g. dental sealant) composition described here comprises a "redox" curing system, as previously described; optionally in combination with a second initiator system utilizing free radical polymerization. The second initiators are preferably free radical photoinitiators, that may be activated upon irradiation with actinic radiation (using a conventional dental curing light) initiates the polymerization (or hardening) of the free radically polymerizable composition.

In another embodiment, one part (e.g. dental restoration) composition is described. Such composition may also comprise a polymerizable resin comprising (e.g. 15 to 35 wt-%) Bis-GMA with various other (e.g. lower molecular weight, lower viscosity) monomers, as previously described. However, one part (e.g. dental restoration) composition typically further comprises appreciable amounts of filler. The filler comprises the encapsulated basic material described herein, typically in combination with second fillers as previously described. The total amount of filler is typically at least 50, 55, 60, 65, 70, 75 or 80 wt.-% solids.

The curable (e.g. dental) composition can have various viscosity criteria depending on the end use, dispensing device, and method of applying. Overall the viscosity can range from 200 cps to 100,000 cps or greater at 23° C.

For example, when the composition is a two part hardenable (e.g. dental) composition comprising liquid (e.g. polymerizable resin) materials the difference viscosity between the first and second part is typically no greater than 90, 85, 80, 75, 70, 65, 60, 55 of the higher viscosity composition/part. In some embodiments, such as when the composition is applied by use of a dispensing (e.g. syringe) device comprising a static mix, the difference viscosity between the first and second part is typically no greater 50, 45, 40, 35, 30, 25, 20, 15, or 10%.

As yet another example, wherein the composition is a two part hardenable (e.g. dental) composition comprising liquid (e.g. polymerizable resin) materials intended to seal fissures (e.g. of a tooth surface), it is of importance that the composition has a very low viscosity. In some embodiments, each part has a viscosity no greater than 6500, 6000, 5500, or 5000 cps at 23° C. In some embodiments, the viscosity of each of the components is no greater than 4500, 4000, 3,500, or 3000 cps at 23° C. The viscosity of each of the components is typically at least 200, 300, 400 or 500 cps at 23° C.

In another embodiment, wherein the composition is a highly filled hardenable (e.g. dental) composition comprising liquid (e.g. polymerizable resin) materials intended for dental restorations, the viscosity may be at least 40,000 cps; 45,000 cps; or 50,000 cps.

When the viscosity is less than about 50,000 cps, the viscosity can be determined by a Brookfield viscometer and type-A T-bar spindle at 23° C. and shear rate of 100 $s^{-1}$.

Highly filled hardenable (e.g. dental) composition comprising liquid (e.g. polymerizable resin) materials intended for dental restorations can have even higher viscosities. When the hardenable (e.g. dental) composition has a viscosity that is too high to be measured with a Brookfield viscometer, other methods can be used to determine the viscosity.

Rheological measurements of viscosity can be made on an AR-G2 Rheometer (TA Instruments), temperature controlled to 25° C., using an 8 mm diameter flat plate geometry. Self-adhesive sandpaper (9 micron grit) can be placed on both the geometry (8 mm diameter sandpaper circle) and the stage (large 15×15 mm square piece of sandpaper). The hardenable (e.g. dental) material can be placed on the stage and the geometry can be pushed into the material until a gap between it and the stage of 1,000 microns is reached. Excess material can be removed by cutting it off using a razor blade. The following procedure can be used to make measurements. The material can be allowed to rest for 3 minutes in a conditioning step. Next, with the rheometer operating in oscillatory mode, a frequency sweep step can be employed to measure the viscosity of the material at different shear rates. The angular frequency can be stepped through values from 0.1 to 10.0 rad/s with 5 points per decade at a strain of 0.4%. The material can then be allowed to equilibrate for 2 minutes. Finally, the yield stress of the material can be determined through another oscillatory measurement. In a stress sweep measurement, the oscillatory stress can be stepped from 0.1 to 10,000 Pa, recording 15 points per decade. The angular frequency can be held fixed at 10 rad/sec. The elastic modulus (G') can be monitored. The yield stress can be defined as the intersection of a horizontal line drawn through the portion of the data where G' is constant with stress (low stress values), and a line that matches the maximum slope of the portion of the curve where G' decreases quickly with increasing stress. Yield stress can be measured of the minimum amount of force needing to be applied to a material to make it move (or yield). The collected data can be analyzed using the "Rheology Advantage Data Analysis" software supplied with the instrument.

In some embodiments, highly filled hardenable (e.g. dental) composition can have a viscosity ranging up to 1, 1.1, 1.2, 1.3, 1.4, or $1.5 \times 10^6$ (Pa·s) at a shear rate of 0.1 rad/s. In some embodiments, highly filled hardenable (e.g. dental) composition can have a viscosity ranging up to 2, 2.1, 2.2, 2.3, 2.4, or $2.5 \times 10^5$ (Pa·s) at a shear rate of 1 rad/s. In some embodiments, highly filled hardenable (e.g. dental) composition can have a viscosity ranging up to 20,000; 30,000; 40,000 or 50,000 (Pa·s) at a shear rate of 10 rad/s.

In some embodiments, the curable dental compositions described herein are provided in a (e.g. pre-filled) dispensing device. Various dispensing device suitable for storing and applying hardenable (e.g. dental) compositions are known such as described in U.S. Pat. Nos. 4,632,672; 5,100,320; and 5,848,894; incorporated herein by reference. Such device generally comprises a cartridge or syringe, a dispensing nozzle comprising an outlet at one end of the cartridge; and a plunger at the opposing end of the cartridge.

In some embodiments, the cartridge has two chambers for containing separate parts of a two-part composition.

FIG. 1 shows an illustrative syringe device 1 suitable for dispensing a two-part (e.g. dental sealant) material. The syringe device comprises a (e.g. cylindrical) cartridge 10, a plunger 20 and a dispensing nozzle 17.

The cartridge 10 typically has a cylindrical outer shape. In typical embodiments, the cartridge further comprises a finger plate 113. The shape of the finger plate 113 includes flats or supporting points that hinder the cartridge 10 from rolling over when placed on a flat surface. Thus, when the syringe 1 is placed on a flat surface such as a table, the flats of the finger plate 113 of the cartridge 10 can prevent the syringe from rolling off the table.

The cartridge 10 of the syringe 1 is pre-filled with a two-component composition. One part of the two-part composition is contained within a first chamber 111 and the second part of the two-part composition is contained within a second chamber 112.

Figure 2:
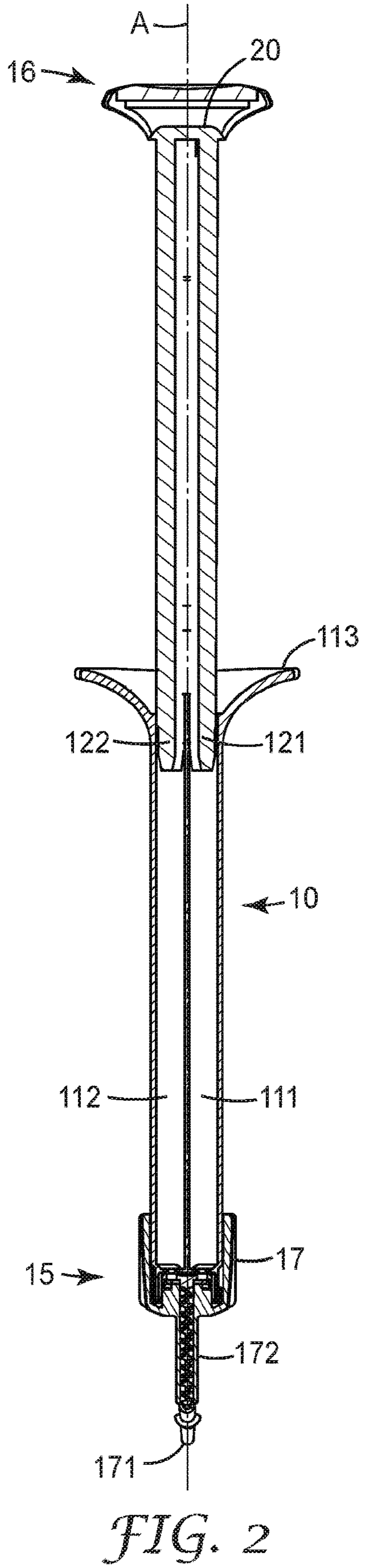
FIG. 2 is a cross-sectional view of an illustrative syringe.

As best shown in the cross-sectional view of FIG. 2, the syringe 1 has a plunger 20 that comprises a first plunger rod 121 and a second plunger rod 122. One end of each rod 121, 122 is configured to seal the first and second part of the composition within the chambers 111 and 112. The opposing ends of the plunger rods are connected at the back end 16 of plunger 20.

The cartridge contains a sufficient amount of two-component composition for sealing one or more teeth. Typically, the amount of two-component composition is sufficient for sealing all the teeth of a single patient. In some embodiments, the amount of two-component composition is sufficient for sealing all the teeth of more than one patient and the removable nozzle is replaced between patients. In typical embodiments, the syringe is pre-filled with the two-part composition by the manufacturer. In some embodiments, the (e.g. pre-filled) syringe, two-part composition, and one or more removable dispensing nozzles are bundled as a kit for storing and applying composition. The kit typically further comprises instructions for utilizing the kit and attaching the removable nozzle onto the syringe.

To facilitate use in the mouth and to minimize waste of the composition, in some embodiments the syringe device is relatively small. In some embodiments, the total length of the filled syringe (without the nozzle) and prior to engaging the plunger, as shown in FIGS. 1 and 2. is no greater 200 mm, 190 mm, 180 mm, 170 mm, 160 mm, 150 mm or 140 mm. The total length of the filled syringe (without the nozzle) is typically at least 100 mm, 110 mm, 120 mm, or 130 mm. In some embodiments, the total length of the cartridge is typically no greater than 100 mm, 95 mm, 90 mm, 85 mm, 80 mm, or 75 mm. The total length of the cartridge is typically at least 50 mm, 55 mm, 60 mm, or 65 mm. The length of the interior chambers is less than the total length of the cartridge. In some embodiments, the total length of the interior chamber is no greater than 70 mm or 65 mm. The exterior diameter of the cartridge is typically no greater than 15 mm, 14 mm, 13 mm, 12 mm, 11 mm, 10 mm, 9 mm, or 8 mm. The exterior diameter is typically at least 5 mm, 5.5 mm, 6 mm, 6.5 mm, 7 mm or 7.5 mm. The total interior volume of the cartridge is typically no greater than 5, 4.5, 4, 3.5, 3, or 2.5 cc.

In typical embodiment, the first chamber and second chamber have a volume ratio of about 1:1. Other volume ratios could be employed. For example, the volume ratio of the chamber may range from 1:1 to about 2:1 or 3:1.

When the first and second part are intended to be mixed a volume ratio of 1:1, the first and second chamber contain about half the total volume of the cartridge. Thus, in the case of the small syringe device described above, the total interior volume of each chamber is typically no greater than 2.5, 2, 1.75, 1.5, or 1.25 cc.

Figure 3:
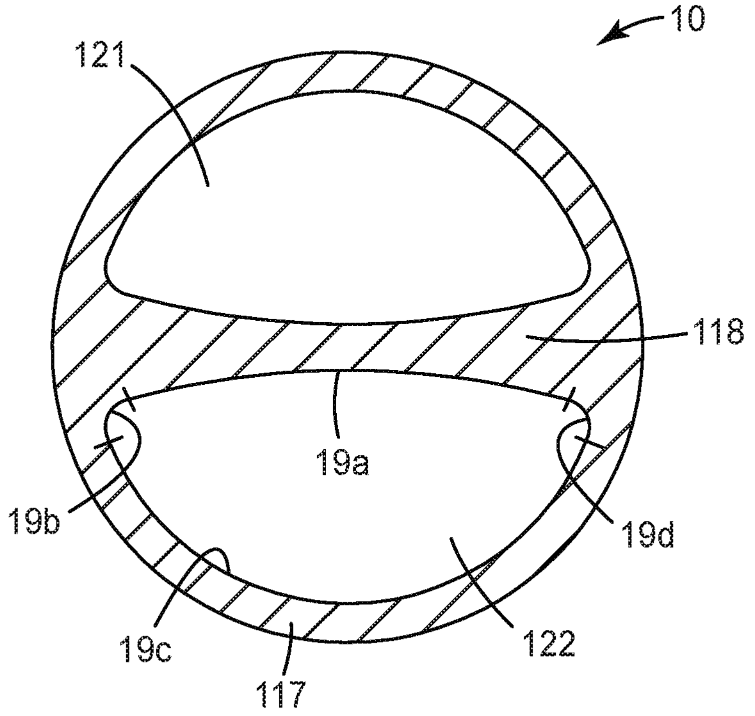
FIG. 3 is a cross-sectional view of an illustrative syringe.

FIG. 3 shows a cross-sectional view of the syringe 1 through the cartridge 10. The cartridge 10 has two chambers 111, 112 that extend through the cartridge 10. In some embodiments, the chambers have a substantially D-shaped cross-section, such as described in U.S. Patent Publication No. 2016/0270879; incorporated herein by reference.

In particular the perimeter of the D-shape is defined by a plurality of circle segments 19*a*, 19*b*, 19*c* and 19*d* only. (Circle segments 19*a*, 19*b*, 19*c* and 19*d* correspond to the first, third, second and forth circle segment, respectively.) The circle segment 19*a* adjacent the separation wall is based on a different radius than the opposite circle segment 19*c* adjacent the outer wall 17. In particular the circle segment 19*a* is based on a larger radius than the circle segment 19*c*. Thus, on the one hand, a substantial D-shape is achieved but, on the having a cross-section based on only circular structures allows more reliable sealing compared to a cross-section having one or more straight structures. Further the circle segments 19*a*, 19*b*, 19*c* and 19*d* join in a manner such that at the joint of two circle segments respective tangents through that joint on each circle segment coincide. Or in other words the circle segments 19*a*, 19*b*, 19*c* and 19*d* smoothly merge into one another and together form a closed line defining the perimeter of the cross-section.

In a preferred embodiment the radius of the first circle segment may range from 10 mm to 20, 30, 40, or 50 mm; the radius of the second circle segment may range from 2 mm to 5, 10, 15 or 20 mm; and the radius of the third and fourth circle segment may range from 0.3 mm to 1, 2, or 3 mm. In one embodiment, radius 19*a* is about 14 mm, radius 19*b* is about 1 mm and radius 19*c*, is about 4 mm.

As shown the two substantial D-shapes are arranged in a mirrored fashion relative to each other so that the cartridge 10 has, on the one end, a generally cylindrical outer shape, and on the other end forms an outer wall 117 with a separation wall 118 having a substantially uniform wall thickness. The substantially uniform wall thickness facilitates for example manufacturing of the cartridge by injection molding (e.g. of polypropylene).

In some embodiments, each of the plunger rods 121 and 122 are configured for press-fitting into a respective chamber of the cartridge. The plunger rods may comprise a more rigid material than the cartridge. In some embodiments, the plunger rods are injection molded from polypropylene containing 50% glass fibers. The cross-sectional shape of each plunger rod typically corresponds to the cross-sectional shape of the respective chamber. Thus, when the chambers have a substantially D-shaped cross-section, the plunger rods also have a substantially D-shaped cross-section.

In some embodiments, the end portion of the plunger rods 121 and 122 that seal the two-part composition within the chambers are preferably oversized, in particular two-dimensionally enlarged by an offset, relative to the cross-sectional shape of the respective chamber. In one embodiment, each plunger rod 121 and 122 has a skirt-type lip seal, as described in greater detail in previously cited U.S. patent Publication No. US2016/0270879.

The chambers and plunger rods can have various other designs and cross-sectional shapes such that the two-component composition is sealed within the respective chambers prior to use.

The dispensing nozzle 17 removably attaches to a front end 15 of the cartridge 10. In some embodiments, the nozzle rotatably attaches to the front end of the cartridge 10. The cartridge, nozzle, or combination thereof comprises a valve that can provide or prevent fluid communication between the two-part composition of the cartridge 10 and the dispensing nozzle 17. In some embodiments, the cartridge 10 and the nozzle 17 in combination form a rotary slide valve. Further details concerning valves are described in WO2018/057503 and U.S. Pat. No. 9,427,290; incorporated herein by reference.

Figure 4:
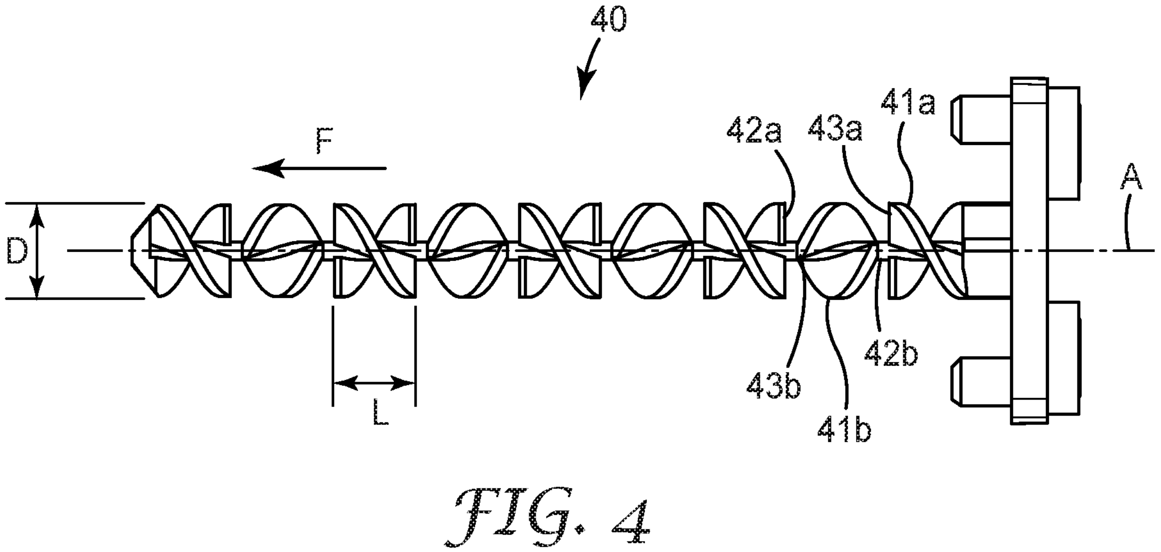
FIG. 4 is a side view of an illustrative static mixer.

The dispensing nozzle 17 further comprises a cannula 172 including a static mixer 40 (not shown in FIG. 1, but depicted in FIG. 2 and FIG. 4).

The volume and design can be chosen to maximize mixing and reduce waste. In some embodiments, the total volume of the dispensing nozzle, in the absence of the static mixer, is typically no greater than 0.25, 0.20, 0.15, or 0.10 cc. In some embodiments, the total volume of the dispensing nozzle is no greater than 0.09, 0.08, 0.07, 0.06, 0.05, 0.04, or 0.03 cc. The cannula has an exterior a width of 2, 2.5 or 3 mm and a length of about 75 to 150 mm.

Various static mixers can be utilized. FIG. 4 shows a preferred static mixer 40 that may be arranged within the dispensing nozzle illustrated in FIG. 1 and FIG. 2. Such a static mixer is described in WO2015/205181; incorporated herein by reference. The static mixer 40 has a cascade of mixing elements 41*a*/41*b*. Each mixing element 41*a*/41*b* is based on a helical shape or a helicoid. The structure of such a helical mixing element can be basically imagined as a planar sheet of material which, held at opposite ends, is twisted or wound by 180 degrees, although other methods (for example injection molding) are typically used to manufacture such a structure. The overall outer shape of such a mixing element 41*a*/41*b* is based on a cylindrical helix. Therefore. each mixing element has an outer diameter D. Each mixing element has an entry edge 42*a*/42*b* for the material and an exit edge 43*a*/43*b*. With respect to a flow F of the dental material through the mixing unit the material enters each mixing element 41*a*/41*b* at the entry edge 42*a*/42*b* and exits each mixing element 41*a*/41*b* at the exit edge 43*a*/43*b*. The static mixer 40 has a plurality of mixing elements 41*a*/41*b* arranged in sequence. The entry and exit edges 42*a*/42*b*, 43*a*/43*b* of two adjacent mixing elements 41*a*/41*b* are angularly offset relative to each other. Therefore, the flow of the two components of the dental material is divided and partial divisional streams thereof merged multiple times as the dental material flows through the mixing unit 40. Thus, the (e.g. two parts of the) dental material is mixed. The angle of the offset between the entry and exit edges 42*a*/42*b*, 43*a*/43*b* is measured in a plane perpendicular to a longitudinal axis A of the mixing unit and on a point on that longitudinal axis A. The angle of the offset between the entry and exit edges 42*a*/42*b*, 43*a*/43*b* in the example is 90 degrees. In other words, the entry and exit edges 42*a*/42*b*, 43*a*/43*b* of adjacent mixing elements 41*a*/41*b* are arranged crosswise relative to each other.

As shown, the mixing unit 40 has right handed mixing elements 41*a* and left handed mixing elements 41*b* which are consecutively arranged in an alternate order along the longitudinal axis A. The right and left handed mixing elements 41, 41*b* differ in the winding direction of the helix on which mixing element 41*a*/41*b* is based.

In some embodiments, the mixing elements 41*a*/41*b* of the small syringe device have an outer diameter D of between 1.5 mm and 1.6 mm. Further, each mixing element has a length L of between 0.6 mm and 1.2 mm, preferably 0.78 mm. The diameter D as well as the Length L is preferably the same for all mixing elements 41*a*/41*b* of the mixing unit 40. The specific range of the diameter D of the mixing elements 41*a*/41*b* can provide improved mixing.

The dispensing nozzle tip 173 of the dispensing nozzle can be rigid or flexible. It can be formed of a thermoplastic material or may be a metal hollow needle. In some embodiments, the tip of the dispensing nozzle is angular, extending from the cannula at an interior included angle ranging from 90° to 180°. In some embodiments, the interior included angle is at least 95, 100, 105 or 110°. In some embodiments, the interior included angle is no greater than 170, 160, 150, 140, or 130°. In some embodiments, the length of the tip of the small syringe device can range from about 5 mm to 15 mm or 20 mm. In some embodiments, the length of the tip is no greater than 14, 13, 12, 11, or 10 mm. The outlet 171 is typically round, having a diameter narrower than the cannula. In some embodiments, the diameter of the outlet 171 is at least 0.5, 0.6, 0.7, or 0.8 mm ranging up to 1, 1.1, 1.2, 1.3, 1.4 or 1.5 mm.

The syringe 1 may optionally include an actuator for stepwise engaging the plunger toward a front end of the syringe. Inclusion of an actuator is useful for dispensing a pre-determined amount (e.g. a single dose) of the composition material. This feature can be useful for applying precisely the correct amount, i.e. a sufficient amount to fill the pits and fissures; yet not an excessive amount such that the presence of the cured sealant can be detected by a patient during chewing. One example of a syringe with an actuator is further described in WO2017/180545; incorporated herein by reference.

During use of the syringe device the nozzle is turned such that the slide valve is open and the fluid contained within the chambers can be conveyed through the nozzle. The (e.g. index and middle) fingers contact the finger plate 113 and the thumb typically presses on the back end 16 of the plunger causing the first plunger rod 121 and a second plunger rod 122 to move towards the front end 15 of the syringe device. Such movement causes the first and second part to be conveyed through the static mixer and outlet onto the enamel of a tooth surface.

In some embodiments, the two components are combined with each other by merging in a static mixer. In the case of the previously described small syringe device, each of the components preferably has a viscosity no greater than 6,500; 6,000; 5,500; or 5,000 cps at 23° C. when measured according to the test method described in the examples. In some embodiments, the viscosity of each of the components is no greater than 4,500; 4,000; 3,500; or 3,000 eps at 23° C. The viscosity of each of the components is typically at least 200, 300, 400 or 500 cps at 23° C.

Further, the viscosities of the two components are typically similar, for example differ by no more than 85, 80, 75, 70, 65, 60, 55, 50, 45, 40, 35, 30, 25, 20, 15, or 10% of the higher viscosity material. When the viscosity of each components to be mixed and the difference in viscosity is within a suitable range, a sufficiently uniform mixture can be dispensed through the outlet. Further, the components can be conveyed through the static mixer at relatively low extrusion forces. Such low extrusion forces can be typically generated by a manually operated system.

As used herein "dental article" refers to an article that can be adhered (e.g., bonded) to a tooth structure or dental implant. Dental articles include, for example, crowns, bridges, veneers, inlays, onlays, fillings, orthodontic appliances and devices.

"orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

"oral surface" refers to a soft or hard surface in the oral environment. Hard surfaces typically include tooth structure including, for example, natural and artificial tooth surfaces, bone, and the like.

"hardenable" and "curable' is descriptive of a material or composition that can be cured (e.g., polymerized or crosslinked) by heating to induce polymerization and/or crosslinking; irradiating with actinic irradiation to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

"hardened" refers to a material or composition that has been cured (e.g., polymerized or crosslinked).

"hardener" refers to something that initiates hardening of a resin. A hardener may include, for example, a polymerization initiator system, a photoinitiator system, a thermal initiator and/or a redox initiator system.

"(meth)acrylate" is a shorthand reference to acrylate, methacrylate, or combinations thereof, "(meth)acrylic" is a shorthand reference to acrylic, methacrylic, or combinations thereof, and "(meth)acryl" is a shorthand reference to acryl, methacryl, or combinations thereof.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

Illustrative Embodiments:

1. A two part hardenable dental composition comprising:
   a first part comprising a composition comprising a liquid material and an encapsulated material wherein the encapsulated material comprises a basic core material and an inorganic shell material comprising a metal oxide surrounding the core; and a second part comprising a composition comprising a liquid material;
   wherein the composition of the first part has a first viscosity, the composition of the second part has a second viscosity; and the difference in first and second viscosity as determined with a Brookfield viscometer and type-A T-bar spindle at 23° C. and shear rate of 100 $s^{-1}$ is no greater than 85, 80, 75, 70, 65, 60, 55, 50, 45, 40, 35, 30, 25, 20, 15, or 10% of the higher viscosity composition.
2. A two-part hardenable dental composition comprising:
   a first part comprising a composition having a viscosity as determined with a Brookfield viscometer and type-A T-bar spindle at 23° C. and shear rate of 100 $s^{-1}$ is no greater than 6500 cps comprising a liquid material and an encapsulated material wherein the encapsulated material comprises a basic core material and an inorganic shell material comprising a metal oxide surrounding the core; and
   a second part comprising a composition having a viscosity no greater than 6500 cps comprising a liquid material.
3. A hardenable dental composition comprising:
   a one part composition comprising a liquid material and an encapsulated material wherein the encapsulated material comprises a basic core material and an inorganic shell material comprising a metal oxide surrounding the core; wherein the one part composition has a viscosity of less than 25,000 cps as determined with a Brookfield viscometer and type-A T-bar spindle at 23° C. and shear rate of 100 $s^{-1}$
   or has a viscosity greater than 40,000 cps.
4. A two part hardenable dental composition comprising:
   a first part comprising an encapsulated material wherein the encapsulated material comprises a basic core material and an inorganic shell material comprising a metal oxide surrounding the core;
   a non-aqueous second part; and
   a redox curing system.
5. The two part hardenable dental composition of embodiment 4 wherein the second part comprise a polymerizable resin.
6. A two part hardenable dental composition comprising:
   a first part comprising an encapsulated material wherein the encapsulated material comprises a basic core material and an inorganic shell material comprising a metal oxide surrounding the core and a reducing agent;
   a second part comprising an oxidizing agent selected from peroxide compounds, persulfate compounds, perborate compounds, and perchlorate compounds.
7. The dental composition of embodiments 1, 2, 4, or 6 wherein upon combining the first and second part, the composition initially has an acidic or neutral pH.
8. The dental composition of previous embodiments wherein the shell is degradable by the second part.
9. The dental composition of previous embodiments wherein the basic core material releases —OH upon degradation of the shell.
10. The dental composition of previous embodiments wherein the basic core material comprises a component having a pKa ranging from 8-14.
11. The dental composition of previous embodiments wherein the basic core material comprises a component having a pKa ranging from 11-14.
12. The dental composition of previous claims wherein the basic core material comprises a material that releases calcium ions.
13. The dental composition of previous embodiments wherein the basic core material comprises at least 25, 30, 35, 40, or 45 wt.-% of components(s) having a pKa ranging from 11-14.
14. The dental composition of the previous embodiments wherein the shell is a continuous film having a thickness less than 500 nm.
15. The dental composition of previous embodiments wherein the inorganic shell material is less basic than the basic core material.

16. The dental composition of previous claims wherein the inorganic shell material comprises a metal oxide having a pKa of 6-8.

17. The dental composition of previous embodiments wherein when 0.25 grams of the encapsulated material is combined with 25 g of deionized water, a pH of at least 8.5 or 9 is obtained within 24 hours.

18. The dental composition of previous embodiments wherein when 0.25 grams of the encapsulated material is combined with a solution of 15 g of deionized water and 10 g of an aqueous potassium acid phthalate buffer solution adjusted to a pH of 4.00 at 25° C. with hydrochloric acid, a pH of at least 8.5 or 9 is obtained within 24 hours.

19. The dental composition of previous embodiments wherein the basic core material is hardenable.

20. The dental composition of embodiment 19 wherein the basic core material comprises calcium silicate.

21. The dental composition of previous embodiments wherein the basic core material is a dental filler comprising neutral metal oxide(s) that have low solubility in the second part.

22. The dental composition of previous embodiments wherein the hardenable dental composition comprise a material that promotes remineralization by release of calcium ions, phosphorus ion, fluorine ions, or a combination thereof.

23. The dental composition of embodiments 1-21 wherein the composition further comprises at least one second filler.

24. The dental composition of embodiment 23 wherein the second filler comprises nanoscopic particulate filler.

25. The dental composition of embodiment 24 wherein the second filler comprises zirconia, silica, or mixture thereof.

26. The dental composition of claims 24-25 wherein the second filler comprise a nanocluster filler.

27. The dental composition of embodiments 1-26 wherein the liquid material of first and/or second part comprises water, acid, a polymerizable material, or a combination thereof.

28. The dental composition of embodiment 27 wherein the polymerizable material comprises a hydroxy functional (meth)acrylate monomer, an acidic polymer, or a combination thereof.

29. The dental composition of previous embodiments wherein the cured dental composition provides a pH of at least 8.5 or 9 within 500 hours according to the disk buffer test.

30. The dental composition of previous embodiments wherein the average cell proliferation of pulp cells is at least 75% of a control sample when in contact with the cured dental composition.

31. The dental composition of previous embodiments wherein the average alkaline phosphatase (ALP) activity of pulp cells increases when in contact with the cured dental composition.

32. An encapsulated material suitable for use in a biological carrier material comprising a basic core material and an inorganic shell material comprising a metal oxide surrounding the core.

33. The encapsulated material of embodiment 32 wherein the encapsulated material is further characterized by any one or combination of claims 9-21.

34. The encapsulated core material of embodiments 32-33 wherein the composition is curable or self-setting when mixed with water 35. A hardenable composition comprising an encapsulated material for use in a biological carrier material comprising a basic core material and an inorganic shell material comprising a metal oxide surrounding the core; wherein the hardenable composition is characterized according to claims 1-6.

36. The hardenable dental composition of embodiment 35 wherein the composition is a dental or medical composition.

37. The hardenable composition of embodiments 32-36 wherein the hardenable composition further comprises a second filler and/or a polymerizable material according to any one or combination of claims 23-28.

38. The hardenable composition of embodiments 34-37 wherein the hardenable composition contacts water or an acidic component during use.

39. The hardenable composition of embodiment 38 wherein the water or acidic component is a biological fluid.

40. A method of delaying release of a basic core material comprising:
- providing a composition according to embodiments 1-39; and
- applying the composition to a tooth or bone structure.

41. A method of providing a delayed increase in basicity comprising:
- providing the composition according to embodiments 1-39; and
- applying the composition to a tooth or bone structure.

42. A method of promoting remineralization comprising:
- providing the composition according to embodiments 1-39 wherein the basic core further comprises a material that promotes remineralization by the release of calcium ions, phosphorous containing ions, fluoride ions, or a combination thereof, and
- applying the composition to a tooth or bone structure.

43. The method of embodiment 40 wherein the material that promotes remineralization release calcium ions, phosphorous containing ions, fluoride ions, or a combination thereof.

44. A method of increasing the average alkaline phosphatase (ALP) activity of pulp cells comprising
- providing the composition according to embodiments 1-37 wherein the basic core further comprises a material that promotes remineralization; and
- applying the composition to a tooth or bone structure.

45. A composition according to embodiments 1-39 for use for applying to a tooth or bone
- structure wherein the composition
- provides a delayed release of a basic core material;
- provides a delayed increase in basicity;
- promotes remineralization;
- increases the average alkaline phosphatase (ALP) activity of pulp cells;

or a combination thereof.

46. A method of use of a composition comprising
- providing a composition according to embodiments 1-39;
- applying the composition to a tooth or bone structure.

47. The method of embodiment 46 wherein the composition comprises a polymerizable material and the method further comprises hardening by exposing the composition to a radiation source.

48. The method of embodiments 46-47 wherein the composition provides a delayed release of a basic core material.

49. The method of embodiments 46-48 wherein the composition provides a delayed increase in basicity.

50. The method of embodiments 46-49 wherein the composition promotes remineralization of a tooth or bone structure.

51. The method of embodiments 46-50 wherein the composition increases the average alkaline phosphatase (ALP) activity of pulp cells;

52. The method of embodiments 46-51 wherein the composition is a dental adhesive or cement used to bond a dental article to a tooth structure.
53. The method of embodiments 46-51 wherein the composition is a dental restorative.
54. A dispensing device comprising a hardenable composition comprising:
   a liquid material and an encapsulated material wherein the encapsulated material comprises a basic core material and an inorganic shell material comprising a metal oxide surrounding the core.
55. The dispensing device of embodiment 54 wherein the liquid material comprises a polymerizable resin.
56. The dispensing device of embodiments 54-55 wherein the composition has a viscosity ranging from 200 cps to 100,000 cps at 23° C.
57. The dispensing device of embodiments 54-56 wherein the device comprises
   a cartridge,
   a nozzle comprising an outlet at one end of the cartridge; and
   a plunger at the opposing end of the cartridge for dispensing the hardenable composition from the cartridge.
58. The dispensing device of embodiment 57 wherein the hardenable composition is a two-part composition and the cartridge has two chambers.
59. The dispensing device of embodiments 54-58 wherein the dispensing device is a syringe device.
60. The dispensing device of embodiments 54-59 wherein the cartridge includes first and second chambers,
   a dispensing nozzle comprising a static mixer and an outlet at one end of the cartridge; and
   a plunger at the opposing end of the cartridge, wherein the plunger includes two rods wherein one end of the rods seals the first and second part of the composition within the chambers and the opposing ends of the plunger rods are connected.
61. The dispensing device of embodiments 57-60 wherein the cartridge has a volume no greater than 5, 4.5, 4, 3.5, 3, or 2.5 cc.
62. The dispensing device of embodiments 58-61 wherein the first chamber and second chamber have a volume ratio of about 1:1.
63. The dispensing device of embodiments 57-62 wherein the dispensing nozzle has a volume no greater than 0.25, 0.20, 0.15, 0.10 or 0.05 cc.
64. The dispensing device of embodiments 57-62 wherein the outlet has a diameter no greater than 1.5 or 1 mm.
65. The dispensing device of embodiments 57-64 wherein the composition has a viscosity no greater than 5,000 cps at 23 C.
66. A kit comprising
   a hardenable composition comprising a liquid material and an encapsulated material wherein the encapsulated material comprises a basic core material and an inorganic shell material comprising a metal oxide surrounding the core; and
   a dispensing device.
67. The kit of embodiment 66 wherein the dispensing device is pre-filled with the hardenable composition.
68. The kit of claims 66-67 wherein the kit further includes instructions.
69. The kit of embodiments 66-68 wherein the dispensing device is according to claims 54-65.
70. The methods of embodiments 46-53 wherein the dispensing device of claims 54-65 and/or kit of claims 66-69 is utilized to provide the composition according to claims 7-39.

EXAMPLES

Materials

Hydroxyethyl methacrylate (HEMA) was obtained from Evonik Industries, Sarasota, FL.

Ethyl 4-dimethylaminobenzoate (EDMAB) was obtained from the Sigma-Aldrich Corporation, St. Louis, MO.

Camphorquinone (CPQ), Benzoyl peroxide—LUPEROX A75 (BPO), 2-(4-Dimethylamino)phenyl)ethanol (DMAPE), Triethylene glycol dimethacrylate (TEGDMA), and Bisphenol A glyceroate dimethacrylate (BisGMA) were obtained from Sigma-Aldrich. 2,6-Di-tert-butyl-4-methylphenol (BHT) was obtained from PMC Specialties Incorporated, Cincinnati, OH.

Fumed silica (AEROSIL R972) was obtained from Evonik Corporation, Piscataway, NJ.

Fumed silica R812S was obtained from Degussa-Huls Corporation, Parsippany, NJ.

Calcium glycerylphosphate was obtained from Spectrum Laboratory Products, Gardena, CA.

Ytterbium fluoride ($YbF_3$) was obtained from Treibacher Industrie Incorporated, Toronto, Canada.

Buffer BDH5018 (an aqueous potassium acid phthalate buffer adjusted to a pH of 4.00 at 25° C. with hydrochloric acid) obtained from VWR International, Radnor, PA.

VBP polymer was made by reacting PAA:ITA copolymer with sufficient IEM (2-isocyanatoethyl methacrylate) to convert 16 mole percent of the acid groups of the copolymer to pendent methacrylate groups according to the dry polymer preparation of Example 11 of U.S. Pat. No. 5,130,347 (Mitra).

PAA:ITA copolymer was made from a 4:1 mole ratio of acrylic acid:itaconic acid, prepared according to Example 3 of U.S. Pat. No. 5,130,347.

Zr/Si Nanocluster Filler is a silane-treated zirconia/silica nanocluster filler prepared essentially as described in U.S. Pat. No. 6,730,156 [Preparatory Example A (line 51-64) and Example B (column 25 line 65 through column 26 line 40)].

Portland Cement: White Portland Cement (Federal White Type 1, ASTM Designation C150) was purchased from Federal White Cement, Woodstock, Ontario, Canada. The major components of the composition as reported by the manufacturer are tricalcium silicate ($3CaO—SiO_2$), dicalcium silicate ($2CaO—SiO_2$), tricalcium aluminate ($3CaO—Al_2O_3$), tetracalcium aluminoferrite ($4CaO—Al_2O_3—Fe_2O_3$), magnesium oxide, calcium oxide, potassium sulfate, and sodium sulfate. Portland cement is a strongly basic material comprising multiple components. Each major component (excluding the minor components of magnesium oxide, potassium sulfate, and sodium sulfate) contains a significant amount of a strong base (CaO). Portland cement typically contains about 61%-69% CaO, about 18%-24% $SiO_2$, about 2%-6% $Al_2O_3$, about 1%-6% $Fe_2O_3$, about 0.5%-5% MgO.

Bioactive Glass [45S5] was prepared with the following composition: $SiO_2$ (45 wt.-%), $Na_2O$ (24.5 wt.-%), CaO (24.5 wt.-%), $P_2O_5$ (6 wt.-%)]. The bioactive glass is a strongly basic material. It is homogeneous with two strong base components ($Na_2O$ and CaO) that total 49 wt.-% of the composition.

Tricalcium Silicate ($3CaO—SiO_2$) powder was prepared by a sol-gel method. A solution of 0.5 mol $Si(OC_2H_5)_4$ (tetra-ethyl orthosilicate, TEOS), 200 ml water and nitric acid as a catalyst were combined under continuous stirring. 1.5 mol of $Ca(NO_3)_2$-$4H_2$ was then added to the solution. The solution was heated to 60° C. and maintained until gelation occurred. The gel was then dried at 200° C. and calcined at 1500° C. for 6 hours. Tricalcium silicate is a strongly basic, homogeneous compound that has about 74 wt.-% of a strong base component (CaO).

Fluoroaluminosilicate (FAS) Glass was prepared essentially as described in Example 1 of U.S. Pat. No. 5,154,762. The powder ingredients of $SiO_2$ (34.6 wt.-%), $AlF_3$ (21.5 wt.-%), SrO (18.7 wt.-%), $Al_2O_3$ (9.4 wt.-%), $AlPO_4$ (6.5 wt.-%), $Na_2AlF_6$ (5.6 wt.-%), $P_2O_5$ (3.7 wt.-%) were mixed; melted in an arc furnace at 1350-1450° C.; and roller quenched into an amorphous single phase FAS glass. The glass was subsequently ball-milled to provide a pulverized product with a surface area of 2.6 $m^2$/g (measured according to the Brunauer, Emmet, and Teller (BET) method).

BisEMA-6 refers to ethoxylated (6 mole ethylene oxide) bisphenol A dimethacrylate as further described in U.S. Pat. No. 6,030,606, available from Sartomer Co., Inc. (Exton, PA) as "CD541".

BZT refers to 2-(2'-hydroxy-5'-methacryloxyethylphenyl)-2H-benzotriazole, CAS Reg. No. 96478-09-0, available from Ciba, Inc. (Tarrytown, NY) as "TINUVIN R 796", also available from Sigma-Aldrich Corp. (St. Louis, MO).

DPIHFP or DPIPF6 refers to diphenyliodonium hexafluorophosphate, CAS Reg. No. 58109-40-3, available from Johnson Matthey, Alfa Aesar Division (Ward Hill, MA).

ENMAP refers to ethyl N-methyl-N-phenyl-3-aminopropionate (also referred to as N-methyl-N-phenyl-beta-alanine ethyl ester), CAS Reg. No. 2003-76-1, which can be prepared by known methods, such as those described by Adamson, et al.; JCSOA9; J. Chem. Soc.; 1949; spl. 144-152; also available from Johnson Matthey, Alfa Aesar Division (Ward Hill, MA).

IRGACURE 819 refers to a bis(2,4,6-trimethylbenzoyl) phenylphosphine oxide photoinitiator. CAS Reg. No. 162881-26-7, available from Ciba Specialty Chemicals Corp. (Tarrytown, NY), also available from Sigma-Aldrich Corp. (St. Louis, MO).

PEG600 DM refers to poly(ethylene glycol) dimethacrylate, average MW ~600, available from Sartomer Co., Inc. (Exton, PA).

UDMA refers to diurethane dimethacrylate, CAS Reg. No. 72869-86-4, available under the trade designation "ROHAMERE 6661-0" from Rohm America LLC (Piscataway, NJ); also available from Dajac Laboratories (Trevose, PA).

S/T Silica/Zirconia Nanoclusters refers to silane-treated silica-zirconia nanocluster filler, prepared essentially as described in U.S. Pat. No. 6,730,156 at column 25, lines 50-63 (Preparatory Example A) and at column 25, line 64 through column 26, line 40 (Preparatory Example B) with minor modifications, including performing the silanization in 1-methoxy-2-propanol (rather than water) adjusted to a pH of about 8.8 with $NH_4OH$ (rather than to a pH of 3-3.3 with trifluoroacetic acid), and obtaining the S/T Silica/Zirconia Clusters by gap drying (rather than spray drying).

S/T 20 nm Silica Nanoparticle refers to silane-treated silica nanoparticle filler having a nominal particle size of approximately 20 nanometers, prepared essentially as described in U.S. Pat. No. 6,572,693 at column 21, lines 63-67 (Nanosized particle filler, Type #2);

S/T Nanozirconia Nanoparticle refers to silane-treated zirconia nanoparticle filler, which can be prepared from the zirconia sol as generally described in U.S. Pat. No. 8,647,510 at column 36 line 61 to column 37 line 16 (Example 11A-IER). The zirconia sol is added to an equivalent weight of 1-methoxy-2-propanol containing 3-methacryloxypropyltrimethoxysilane (1.1 mmol of 3-methacryloxypropyltrimethoxysilane per gram of nanozirconia to be surface treated). The mixture is heated to about 85° C. for 3 hours with stirring. The mixture is cooled to 35° C., adjusted to a pH of about 9.5 with $NH_4OH$, and the mixture reheated to about 85° C. for 4 hours with stirring. The resultant S/T Nanozirconia is isolated by removing solvents via gap drying. S/T Nanozirconia may also be prepared as described in U.S. Pat. No. 7,649,029 beginning at column 19, line 39 through column 20, line 41 (Filler I), except for the substitution of 3-methacryloxypropyltrimethoxysilane for the blend of Silquest A-174 and A-1230, and further removing the solvents via gap drying.

Calculations

The following equations 1-6 were used to calculate the shell thickness, wt.-% of core material, and wt.-% shell material for the Encapsulated Materials prepared by the processes described in Examples 1-5, 26, and 28-29. In the calculations, the total surface area of the core material was determined by representing the particles of the core material powder as spheres (surface area=$4\pi(d/2)^2$, volume=$(4/3)(\pi)(d/2)^3$.

$$ST_{em}=\frac{V_{mo}}{SA_c}$$ Equation 1:

$ST_{em}$(cm)=Shell Thickness of Encapsulated Material.

$V_{mo}$ ($cm^3$)=Volume of Metal Oxide a prepared by APCVD process.

$SA_c$ ($cm^2$)=Total Surface Area of Core Material Powder.

$$V_{mo}=\frac{FR_{cg}*CT*MW_{mo}*CA*\%P*EDE}{1000\left(\frac{cm^3}{L}\right)*22.4\left(\frac{L}{mol}\right)*D_{mo}}$$ Equation 2

$FR_{cg}$ ($cm^3$/min)=Flow Rate of Carrier Gas (for $Al_2Me_6$, $TiCl_4$, $SiCl_4$).

CT (min)=Coating Time.

CA=Cations per Mole of Precursor Material.

$MW_{mo}$ (g/mol)=Molecular Weight of Metal Oxide per Mole of Cation (for $Al_2O_3$ $MW_{mo}$=51 g/mol, for $TiO_2$ $MW_{mo}$=80 g/mol, for $SiO_2$ $MW_{mo}$=60 g/mol).

$D_{mo}$ (g/$cm^3$)=Density of Metal Oxide (for $Al_2O_3$ $D_{mo}$=3.0, for $TiO_2$ $D_{mo}$=3.0, for $SiO_2$ $D_{mo}$=2.2).

% P=the molar percentage of metal oxide precursor contained in the carrier gas (% P for $Al_2Me_6$=1.33%, % P for $TiCl_4$=1.33%, % P for $SiCl_4$=35.7%).

EDE=Estimated Deposition Efficiency of the APCVD process used in the examples (EDE for $Al_2O_3$=0.5, EDE for $TiO_2$=0.6, EDE for $SiO_2$=0.4).

$$SA_c=N_{cp}*4\pi\left(\frac{d}{2}\right)^2$$ Equation 3

$N_{cp}$=Number of Core Material Powder Particles.

$$N_{cp}=\frac{M_{cp}}{D_{cp}*\frac{4}{3}\pi\left(\frac{d}{2}\right)^3}$$ Equation 4

Mcp (g)=Amount of Core Powder Material used in APCVD process (bioactive glass, Portland cement, tricalcium silicate).

Msm (g)=Amount of Metal Oxide deposited by APCVD process ($Al_2O_3$, $TiO_2$, $SiO_2$).

Msm (g)=$V_{mo}$*$D_{mo}$ $D_{cp}$ (g/$cm^3$)=Density of Core Powder Material (for bioactive glass Dcp=2.65, for Portland cement Dcp=3.11).

d (cm)=Diameter of Core Particle.

Equations 5 and 6—Weight Percentages (wt.-%) of Encapsulated Materials:

$$\text{weight percent Shell} = 100 * \frac{Msm(g)}{[Msm(g) + Mcp(g)]}$$

weight percent Core=(100–weight percent Shell).

For Encapsulated Materials with a tricalcium silicate core, the core particles had additional porosity that affected the apparent surface area determination. For tricalcium silicate Encapsulated Materials, an indirect method was used to estimate the effective surface area of the core and the thickness of the shell coating. Tricalcium silicate Encapsulated Materials and Portland cement Encapsulated Materials (with the same shell material) that had about the same time required to change pH of a buffer solution from 4 to 9 (according to the procedure of Examples 6-9) were estimated to have the same shell thickness. Thus, the shell thickness of the tricalcium silicate Encapsulated Material was based on the value calculated for the corresponding Portland cement Encapsulated Material.

Measurements

Unless otherwise noted, viscosity measurements were determined using a Brookfield DV-I+ Viscometer with a HELIPATH stand and type-A T-bar spindle (AMETEK Brookfield, Middleboro, MA). The measurements were performed at 23° C. and shear rate of 100 $s^{-1}$. Test results were obtained when the viscosity measurement stabilized (typically within 0.5-2 minutes). Viscosities are reported in centipoise (cP).

Example 1. Encapsulated Materials with Bioactive Glass Cores

Bioactive glass (BG) powder was encapsulated with an aluminum oxide (AO) based material using atmospheric pressure chemical vapor deposition (APCVD). The bioactive glass was coated by reacting trimethyl aluminum (obtained from Strem Chemicals, Newburyport, MA and dispensed from a stainless steel bubbler) with water vapor in a fluidized bed reactor. The reactor was a glass frit funnel tube (2 cm diameter, 18 cm height). The reactor had an extended inlet tube from below the frit routed parallel to the body of the reactor, and an extended top area above the frit to allow the desired reactor height and fittings for a precursor injector tube and an exhaust outlet. Temperature was controlled at 180° C. using an oil bath. Nitrogen carrier gas was used with standard bubbler configurations for liquid precursors. The bubblers were maintained at an ambient temperature of about 22° C. Flow rates through the trimethyl aluminum (TMA) bubbler ranged from 100-330 $cm^3$/minute. Flow rates through the water bubbler ranged from (250-1250 $cm^3$/minute). The total coating time ranged from 20-100 minutes. Encapsulated Materials A-J were prepared by varying the following parameters: amount of bioactive glass added, particle size of the bioactive glass powder, the TMA flow rate, the water flow rate, and coating time. In Table 1, the encapsulation parameters are listed for Encapsulated Materials A-J. For Encapsulated Materials G-J a larger reactor was used (4 cm diameter, 30 cm height). For Encapsulated Materials A-C, and G-J, prior to adding to the reactor, the particle size of the bioactive glass powder was selected by passing the powder through a 45 micron sieve and collecting on a 38 micron sieve. For Encapsulated Materials D-F, prior to adding to the reactor, the bioactive glass powder was milled using a ball mill with 5 mm media to achieve a 10 micron particle size. The mean particle size of each powder after milling was determined using a Model LA950 Laser Particle Size Analyzer (Horiba Scientific, Edison, NJ) with water.

In Table 1a, the calculated values of shell thickness (nanometers), wt.-% of the core, and wt.-% of the shell for each Encapsulated Material A-J are reported.

TABLE 1

Encapsulated Bioactive Glasses Using APCVD Process

| Encapsulated Material | Amount of Bioactive Glass Added (g) | Bioactive Glass Particle Size (microns) | TMA Flow Rate ($cm^3$/min) | Water Flow Rate ($cm^3$/min) | Coating Time (minutes) |
|---|---|---|---|---|---|
| A | 10 | 38-45 | 100 | 1250 | 20 |
| B | 8 | 38-45 | 100 | 1250 | 40 |
| C | 6 | 38-45 | 100 | 1250 | 60 |
| D | 6 | 10 | 100 | 250 | 45 |
| E | 3 | 10 | 100 | 250 | 70 |
| F | 3 | 10 | 100 | 250 | 100 |
| G | 20 | 38-45 | 220 | 550 | 60 |
| H | 20 | 38-45 | 220 | 550 | 45 |
| I | 20 | 38-45 | 220 | 550 | 30 |
| J | 40 | 38-45 | 330 | 833 | 80 |

TABLE 1a

Encapsulated Bioactive Glass Materials

| Encapsulated Material | Shell Thickness (nm) | wt.-% of Core | wt.-% of Shell |
|---|---|---|---|
| A | 37 | 99.5 | 0.5 |
| B | 94 | 98.5 | 1.5 |
| C | 187 | 97 | 3 |
| D | 33 | 98 | 2 |
| E | 104 | 94 | 6 |
| F | 149 | 91 | 9 |
| G | 124 | 98 | 2 |
| H | 93 | 98.5 | 1.5 |
| I | 62 | 99 | 1 |
| J | 124 | 98 | 2 |

Example 2. Encapsulated Materials with Tricalcium Silicate Cores

Tricalcium silicate (TCS) was encapsulated with an aluminum oxide based material using atmospheric pressure chemical vapor deposition (APCVD). The tricalcium silicate powder (30 g) was coated by reacting trimethyl aluminum (obtained from Strem Chemicals and dispensed from a stainless steel bubbler) with water vapor in a fluidized bed reactor. The reactor was a glass frit funnel tube (4 cm diameter, 30 cm height). The reactor had an extended inlet tube from below the frit routed parallel to the body of the reactor, and an extended top area above the frit to allow the desired reactor height and fittings for a precursor injector tube and an exhaust outlet. Temperature was controlled at 180° C. using an oil bath. Nitrogen carrier gas was used with standard bubbler configurations for liquid precursors. The bubblers were maintained at an ambient temperature of about 22° C. The flow rate through the trimethyl aluminum (TMA) bubbler was 500 $cm^3$/minute. The flow rate through the water bubbler was 1750 $cm^3$/minute. The total coating time was 40 minutes. In Table 2, the mean particle size of the tricalcium silicate powder added to the reactor and the other encapsulation parameters are listed. Following the coating procedure, the resulting encapsulated materials were individually sieved to collect encapsulated material having a particle size of less than 38 microns. These sieved encapsulated materials were designated as Encapsulated Materials K and L.

In Table 2a, the calculated values of shell thickness (nanometers), wt.-% of the core, and wt.-% of the shell for each Encapsulated Material K-L are reported.

TABLE 2

Encapsulated Tricalcium Silicates Using APCVD Process

| Encapsulated Material | Amount of Tricalcium Silicate Added (g) | Tricalcium Silicate Mean Particle Size (microns) | TMA Flow Rate ($cm^3$/min) | Water Flow Rate ($cm^3$/min) | Coating Time (minutes) |
|---|---|---|---|---|---|
| K | 30 | 149 | 500 | 1750 | 40 |
| L | 30 | 156 | 500 | 1750 | 40 |

TABLE 2a

Encapsulated Tricalcium Silicate Materials

| Encapsulated Material | Shell Thickness (nm) | wt.-% of Core | wt.-% of Shell |
|---|---|---|---|
| K | 35 | 99 | 1 |
| L | 32 | 99 | 1 |

Example 3. Encapsulated Materials with Portland Cement Cores

Portland cement (PC) was encapsulated with an aluminum oxide based material using atmospheric pressure chemical vapor deposition (APCVD). The Portland cement powder was coated by reacting trimethyl aluminum (obtained from Strem Chemicals and dispensed from a stainless steel bubbler) with water vapor in a fluidized bed reactor. The reactor was a glass frit funnel tube (4 cm diameter, 30 cm height). The reactor had an extended inlet tube from below the frit routed parallel to the body of the reactor, and an extended top area above the frit to allow the desired reactor height and fittings for a precursor injector tube and an exhaust outlet. Temperature was controlled at 180° C. using an oil bath. Nitrogen carrier gas was used with standard bubbler configurations for liquid precursors. The bubblers were maintained at an ambient temperature of about 22° C. Flow rates through the trimethyl aluminum (TMA) bubbler ranged from 240-1000 $cm^3$/minute. Flow rates through the water bubbler ranged from (610-2500 $cm^3$/minute). The total coating time ranged from 10-105 minutes. Encapsulated Materials M-U were prepared by varying the following parameters: amount of Portland cement added, particle size of the Portland cement powder, the TMA flow rate, the water flow rate, and coating time. In Table 3, the encapsulation parameters are listed for Encapsulated Materials M-U.

For Encapsulated Material M, the Portland cement powder added to the reactor was used as received and had a mean particle size of 17.1 microns (D10-D90 range of 6.0-33.5 microns) as determined using a Coulter Counter Multisizer 3 (Beckman Coulter Company, Brea, CA).

For Encapsulated Materials N-S, prior to adding to the reactor, fine particles were removed from the Portland cement sample by air classification using an AVEKA CCE centrifugal air classifier Model 100 (AVEKA CCE LLC, Cottage Grove, MN). Parameters were selected resulting in a 56% yield of coarse material to provide a sample having a mean particle size of 24.4 microns (D10-D90 range of 13.8-38.4 microns) as determined using a Coulter Counter Multisizer 3 (Beckman Coulter Company).

For Encapsulated Materials T-U, prior to adding to the reactor, fine particles and coarse particles were removed from the Portland cement sample using an AVEKA CCE centrifugal air classifier Model 100. In the first step, a coarse tail totaling about 24% of the initial sample was removed and then in the second step a fines tail of about 25% was removed from the remaining sample. The resulting Portland cement powder had a mean particle size of 19.6 microns (D10-D90 range of 9.4-31.5 microns) as determined using a Coulter Counter Multisizer 3 (Beckman Coulter Company).

In Table 3a, the calculated values of shell thickness (nanometers), wt.-% of the core, and wt.-% of the shell for each Encapsulated Material M-U are reported.

TABLE 3

Encapsulated Portland Cements Using APCVD Process

| Encapsulated Material | Amount of PC Added (g) | PC Particle Size (microns) | TMA Flow Rate ($cm^3$/min) | Water Flow Rate ($cm^3$/min) | Coating Time (minutes) |
|---|---|---|---|---|---|
| M | 14 | 17.1 | 240 | 610 | 105 |
| N | 25 | 24.4 | 500 | 1250 | 80 |
| O | 50 | 24.4 | 500 | 1250 | 85 |
| P | 50 | 24.4 | 500 | 1250 | 45 |
| Q | 50 | 24.4 | 500 | 1250 | 20 |
| R | 50 | 24.4 | 500 | 1250 | 10 |
| S | 100 | 24.4 | 1000 | 2500 | 40 |
| T | 50 | 19.6 | 500 | 1250 | 50 |
| U | 50 | 19.6 | 500 | 1750 | 67 |

TABLE 3a

Encapsulated Portland Cement Materials

| Encapsulated Material | Shell Thickness (nm) | wt.-% of Core | wt.-% of Shell |
|---|---|---|---|
| M | 161 | 95 | 5 |
| N | 204 | 95.5 | 4.5 |
| O | 109 | 97.5 | 2.5 |
| P | 57 | 98.5 | 1.5 |
| Q | 26 | 99.5 | 0.5 |
| R | 13 | 99.7 | 0.3 |
| S | 51 | 99 | 1 |

TABLE 3a-continued

| Encapsulated Portland Cement Materials | | | |
|---|---|---|---|
| Encapsulated Material | Shell Thickness (nm) | wt.-% of Core | wt.-% of Shell |
| T | 51 | 98.5 | 1.5 |
| U | 69 | 98 | 2 |

Example 4. Encapsulated Material with Portland Cement Core and Titanium Dioxide Shell Portland cement was encapsulated with a titanium dioxide based material using atmospheric pressure chemical vapor deposition (APCVD). The Portland cement powder (50 g) was coated by reacting titanium tetrachloride (obtained from Strem Chemicals and dispensed from a stainless steel bubbler) with water vapor in a fluidized bed reactor. Prior to charging the reactor, fine particles were removed from the Portland cement sample using the air classification procedure described for Encapsulated Materials N-S of Example 3. The mean particle size of the resulting powder was 24.4 microns (D10-D90 range of 13.8-38.4 microns) as determined using a Coulter Counter Multisizer 3 (Beckman Coulter Company). The reactor was a glass frit funnel tube (4 cm diameter, 30 cm height). The reactor had an extended inlet tube from below the frit routed parallel to the body of the reactor, and an extended top area above the frit to allow the desired reactor height and fittings for a precursor injector tube and an exhaust outlet. Temperature was controlled at 180° C. using an oil bath. Nitrogen carrier gas was used with standard bubbler configurations for liquid precursors. The bubblers were maintained at an ambient temperature of about 22° C. The flow rate through the titanium tetrachloride bubbler was 1000 $cm^3$/minute. The flow rate through the water bubbler was 1000 $cm^3$/minute. The total coating time was 57 minutes.

Example 5. Encapsulated Material with Portland Cement Core and Silicon Dioxide Shell Portland cement was encapsulated with a silicon dioxide based material using atmospheric pressure chemical vapor deposition (APCVD). The Portland cement powder (50 g) was coated by reacting silicon tetrachloride (obtained from Strem Chemicals and dispensed from a stainless steel bubbler) with water vapor in a fluidized bed reactor. Prior to charging the reactor, fine particles were removed from the Portland cement sample using the air classification procedure described for Encapsulated Materials N-S of Example 3. The mean particle size of the resulting powder was 24.4 microns (D10-D90 range of 13.8-38.4 microns) as determined using a Coulter Counter Multisizer 3 (Beckman Coulter Company). The reactor was a glass frit funnel tube (4 cm diameter, 30 cm height). The reactor had an extended inlet tube from below the frit routed parallel to the body of the reactor, and an extended top area above the frit to allow the desired reactor height and fittings for a precursor injector tube and an exhaust outlet. Temperature was controlled at 180° C. using an oil bath. Nitrogen carrier gas was used with standard bubbler configurations for liquid precursors. The bubblers were maintained at an ambient temperature of about 22° C. The flow rate through the silicon tetrachloride bubbler was 60 $cm^3$/minute. The flow rate through the water bubbler was 1300 $cm^3$/minute. The total coating time was 58 minutes.

In Table 3b, the calculated values of shell thickness (nanometers), wt.-% of the core, and wt.-% of the shell for the Encapsulated Materials of Examples 4 and 5 are reported.

TABLE 3b

| Encapsulated Portland Cement Materials | | | |
|---|---|---|---|
| Encapsulated Material of | Shell Thickness (nm) | wt.-% of Core | wt.-% of Shell |
| Example 4 | 137 | 97.0 | 3.0 |
| Example 5 | 154 | 97.5 | 2.5 |

Example 6

Four glass vials were each charged with 15 g of deionized water and 10 g of a pH 4 buffer solution (Buffer BDH5018, VWR International) and the solutions in the vials were stirred. Non-encapsulated Portland cement (0.25 g, 24.4 micron particle size) was added to the first vial. Non-encapsulated FAS glass (0.25 g) was added to the second vial. Encapsulated Material O (0.25 g) was added to the third vial. Encapsulated Material Q (0.25 g) was added to the fourth vial. Stirring was continued in the vials and the pH of each solution was measured over a period of 8 to 10 minutes using a Mettler Toledo M300 pH Meter (Mettler Toledo Corporation, Columbus, OH). The thickness of the shell of the Encapsulated Materials was modified by varying the coating time with longer coating times producing thicker shells. The shell of Encapsulated Material O was about 4.25 times thicker than the shell of Encapsulated Material Q. The results are presented in Table 4 and show that the encapsulated materials provided a delayed reaction with or release of the basic core material.

TABLE 4 pH Measurements of Encapsulated Portland Cements with Varying Shell Thickness

| | pH of Buffer Solution | | | | |
|---|---|---|---|---|---|
| Material | 0 min | 1 min | 2 min | 8 min | 10 min |
| Encapsulated Material O | 4.1 | 4.3 | 4.4 | 4.6 | Not Tested |
| Encapsulated Material Q | 4.1 | 5.1 | 8.0 | 11.1 | Not Tested |
| Non-Encapsulated Portland Cement (Control) | 4.1 | 11.5 | 11.6 | 11.7 | Not Tested |
| Non-Encapsulated FAS Glass (Comparative) | 4.1 | 4.3 | 4.3 | Not Tested | 4.5 |

Example 7

Two glass vials were each charged with 15 g of deionized water and 10 g of a pH 4 buffer solution (Buffer BDH5018, VWR International) and the solutions in the vials were stirred. The titanium dioxide Encapsulated Material of Example 4 (0.25 g) was added to the first vial. The silicon dioxide Encapsulated Material of Example 5 (0.25 g) was added to the second vial. Stirring was continued in the vials and the pH of each solution was measured over a period of 45 minutes using a Mettler Toledo M300 pH Meter (Mettler Toledo Corporation). The results are presented in Table 5 and show that the encapsulated materials provided a delayed reaction with or release of the basic core material.

TABLE 5 pH Measurements of Portland Cements Encapsulated with Titanium Dioxide and Silicon Dioxide Shells

| Encapsulated Material of | pH of Buffer Solution 0 min | 3 min | 5 min | 10 min | 15 min | 20 min | 30 min | 45 min |
|---|---|---|---|---|---|---|---|---|
| Example 4 | 4.1 | 4.6 | 4.8 | 5.1 | 5.3 | 5.6 | 7.8 | 10.8 |
| Example 5 | 4.1 | 4.8 | 5.0 | 5.8 | 9.4 | 10.6 | Not Tested | Not Tested |

Example 8

Three glass vials were each charged with 15 g of deionized water and 10 g of a pH 4 buffer solution (Buffer BDH5018, VWR International) and the solutions in the vials were stirred. Non-encapsulated tricalcium silicate (0.25 g) was added to the first vial. Encapsulated Material K (0.25 g) was added to the second vial. Encapsulated Material L (0.25 g) was added to the third vial. Stirring was continued in the vials and the pH of each solution was measured over a period of 12 minutes using a Mettler Toledo M300 pH Meter (Mettler Toledo Corporation). The results are presented in Table 6 and show that the encapsulated materials provided a delayed reaction with or release of the basic core material.

TABLE 6 pH Measurements of Tricalcium Silicates Encapsulated with an Aluminum Oxide Shell

| Material | pH of Buffer Solution 0 min | 1 min | 3 min | 5 min | 8 min | 10 min | 12 min |
|---|---|---|---|---|---|---|---|
| Encapsulated Material K | 4.1 | 5.0 | 5.5 | 6.2 | 10.9 | 11.3 | 11.4 |
| Encapsulated Material L | 4.1 | 5.1 | 6.0 | 10.8 | 11.6 | 11.7 | Not Tested |
| Non-Encapsulated Tricalcium Silicate (Control) | 4.1 | 11.6 | 11.9 | 12.0 | | Not Tested | |

Example 9

Four glass vials were each charged with 15 g of deionized water and 10 g of a pH 4 buffer solution (Buffer BDH5018, VWR International) and the solutions in the vials were stirred. Encapsulated Material O (0.25 g) was added to the first vial. Encapsulated Material P (0.25 g) was added to the second vial. Encapsulated Material Q (0.25 g) was added to the third vial. Encapsulated Material R (0.25 g) was added to the fourth vial. Stirring was continued in the vials and the pH of each solution was measured using a Mettler Toledo M300 pH Meter (Mettler Toledo Corporation). The time at which each solution reached a pH of 9 was recorded. The results are presented in Table 7 and show that delayed release of the basic core material depends on the thickness of the shell. The thickness of the shell of the Encapsulated Materials was modified by varying the coating time with longer coating times producing thicker shells. The thickness of the aluminum oxide shells for the Encapsulated Materials O-R progressively decreased as follows: Thickness of shell: Encapsulated Material O>Encapsulated Material P>Encapsulated Material Q>Encapsulated Material R. The relative shell thickness of Encapsulated Materials O-R was about 8.5:4.5:2:1 (Table 7).

TABLE 7 pH Measurements of Portland Cements Encapsulated with an Aluminum Oxide Shell

| Material | Time for Buffer Solution to Reach pH 9 (minutes) | Relative Shell Thickness |
|---|---|---|
| Encapsulated Material O | 350 | 8.5 |
| Encapsulated Material P | 37 | 4.5 |
| Encapsulated Material Q | 2.5 | 2 |
| Encapsulated Material R | 1.0 | 1 |

Example 10

Two glass vials were each charged with 15 g of deionized water and 10 g of a pH 4 buffer solution (Buffer BDH5018, VWR International) and the solutions in the vials were stirred. Non-encapsulated bioactive glass (0.25 g of 38-45 micron particle size) was added to the first vial. Encapsulated Material J (0.25 g) was added to the second vial. Stirring was continued in the vials and the pH of each solution was measured over a period of 60 minutes using a Mettler Toledo M300 pH Meter (Mettler Toledo Corporation). The results are presented in Table 8 and show that the encapsulated material provided a delayed reaction with or release of the basic core material.

TABLE 8 pH Measurements of Bioactive Glass Encapsulated with an Aluminum Oxide Shell

| Material | pH of Buffer Solution 0 min | 1 min | 2 min | 5 min | 10 min | 20 min | 30 min | 40 min | 60 min |
|---|---|---|---|---|---|---|---|---|---|
| Encapsulated Material J | 4.1 | 5.5 | 6.3 | 7.5 | 7.9 | 8.1 | 8.4 | 8.6 | 8.8 |
| Non-Encapsulated Bioactive Glass (Control) | 4.1 | 6.8 | 7.6 | 8.3 | 8.4 | 8.7 | 8.9 | 9.0 | Not Tested |

Example 11

Two glass vials were each charged with 25 g of deionized water. Non-encapsulated Portland cement (0.25 g, 24.4 micron particle size) was added to the first vial. Encapsulated Material P (0.25 g) was added to the second vial. The contents were stirred and the pH of each solution was measured over a period of 5 minutes using a Mettler Toledo M300 pH Meter (Mettler Toledo Corporation). The results are presented in Table 9 and show that the encapsulated material provided a delayed reaction or release of the basic core material.

TABLE 9 pH Measurements of Portland Cement Encapsulated with an Aluminum Oxide Shell

| Material | pH of Water 0 min | 20 sec | 40 sec | 1 min | 1.5 min | 2 min | 5 min |
|---|---|---|---|---|---|---|---|
| Encapsulated Material P | 7.2 | 8.6 | 10.3 | 10.6 | 10.8 | 11.0 | 11.3 |
| Non-Encapsulated Portland Cement (Control) | 7.2 | 11.5 | 11.8 | 11.8 | 11.9 | 11.9 | Not Tested |

Example 12

Two glass vials were each charged with 25 g of deionized water. Non-encapsulated bioactive glass (0.25 g of 38.45 micron particle size) was added to the first vial. Encapsulated Material J (0.25 g) was added to the second vial. The contents were stirred and the pH of each solution was measured over a period of 3 minutes using a Mettler Toledo M300 pH Meter (Mettler Toledo Corporation). The results are presented in Table 10 and show that the encapsulated material provided a delayed reaction with or release of the basic core material.

TABLE 10 pH Measurements of Bioactive Glass Encapsulated with an Aluminum Oxide Shell

| Material | pH of Water 0 min | 20 sec | 40 sec | 1 min | 2 min | 3 min |
|---|---|---|---|---|---|---|
| Encapsulated Material J | 7.2 | 9.8 | 9.9 | 9.9 | 9.9 | 9.9 |
| Non-Encapsulated Bioactive Glass (Control) | 7.2 | 10.5 | 10.6 | 10.6 | 10.6 | 10.6 |

Example 13 (Comparative)

A glass vial was charged with 25 g of deionized water and 0.25 g of non-encapsulated FAS glass (0.25 g) was added to the vial. The contents were stirred and the pH of the solution was measured over a period of 3 minutes using a Mettler Toledo M300 pH Meter (Mettler Toledo Corporation). The results are presented in Table 11.

TABLE 11 pH Measurements of Non-Encapsulated FAS Glass

| Material | pH of Water 0 min | 20 sec | 1 min | 5 min | 10 min | 20 min |
|---|---|---|---|---|---|---|
| Non-Encapsulated FAS Glass | 7.3 | 6.9 | 6.4 | 6.4 | 6.5 | 6.5 |

Example 14. Dental Compositions with Bioactive Glass Encapsulated Materials

Dental Compositions 1-6 (DC-1 to DC-6) were prepared using a paste selected from the Pastes B1-B6 as the first part of the composition and Paste A as the second part of the composition.

The composition of Paste A is reported in Table 12 (each component reported in wt.-%). Paste A was prepared in bulk. BHT and CPQ were added to a mixing cup that contained the HEMA. The filled cup was placed in a FlackTek SPEEDMIXER (FlackTek Incorporated, Landrum, SC) and the contents were mixed at 2500 rpm until a homogeneous mixture was achieved. A mixture of VBP in water was then added to the cup and mixing was continued. The CGP, Zr/Si nanocluster filler, and ytterbium fluoride components were combined to form a homogenous mixture and this mixture was then added to the cup. Mixing was continued until the mixture was homogeneous. The resulting paste was stored at 4° C. when not being used.

The compositions of Pastes B1-B4 and Paste BA are reported in Table 13 (each component reported in wt.-%). Pastes B1-B4 and Paste BA were prepared by adding EDMAB to a flask containing HEMA and mixing. In a separate beaker, FAS glass, Encapsulated Material H (from Table 1), and fumed silica were mixed to form a homogeneous mixture. The EDMAB\HEMA mixture was then added to the mixture in the beaker and the contents were stirred until homogeneous. The beaker was covered and the paste was used within 24 hours of preparation.

The compositions of Pastes B5 and B6 are reported in Table 14 and the pastes were prepared according to the general method described above for Pastes B1-B4.

For Dental Composition 1, Paste B1 was the first part of the composition. Paste A and Paste B1 of DC-1 (1:1 by weight) were combined on a mixing pad and spatulated until homogeneous (mixed for about 10-30 seconds). The pH of the resulting paste was immediately measured using an ORION PERPHECT ROSS pH Micro Electrode (catalog number 8220BNWP, Thermo Fisher Scientific Company, Waltham, PA). The pH reading at 30 seconds after insertion of the probe into the paste was recorded. The recorded pH was 4.3. A Teflon disk mold (3.1 mm diameter and 1.3 mm height) was immediately filled with the paste and the paste was then cured using an ELIPAR S10 curing light (3M Oral Care, Maplewood, MN) for 20 seconds on each side of the mold. The resulting molded disk was immediately removed from the mold and placed in a 2 mL plastic centrifuge tube that contained 1.5 mL of GIBCO phosphate buffered saline (PBS) solution (1×, pH 7.4) (Thermo Fisher Scientific). The disk was completely submerged in in the PBS solution. The tube was capped and stored at room temperature For Dental Composition 2 (DC-2), Paste B2 replaced Paste B1 as the first part of the composition. A molded disk was prepared with DC-2 according to the procedure described for DC-1. The pH of the paste measured immediately before filling the mold was 3.8.

For Dental Composition 3 (DC-3), Paste B3 replaced Paste B1 as the first part of the composition. A molded disk was prepared with DC-3 according to the procedure described for Dental Composition 1. The pH of the paste measured immediately before filling the mold was 3.7.

For Dental Composition 4 (DC-4), Paste B4 replaced Paste B1 as the first part of the composition. A molded disk was prepared with DC-4 according to the procedure described for DC-1. The pH of the paste measured immediately before filling the mold was 3.6.

For Dental Composition 5 (DC-5), Paste B5 replaced Paste B1 as the first part of the composition. A molded disk was prepared with DC-5 according to the procedure described for DC-1. The pH of the paste measured immediately before filling the mold was 4.9.

For Dental Composition 6 (DC-6), Paste B6 replaced Paste B1 as the first part of the composition. A molded disk was prepared with DC-6 according to the procedure described for DC-1. The pH of the paste measured immediately before filling the mold was 3.8.

For Comparative Dental Composition A (Comparative DC-A), Paste BA replaced Paste B1 as the first part of the composition. Paste BA contained no encapsulated material. A molded disk was prepared with Comparative DC-A according to the procedure described for DC-1. The pH of the paste measured immediately before filling the mold was 3.6.

For each submerged disk, the pH of the PBS solution was periodically measured over a period of 364 hours using an ORION PERPHECT ROSS pH Micro Electrode (catalog number 8220BNWP, Thermo Fisher). The sample was gently shaken before each measurement. The pH profiles of the PBS solutions are reported in Tables 15 and 16. The pH measurement recorded at "0 hr" was taken immediately after submersion of the disk in the PBS solution.

In Table 15, the concentration (wt.-%) of Encapsulated Material H incorporated in the Dental Compositions decreased from DC-1 to DC-4 with Comparative DC-A containing no Encapsulated Material H. (i.e. concentration of incorporated Encapsulated Material DC-1>DC-2>DC-3>DC-4>Comparative DC-A). In Table 16, the thickness of the shell of the Encapsulated Material in Dental Compositions DC-1, DC-5, and DC-6 was varied with DC-6 containing Encapsulated Material with the thickest shell and DC-5 containing Encapsulated Material with the thinnest shell.

TABLE 12

Composition of Paste A

| Component | Weight Percent (wt.-%) in the Composition |
|---|---|
| Hydroxyethyl methacrylate (HEMA) | 12.07 |
| Butylated hydroxytoluene (BHT) | 0.03 |
| Camphorquinone (CPQ) | 0.33 |
| Deionized water | 22.01 |
| VBP | 25.83 |
| Calcium glycerylphosphate | 4.57 |
| Zr/Si Nanocluster Filler | 30.14 |
| Ytterbium fluoride | 5.02 |

TABLE 13

Compositions of Pastes B1-B4 (Pastes Containing Varying Amounts of Encapsulated Material H) and Paste BA

| | Weight Percent (wt.-%) in the Composition | | | | |
|---|---|---|---|---|---|
| Component | B1 | B2 | B3 | B4 | BA |
| Hydroxyethyl methacrylate (HEMA) | 33.7 | 33.7 | 33.7 | 33.7 | 33.7 |
| Ethyl-4-dimethylamino benzoate (EDMAB) | 0.3 | 0.3 | 0.3 | 0.3 | 0.3 |
| FAS glass | 0.0 | 16.25 | 32.5 | 48.75 | 65.0 |
| Encapsulated Material H (from Table 1, Core: BG, Shell: AO) | 65.0 | 48.75 | 32.5 | 16.25 | 0.0 |
| Fumed Silica (R812S) | 1.0 | 1.0 | 1.0 | 1.0 | 1.0 |

TABLE 14

Compositions of Pastes B1, B5, and B6 (Pastes Prepared Using Encapsulated Materials that have Bioactive Glass Cores and Aluminum Oxide Shells of Varying Thickness)

| | Weight Percent (wt.-%) in the Composition | | |
|---|---|---|---|
| Component | B1 | B5 | B6 |
| Hydroxyethyl methacrylate (HEMA) | 33.7 | 33.7 | 33.7 |
| Ethyl-4-dimethylanino benzoate (EDMAB) | 0.3 | 0.3 | 0.3 |
| FAS glass | 0.0 | 0.0 | 0.0 |
| Encapsulated Material G (from Table 1) | 0.0 | 0.0 | 65.0 |
| Encapsulated Material H (from Table 1) | 65.0 | 0.0 | 0.0 |
| Encapsulated Material I (from Table 1) | 0.0 | 65.0 | 0.0 |
| Fumed Silica (R812S) | 1.0 | 1.0 | 1.0 |

TABLE 15 pH Measurements of PBS Solutions in Contact with Molded Disks Prepared from DC-1 to DC-4 (Dental Compositions with Varying Concentrations (wt.-%) of Encapsulated Material H)

| Disk from Dental Composition | pH of PBS Solution | | | | | | |
|---|---|---|---|---|---|---|---|
| (Example 14) | 0 hr | 2 hr | 20 hr | 46 hr | 72 hr | 147 hr | 364 hr |
| DC-1 | 7.2 | 7.5 | 8.3 | 9.1 | 9.7 | 10.3 | 10.7 |
| DC-2 | 7.2 | 7.5 | 7.4 | 7.9 | 9.2 | 9.9 | 10.6 |
| DC-3 | 7.2 | 6.9 | 7.1 | 7.2 | 7.3 | 7.8 | 8.5 |
| DC-4 | 7.2 | 6.7 | 6.8 | 6.6 | 6.7 | 6.7 | 6.6 |
| Comparative DC-A (No Encapsulated Material H) | 7.2 | 6.7 | 6.2 | 5.8 | 5.7 | 5.7 | 5.7 |

TABLE 16 pH Measurements of PBS Solutions in Contact with Molded Disks Prepared from DC-1, DC-5, and DC-6 (Dental Compositions containing Encapsulated Materials of Varying Shell Thickness)

| Dental Composition (Example 14) | pH of PBS Solution 0 hr | 1 hr | 30 hr | 45 hr | 71 hr | 100 hr | 320 hr | 360 hr |
|---|---|---|---|---|---|---|---|---|
| DC-6 | 7.2 | 6.9 | 7.2 | NT | NT | 8.4 | 9.8 | NT |
| DC-1 | 7.2 | 7.1 | NT | 8.3 | 9.1 | NT | NT | 10.3 |
| DC-5 | 7.2 | 7.4 | 9.3 | NT | NT | 9.9 | 10.5 | NT |

NT = Not Tested

Example 15. Dental Compositions with Portland Cement Encapsulated Materials

Dental Compositions (DC-7 to DC-11) were prepared using a paste selected from the Pastes B7-B11 as the first part of the composition and Paste A as the second part of the composition.

Paste A was prepared as reported in Example 14.

The compositions of Pastes B7-B9 are reported in Table 17 (each component reported in wt.-%). Pastes B7-B9 were prepared by adding EDMAB to a flask containing HEMA and mixing.

In a separate beaker, FAS glass, Encapsulated Material P (from Table 3), and fumed silica were mixed to form a homogeneous mixture. The EDMAB\HEMA mixture was then added to the mixture in the beaker and the contents were stirred until homogeneous. The beaker was covered and the paste was used within 24 hours of preparation.

The composition of Paste B10 is reported in Table 18. Paste B10 was prepared according to the general method described above for Pastes B7-B9 with the exception that Encapsulated Material P was replaced with the Encapsulated Material of Example 4 (titanium dioxide encapsulated Portland cement).

The composition of Paste B11 is reported in Table 19. Paste B11 was prepared according to the general method described above for Pastes B7-B9 with the exception that Encapsulated Material P was replaced with the Encapsulated Material of Example 5 (silicon dioxide encapsulated Portland cement).

For Dental Composition 7 (DC-7), Paste B7 was the first part of the composition. Paste A and Paste B7 of DC-7 (1:1 by weight) were combined on a mixing pad and spatulated until homogeneous (mixed for about 10-30 seconds). The pH of the resulting paste was immediately measured using an ORION PERPHECT ROSS pH Micro Electrode (catalog number 8220BNWP, Thermo Fisher Scientific Company). The pH reading at 30 seconds after insertion of the probe into the paste was recorded. The recorded pH was 3.5. A Teflon disk mold (3.1 mm diameter and 1.3 mm height) was immediately filled with the paste and the paste was then cured using an ELIPAR S10 curing light (3M Oral Care, Maplewood, MN) for 20 seconds on each side of the mold. The resulting molded disk was immediately removed from the mold and placed in a 2 mL plastic centrifuge tube that contained 1.5 mL of GIBCO phosphate buffered saline (PBS) solution (1×, pH 7.4) (Thermo Fisher Scientific). The disk was completely submerged in in the PBS solution. The tube was capped and stored at room temperature For Dental Composition 8 (DC-8), Paste B8 replaced Paste B7 as the first part of the composition. A molded disk was prepared with DC-8 according to the procedure described for DC-7. The pH of the paste measured immediately before filling the mold was 3.5.

For Dental Composition 9 (DC-9), Paste B9 replaced Paste B7 as the first part of the composition. A molded disk was prepared with DC-9 according to the procedure described for DC-7. The pH of the paste measured immediately before filling the mold was 3.6.

For Dental Composition 10 (DC-10), Paste B10 replaced Paste B7 as the first part of the composition. A molded disk was prepared with DC-10 according to the procedure described for DC-7. The pH of the paste measured immediately before filling the mold was 3.3.

For Dental Composition 11 (DC-11), Paste B11 replaced Paste B7 as the first part of the composition. A molded disk was prepared with DC-11 according to the procedure described for DC-7. The pH of the paste measured immediately before filling the mold was 3.3.

For each submerged disk, the pH of the PBS solution was periodically measured over a period of 333 or 646 hours using an ORION PERPHECT ROSS pH Micro Electrode (catalog number 8220BNWP, Thermo Fisher). The sample was gently shaken before each measurement. The pH profiles of the PBS solutions are reported in Tables 20 and 21. The pH measurement recorded at “0 hr” was taken immediately after submersion of the disk in the PBS solution.

In Table 20, Dental Compositions with varying concentrations of incorporated Encapsulated Material P were evaluated. DC-7 contained about twice as much Encapsulated Material P (wt.-% basis) as DC-9. Comparative DC-A contained no Encapsulated Material P.

TABLE 17

Compositions of Pastes B7-B9 (Pastes Containing Varying Amounts of Encapsulated Material P)

| Component | Weight Percent (wt.-%) in the Composition B7 | B8 | B9 |
|---|---|---|---|
| Hydroxyethyl methacrylate (HEMA) | 33.7 | 33.7 | 33.7 |
| Ethyl-4-dimethylanino benzoate (EDMAB) | 0.3 | 0.3 | 0.3 |
| FAS glass | 0.0 | 16.25 | 32.5 |
| Encapsulated Material P (from Table 3, Core: PC, Shell: AO) | 65.0 | 48.75 | 32.5 |
| Fumed Silica (R812S) | 1.0 | 1.0 | 1.0 |

TABLE 18

Composition of Paste B10 (Containing Encapsulated Material of Example 4)

| Component | Weight Percent (wt.-%) in the Composition |
|---|---|
| Hydroxyethyl methacrylate (HEMA) | 33.7 |
| Ethyl-4-dimethylanino benzoate (EDMAB) | 0.3 |
| FAS glass | 16.25 |
| Encapsulated Material of Example 4 (Core: PC, Shell: $TiO_2$) | 48.75 |
| Fumed Silica (R812S) | 1.0 |

TABLE 19

| Composition of Paste B11 (Containing Encapsulated Material of Example 5) | |
|---|---|
| Component | Weight Percent (wt.-%) in the Composition |
| Hydroxyethyl methacrylate (HEMA) | 33.7 |
| Ethyl-4-dimethylanino benzoate (EDMAB) | 0.3 |
| FAS glass | 16.25 |
| Encapsulated Material of Example 5 (Core: PC, Shell: $SiO_2$) | 48.75 |
| Fumed Silica (R812S) | 1.0 |

TABLE 20 pH Measurements of PBS Solutions in Contact with Molded Disks Prepared from DC-7 and DC-9 (Dental Compositions with Varying Concentrations (wt.-%) of Encapsulated Material P)

| Dental Composition | pH of PBS Solution | | | | | |
|---|---|---|---|---|---|---|
| (Example 15) | 0 hr | 19 hr | 116 hr | 260 hr | 429 hr | 646 hr |
| DC-7 | 7.3 | 7.4 | 7.8 | 8.6 | 8.8 | 9.6 |
| DC-9 | 7.3 | 7.1 | 7.3 | 7.6 | 7.9 | 7.5 |
| Comparative DC-A (no Encapsulated Material P) | 7.3 | 6.7 | 6.4 | 6.3 | 6.3 | 6.3 |

TABLE 21 pH Measurements of PBS Solutions in Contact with Molded Disks Prepared from DC-8, DC-10, and DC-11 (Dental Compositions with Encapsulated Materials Having Different Shell Materials)

| Dental Composition | pH of PBS Solution | | | |
|---|---|---|---|---|
| (Example 15) | 0 hr | 45 hr | 168 hr | 333 hr |
| DC-8 | 7.3 | 7.3 | 7.8 | 8.1 |
| DC-10 | 7.3 | 7.6 | 8.7 | 9.4 |
| DC-11 | 7.3 | 7.6 | 8.4 | 8.7 |
| Comparative DC-A (no encapsulated material) | 7.3 | 6.6 | 6.5 | 6.4 |

Example 16. Dental Composition with Tricalcium Silicate Encapsulated Material A molded disk was prepared with Dental Composition DC-12 according to the procedure reported in Example 14. DC-12 was prepared using the Paste B12 (composition in Table 22) as the first part of the composition and Paste A as the second part of the composition. The pH of the spatulated paste measured immediately before filling the mold was 3.7. The pH of the PBS solution surrounding the disk was periodically measured for 790 hours according to the procedure described in Example 14 and the results reported in Table 23. The pH measurement recorded at “0 hr” was taken immediately after submersion of the disk in the PBS solution.

TABLE 22

| Composition of Paste B12 (Containing Encapsulated Material K) | |
|---|---|
| Component | Weight Percent (wt.-%) in the Composition |
| Hydroxyethyl methacrylate (HEMA) | 33.7 |
| Ethyl-4-dimethylanino benzoate (EDMAB) | 0.3 |
| FAS glass | 16.25 |
| Encapsulated Material K (from Table 2, Core: TCS, Shell: AO) | 48.75 |
| Fumed Silica (R812S) | 1.0 |

TABLE 23 pH Measurements of PBS Solution in Contact with Molded Disk Prepared from DC-12 [Dental Composition Containing Encapsulated Material K (Tricalcium Silicate Core and Aluminum Oxide Shell)]

| Dental | pH of PBS Solution | | | | | |
|---|---|---|---|---|---|---|
| Composition | 0 hr | 18 hr | 90 hr | 264 hr | 430 hr | 790 hr |
| DC-12 | 7.3 | 7.5 | 8.3 | 9.0 | 9.5 | 9.8 |

Example 17. Cell Proliferation of Dental Pulp Stem Cells Contacted with Dental Compositions Containing Encapsulated Bioactive Glass Molded disks (3.1 mm diameter and 1.3 mm height) of Dental Compositions 1-4, and Comparative Dental Composition A were prepared using the general mixing and curing procedure for preparing a molded disk described in Example 14. Individual disks were also prepared from a commercially available dental base/liner product (Comparative Example X) and a commercially available dental pulp cap/liner product (Comparative Example Y). The disks were individually sterilized by sequentially placing a disk in a 70% ethanol bath for 20 minutes, rinsing with PBS (3 times), and then incubating overnight (37° C., 5% $CO_2$, 98% relative humidity) in dental pulp stem cell (DPSC) basal media (Lonza Group LTD., Basel, Switzerland). Human dental pulp stem cells (DPSCs, Lonza Group LTD.) were seeded at 20,000 cells/mL per well in a COSTAR 48 well cell culture plate (Corning Incorporated, Corning, NY) containing DPSC basal media. Each well was loaded with a disk and the cells were cultured for seven days (37° C., 5% $CO_2$, 98% relative humidity). As a Control Example, additional wells were seeded with the human dental pulp stem cells, but a molded disk was not added to any of these wells.

On day seven, the DPSC samples were evaluated for cell proliferation using an MTT colorimetric assay kit (Invitrogen Corporation, Carlsbad, CA) with the absorbance measurements taken at 540 nm using a microplate reader (Tecan Group LTD., Mannedorf, Switzerland). In Table 24, the mean OD540 (n=6) for DPSC samples contacted with Dental Compositions 1-4 (containing varying concentrations of encapsulated Bioactive glass material), Comparative Dental Composition A (containing no encapsulated material), Comparative Examples X and Y, and the Control Example are recorded.

TABLE 24

| Cell Proliferation of Dental Pulp Stem Cells | | |
|---|---|---|
| Molded Disk | OD540 | % of Control |
| DC-1 | 0.98 ± 0.03 | 83% |
| DC-2 | 0.95 ± 0.04 | 83% |
| DC-3 | 0.89 ± 0.04 | 75% |
| DC-4 | 0.65 ± 0.10 | 55% |
| Comparative DC-A | 0.28 ± 0.07 | 24% |
| Comparative Example X | 1.05 ± 0.05 | 89% |
| Comparative Example Y | 0.71 ± 0.02 | 60% |
| Control Example (no disk added to well) | 1.18 ± 0.03 | |

Example 18. Cell Proliferation of Dental Pulp Stem Cells Contacted with Dental Compositions Containing Encapsulated Portland Cement or Encapsulated Tricalcium Silicate Molded disks (3.1 mm diameter and 1.3 mm height) of Dental Compositions 8, 10, 11, 12, Comparative Dental Composition A, Comparative Example X, and Comparative Example Y were prepared and tested for cell proliferation according to the procedure described in Example 17. A Control Example (wells seeded with DPSCs but no molded disk added) was also prepared as described in Example 17. In Table 25, the mean OD540 (n=4) for DPSC samples contacted with Dental Compositions 8, 10, 11, 12 (containing encapsulated materials having Portland cement or tricalcium silicate cores with different shell coatings), Comparative Dental Composition A (containing no encapsulated material), Comparative Examples X and Y, and the Control Example are recorded.

TABLE 25

| Cell Proliferation of Dental Pulp Stem Cells | | |
|---|---|---|
| Molded Disk | OD540 | % of Control |
| DC-8 | 1.20 ± 0.08 | 91% |
| DC-10 | 1.22 ± 0.05 | 92% |
| DC-11 | 1.13 ± 0.08 | 86% |
| DC-12 | 0.95 ± 0.08 | 72% |
| Comparative DC-A | 0.09 ± 0.04 | 7% |
| Comparative Example X | 1.03 ± 0.05 | 78% |
| Comparative Example Y | 1.06 ± 0.35 | 80% |
| Control Example (no disk added to well) | 1.32 ± 0.04 | |

Example 19. ALP Activity of Dental Pulp Stem Cells Contacted with Dental Compositions Molded disks (3.1 mm diameter and 1.3 mm height) of Dental Compositions 1-4, Comparative Dental Composition A, Comparative Example X, and Comparative Example Y were prepared using the general mixing and curing procedure for preparing a molded disk described in Example 14. The disks were individually sterilized by sequentially placing a disk in a 70% ethanol bath for 20 minutes, rinsing with PBS (3 times), and then incubating overnight (at 37° C., 5% $CO_2$, 98% relative humidity) in dental pulp stem cell (DPSC) basal media (Lonza Group LTD). Human dental pulp cells (DPSCs, Lonza Group LTD.) were seeded at 20,000 cells/mL per well in a COSTAR 48 well cell culture plate (Corning Incorporated, Corning, NY) containing DPSC basal media. Each well was loaded with a disk and the cells were cultured for seven days (37° C., 5% $CO_2$, 98% relative humidity). As a Control Example, additional wells were seeded with the human dental pulp stem cells, but a molded disk was not added to any of these wells On day seven, the DPSC cells were collected and the cell lysate for each sample was analyzed for alkaline phosphatase (ALP) activity using a human ALP ELISA kit (BioVision Incorporated, San Francisco, CA) according to the manufacturer's instructions. In Table 26, the mean ALP concentration (n=2) in mU/mL for DPSC samples contacted with Dental Compositions 1-4 (containing varying concentrations of encapsulated Bioactive glass material), Comparative Dental Composition A (containing no encapsulated material), the Comparative Examples X and Y, and the Control Example are recorded.

TABLE 26

| Alkaline Phosphatase (ALP) Activity | |
|---|---|
| Molded Disk | ALP Level (mU/mL) |
| DC-1 | 1.14 ± 0.12 |
| DC-2 | 1.12 ± 0.02 |
| DC-3 | 0.79 ± 0.01 |
| DC-4 | 0.40 ± 0.10 |
| Comparative DC-A | 0.12 ± 0.02 |
| Comparative Example X | 0.65 ± 0.06 |
| Comparative Example Y | 0.27 ± 0.05 |
| Control Example (no disk added to well) | 0.79 ± 0.18 |

Example 20. ALP Activity of Dental Pulp Stem Cells Contacted with Dental Compositions Molded Disks (3.1 mm diameter and 1.3 mm height) of Dental Compositions 8, 10, 11, 12, Comparative Dental Composition A, Comparative Example X, and Comparative Example Y were prepared and tested for ALP activity according to the procedure described in Example 19. A Control Example (wells seeded with DPSCs but no molded disk added) was also prepared as described in Example 19. In Table 27, the mean ALP concentration (n=1-3) in mU/mL for DPSC samples contacted with Dental Compositions 8, 10, 11, 12 (containing encapsulated materials having Portland cement or tricalcium silicate cores with different shell coatings), Comparative Dental Composition A (containing no encapsulated material), Comparative Examples X and Y, and the Control Example are recorded.

TABLE 27

| Alkaline Phosphatase (ALP) Activity | |
|---|---|
| Molded Disk | ALP Level (mU/mL) |
| DC-8 (n = 2) | 1.05 ± 0.23 |
| DC-10 (n = 3) | 0.96 ± 0.12 |
| DC-11 (n = 3) | 0.70 ± 0.16 |
| DC-12 (n = 2) | 0.49 ± 0.15 |
| Comparative DC-A (n = 2) | 0.00 ± 0.01 |
| Comparative Example X (n = 1) | 0.23 |
| Comparative Example Y (n = 1) | 0.09 |
| Control Example (no disk added to well) (n = 1) | 0.32 |

Example 21. Encapsulated Materials with Calcium Hydroxide Cores or Mixed Phase Calcium Silicate Cores Calcium Hydroxide (CH) powder was obtained from Jost Chemical (St. Louis, MO, product number: 2242). The material was sieved through a 25 micron sieve.

Mixed Phase Calcium Silicate (MPCS) was prepared by mixing 14.1 wt.-% $SiO_2$, 50.3 wt.-% $CaCO_3$, 34.7 wt.-% $H_2O$, and 0.8 wt.-% BYK-W9012. BYK-W9012 wetting and dispersing additive was obtained from BYK-Chemie GmbH, Wesel, Germany. After mixing, the resulting slurry was dried at 100° C. for 12 hours, then sintered at 1500° C. for two hours. The resulting particles were ground using a mortar and pestle to provide a powder with a measured mean particle size of 11.35 microns by laser diffraction.

Calcium Hydroxide (CH) and Mixed Phase Calcium Silicate (MPCS) were each encapsulated with aluminum oxide using the APCVD process and equipment described in Example 2, with the exception that the reactor was heated using heater tape, and the powder amounts and flow rates were as reported in Table 28.

TABLE 28

Encapsulated CH and MPCS Using APCVD Process

| Encap-sulated Material | Amount of Core Material Added (g) | Core Material Mean Particle Size (microns) | TMA Flow Rate ($cm^3$/min) | Water Flow Rate ($cm^3$/min) | Coating Time (minutes) |
|---|---|---|---|---|---|
| CH | 65 | 13 microns | 250 | 650 | 267 |
| MPCS | 65 | 11 microns | 250 | 650 | 240 |

Example 22. pH Buffer Tests of Encapsulated Materials

Tests as described in Example 6 were performed on both non-encapsulated CH and MPCS, and encapsulated CH and MPCS sampled from the batches described in Table 28. The pH of the buffer solution just prior to powder addition was 4.1 for all four samples. The results are presented in Table 29 and show that the encapsulated materials provided a delayed reaction with or release of the basic core material.

TABLE 29 pH Measurements of CH and MPSC Samples of Example 28

| | pH of Buffer Solution | | | | |
|---|---|---|---|---|---|
| Material | 1 min | 2 min | 8 min | 10 min | 25 min |
| Encapsulated CH Material | 4.8 | 5.0 | 7.3 | 10.8 | Not Tested |
| Non-encapsulated CH (Control) | 12.1 | 12.2 | Not tested | Not tested | Not Tested |
| Encapsulated MPCS | 4.6 | 4.9 | 5.6 | 5.8 | 9.3 |
| Non-Encapsulated MPCS (Control) | 9.9 | 10.7 | Not tested | Not tested | Not Tested |

Example 23. Portland Cement Cores Encapsulated using Atomic Layer Deposition (ALD)

Portland cement powder (5 g) was microencapsulated using an atomic layer deposition (ALD) process. A flow through atomic layer deposition (FTALD) reactor incorporating a sequential 4-step process (precursor A, purge, precursor B, purge) was used to deposit aluminum oxide coatings by self-limiting surface reactions on the targeted particle material.

The sequential 4-step process consisted of the following sequence: (1) Precursor A (i.e., trimethyl aluminum (TMA)) pulse, (2) $N_2$ purge, (3) Precursor B (i.e., Ozone @ 20% pulse), and (4) $N_2$ purge. The time and pressure for the TMA precursor pulse was set at 1.125 seconds, with a pressure of 1 to 3 torr inside the reactor. The time and pressure for the ozone precursor pulse was set at 1.000 seconds, with a pressure of 1 to 4 torr inside the reactor. Purging times were in the range of 100 to 120 seconds per half cycle. The 4-step sequence is referred to herein as 1 ALD cycle. The 5 g sample of Portland cement was processed using a total of 200 ALD cycles at a process temperature of 150° C.

The internal sample chamber consisted of a 34 mm fritted tube with one end closed off and the other open end fitted with a fitting (VCR8 fitting). The fitting was then attached to the precursor delivery system which allowed for the addition of various gases to flow into the inside of the fritted tube and exhaust through the walls of the fritted tube.

The precursor delivery system was designed with a rotating union such that the fritted tube (sample chamber) was allowed to rotate independently of the rest of the reactor system. The fritted tube attached to the precursor delivery system was then placed inside of a temperature controlled sleeve or tube used to control the temperature of the particles and precursors during the deposition process.

During the deposition process, the tube containing the particles was rotated which caused the particles to be lifted along the wall of the tube and to free fall back to the bottom of the tube. During the free fall, the particles were sequentially exposed to the various precursors and purge steps as the gases flowed into the open end of the fritted tube and were exhausted through the walls. A vibrating motor was also attached to the reactor assembly providing additional agitation to keep the particles free flowing during the deposition process. All gases were heated to 80° C. so that the gas flow did not cool the sample.

The precursor charges were monitored with a residual gas analyzer (obtained under the trade designation "SRS RESIDUAL GAS ANALYZER" from Stanford Research Systems, Inc., Sunnyvale, CA) to make sure that sufficient amounts of precursors were being delivered to the reactor.

The resulting encapsulated powder was measured for pH change using the procedure described in Example 6. The results are reported in Table 30.

TABLE 30 pH Measurements of Portland Cement Encapsulated using ALD

| | pH of Buffer Solution | | | | | | | |
|---|---|---|---|---|---|---|---|---|
| Encapsulated Material | 5 min | 10 min | 15 min | 20 min | 25 min | 40 min | 53 min | 54 min |
| Example 23 | 4.2 | 4.5 | 4.7 | 5.0 | 5.2 | 5.9 | 8.6 | 9.0 |

Example 24. Adhesion Measurements of Dental Composition 8 (DC-8) and Comparative Dental Composition A (DC-A) Applied to a Dentin Surface Bovine incisors (10) were separately embedded into 25 mm diameter by 10-20 mm tall resin pucks (one tooth per puck). Each resulting puck was ground with 120 grit sandpaper to expose the dentin layer of the tooth, and polished with 320 grit sandpaper. All experiments were conducted in a room with a constant temperature of 75° C., humidity of 50%, and lights filtered at 450 nm. Each tooth surface was blotted to remove excess water and 3M 201+ masking tape (3M Company, Maplewood, MN) was used as a mask to frame a 5 mm diameter circle of exposed dentin. DC-8 (prepared as described in Example 15) was applied to cover the site of exposed dentin, wiped level with the mask using a spatula, and then cured for 20 seconds using an ELIPAR S10 LED curing light (3M Company). SCOTCHBOND Universal Adhesive (3M Company) was then applied to the cured surface for 20 seconds using a disposable applicator. The site was dried with a gentle stream of air for 5 seconds, and then light cured with an ELIPAR S10 LED curing light for 10 seconds. A Teflon mask, 2-5 mm deep, with a 5 mm diameter hole lined with gelatin was aligned with the tape mask and secured with a metal clip. The hole was then filled with FILTEK Z250 dental composite resin (3M Company) and light cured for 20 seconds with an ELIPAR S10 LED curing light to create a peg. The tooth sample was then placed in a chamber (37° C. and 95% humidity) for 0.5 hour. The metal clip was removed from the tooth sample and each sample was soaked in deionized water for 24 hours at 37° C. After 24 hours, the gelatin had dissolved and the Teflon mask was removed. The resin puck was secured in a round grip fixture on the upper arm of an Instron 5944 (Instron Corporation, Norwood, MA). The lower fixture had a wire loop, approximately 90 mm long. The wire was looped over the FILTEK Z250 peg and secured flush with the tooth/resin surface. Tension was than applied until failure (i.e. the assembly was broken from the surface of the tooth or the tooth was broken) in order to determine the adhesion of the cured dental composition DC-8 to the tooth.

The procedure was repeated using Comparative Dental Composition A (DC-A, prepared as in Example 14) instead of DC-8. The average (n=10) adhesion values (MPa) determined for dental compositions DC-A and DC-8 are reported in Table 31.

TABLE 31

Adhesion Measurements for Dental Compositions DC-8 and DC-A to Dentin.

| Dental Composition | Average Adhesion (MPa) (n = 10) | Standard deviation (MPa) |
|---|---|---|
| DC-8 | 10.09 | 2.74 |
| DC-A | 8.11 | 2.10 |

Example 25. Dental Composition (DC-13)

Dental Composition B (DC-B) was prepared by adding 120 mg of IRGACURE 819 (photoinitiator obtained from BASF Corporation, Wyandotte, MI) to 40 g of SR 603 (polyethylene glycol (400) dimethacrylate obtained from Sartomer Americas, Exton, PA). The mixture was mixed for 1 minute at 3000 rpm in a FlackTek DAC 150 FVZ Speed Mixer for a total of 3 times. A Teflon disk mold (3.1 mm diameter and 1.3 mm height) was immediately filled with DC-B and was then cured using an Elipar™ DeepCure-S LED curing light (3M Oral Care) for 20 seconds on each side of the mold. The resulting molded disk was immediately removed from the mold and placed in a 2 mL plastic centrifuge tube that contained 1.5 mL of GIBCO phosphate buffered saline (PBS) solution (1×, pH 7.4) (Thermo Fisher Scientific). The disk was completely submerged in the PBS solution. The tube was capped and stored at room temperature. The Disk from Dental Composition B served as a control (no encapsulated material included).

Dental Composition 13 (DC-13) was prepared by combining 3 g of Encapsulated Material P with 1 g of DC-B. The mixture was mixed for 1 minute at 3000 rpm, three times. The viscosity of DC-13 was 31066 cP (at 23° C., a shear rate of 100 $s^{-1}$, and using a Type F T-bar spindle). Molded disks were prepared with DC-13 according to the procedure described for DC-B.

Dental Composition C (DC-C) was prepared by combining 3 g of non-encapsulated Portland cement with 1 g of DC-B. The mixture was mixed for 1 minute at 3000 rpm, three times. Molded disks were prepared with DC-C according to the procedure described for DC-B. The Disk from Dental Composition C served as a control (non-encapsulated Portland cement included).

For each submerged disk, the pH of the PBS solution was periodically measured over a period of 90.4 hours using an ORION PERPHECT ROSS pH Micro Electrode (catalog number 8220BNWP, Thermo Fisher). Each sample was gently shaken before each measurement. The pH profiles of the PBS solutions are reported in Table 32. The pH measurement recorded at "0 hr" was taken immediately after submersion of a disk in the PBS solution.

TABLE 32 pH Measurements of PBS Solutions in Contact with Molded Disks prepared from DC-13, DC-B, and DC-C.

| Disk from Dental | pH of PBS Solution | | | | |
|---|---|---|---|---|---|
| Composition | 0 hr | 0.4 hr | 1.1 hr | 2.6 hr | 90.4 hr |
| DC-13 | 7.3 | 7.6 | 8.3 | 8.5 | 11.5 |
| DC-B (Control, No Encapsulated Material P) | 7.3 | 7.4 | 7.4 | 7.4 | 7.6 |
| DC-C (Control, Non-Encapsulated Portland Cement) | 7.3 | 8.6 | 10.2 | 10.8 | 12.2 |

Example 26. Encapsulated Material V (PC Core and AO Shell)

Portland cement (PC) was encapsulated with an aluminum oxide (AO) based material using atmospheric pressure chemical vapor deposition (APCVD). The Portland cement powder was coated by reacting trimethyl aluminum (obtained from Strem Chemicals and dispensed from a stainless steel bubbler) with water vapor in a fluidized bed reactor. The reactor was a glass frit funnel tube (12 cm diameter, 30 cm height). The reactor had an extended inlet tube from below the frit routed parallel to the body of the reactor, and an extended top area above the frit to allow the desired reactor height and fittings for a precursor injector tube and an exhaust outlet. Temperature was controlled at 180° C. using an oil bath. Nitrogen carrier gas was used with standard bubbler configurations for liquid precursors. The bubblers were maintained at an ambient temperature of about 2° C. The flow rate through the trimethyl aluminum (TMA) bubbler was 1000 $cm^3$/minute. The flow rate through the water bubbler was 2500 $cm^3$/minute. The total coating time was 214 minutes. The amount of Portland cement added to the reactor was 370 g and the particle size of the Portland cement powder was 20 microns.

Encapsulated Material V was calculated to have a shell thickness of 50 nm. The calculated weight percentages (wt.-%) were 98.7 wt.-% core material and 1.3 wt.-% shell material.

Example 27. Dental Composition (DC-14)

The composition of Paste A1 is reported in Table 33 (each component reported in wt.-%). Paste A1 was prepared in bulk. BHT, CPQ and LUPEROX A75 Benzoyl Peroxide (Sigma Aldrich Corporation) were added to a mixing cup that contained the HEMA. The filled cup was placed in a FlackTek SPEEDMIXER and the contents were mixed at 2500 rpm until a homogeneous mixture was achieved. A mixture of VBP in water was then added to the cup and mixing was continued. The CGP, Zr/Si nanocluster filler, and ytterbium fluoride components were combined to form a homogenous mixture and this mixture was then added to the cup. Mixing was continued until the mixture was homogeneous. The resulting paste was stored at 4° C. when not being used.

The composition of Paste B13 is reported in Table 34 (each component reported in wt.-%). Paste B13 was prepared by adding EDMAB and 2-(4-Dimethylamino)phenyl) ethanol (DMAPE) to a flask containing HEMA and mixing. In a separate beaker, FAS glass, Encapsulated Material V, and fumed silica were mixed to form a homogeneous mixture. The EDMAB\DMAPE|\HEMA mixture was then added to the mixture in the beaker and the contents were stirred until homogeneous. The beaker was covered and the paste was used within 24 hours of preparation.

Paste A1 (0.25 g) and Paste B13 (0.25 g) were combined on a mixing pad and spatulated until homogeneous (mixed for 20 seconds). The mixture was spatulated into a mound approximately 1.5 cm in diameter and 3 mm at the highest point. At the time point of 30 seconds after the initiation of mixing, the composition was placed in a warming oven (37° C.) and checked for hardening by probing with the tip of a spatula every 20-30 seconds. After 75 seconds in the oven, the composition had hardened.

TABLE 33

Composition of Paste A1

| Component | Weight Percent (wt.-%) in the Composition |
|---|---|
| Hydroxyethyl methacrylate (HEMA) | 11.89 |
| Butylated hydroxytoluene (BHT) | 0.03 |
| Camphorquinone (CPQ) | 0.33 |
| Benzoyl peroxide (BPO) | 1.48 |
| Deionized water | 21.68 |
| VBP | 25.45 |
| Calcium glycerylphosphate | 4.50 |
| Zr/Si Nanocluster Filler | 29.69 |
| Ytterbium fluoride | 4.95 |

TABLE 34

Composition of Paste B13

| Component | Weight Percent (wt.-%) in the Composition |
|---|---|
| Hydroxyethyl methacrylate (HEMA) | 33.7 |
| Ethyl-4-dimethylamino benzoate EDMAB | 0.30 |
| 2-(4-Dimethylamino)phenyl)ethanol (DMAPE) | 0.99 |
| FAS glass | 16.09 |
| Encapsulated Material V | 48.27 |
| Fumed Silica (R812S) | 0.99 |

Example 28. Encapsulated Material 1 (PC Core and AO Shell)

Portland cement (PC) was encapsulated with an aluminum oxide (AO) based material using atmospheric pressure chemical vapor deposition (APCVD). The Portland cement powder was coated by reacting trimethyl aluminum (obtained from Strem Chemicals) and dispensed from a stainless steel bubbler) with water vapor in a fluidized bed reactor. The reactor was a glass frit funnel tube (12 cm diameter, 30 cm height). The reactor had an extended inlet tube from below the frit routed parallel to the body of the reactor, and an extended top area above the frit to allow the desired reactor height and fittings for a precursor injector tube and an exhaust outlet. Temperature was controlled at 180° C. using an oil bath. Nitrogen carrier gas was used with standard bubbler configurations for liquid precursors. The bubblers were maintained at an ambient temperature of about 22° C. The flow rate through the trimethyl aluminum (TMA) bubbler was 1773 $cm^3$/minute. The flow rate through the water bubbler was 5307 $cm^3$/minute. The total coating time was 120 minutes. The amount of Portland cement added to the reactor was 800 g and the particle size of the Portland cement powder was 20 microns.

Prior to adding to the reactor, fine particles and coarse particles were removed from the Portland cement sample using an AVEKA CCE centrifugal air classifier Model 100. In the first step, a coarse tail totaling about 24% of the initial sample was removed and then in the second step a fines tail of about 25% was removed from the remaining sample. The resulting Portland cement powder had a mean particle size of 20 microns (as determined using a Coulter Counter Multisizer 3 (Beckman Coulter Company).

Encapsulated Material 1 was calculated to have a shell thickness of 46 nm. The calculated weight percentages (wt.-%) were 98.8 wt.-% core material and 1.2 wt.-% shell material.

Example 29. Encapsulated Material 2 (PC Core and AO Shell)

Portland cement (PC) was encapsulated with an aluminum oxide (AO) based material using atmospheric pressure chemical vapor deposition (APCVD). The Portland cement powder was coated by reacting trimethyl aluminum (obtained from Strem Chemicals and dispensed from a stainless steel bubbler) with water vapor in a fluidized bed reactor. The reactor was a glass frit funnel tube (12 cm diameter, 30 cm height). The reactor had an extended inlet tube from below the frit routed parallel to the body of the reactor, and an extended top area above the frit to allow the desired reactor height and fittings for a precursor injector tube and an exhaust outlet. Temperature was controlled at 180° C. using an oil bath. Nitrogen carrier gas was used with standard bubbler configurations for liquid precursors. The bubblers were maintained at an ambient temperature of about 22° C. The flow rate through the trimethyl aluminum (TMA) bubbler was 2670 $cm^3$/minute. The flow rate through the water bubbler was 8032 $cm^3$/minute. The total coating time was 190 minutes. The amount of Portland cement added to the reactor was 1500 g and the particle size of the Portland cement powder was 20 microns.

Prior to adding to the reactor, fine particles and coarse particles were removed from the Portland cement sample using an AVEKA CCE centrifugal air classifier Model 100. In the first step, a coarse tail totaling about 24% of the initial sample was removed and then in the second step a fines tail of about 25% was removed from the remaining sample. The resulting Portland cement powder had a mean particle size of 20 microns (as determined using a Coulter Counter Multisizer 3 (Beckman Coulter Company).

Encapsulated Material 2 was calculated to have a shell thickness of 58 nm. The calculated weight percentages (wt.-%) were 98.5 wt.-% core material and 1.5 wt.-% shell material.

Example 30

The composition of Paste AA-1 is reported in Table 35 (each component reported in wt.-%). Paste AA-1 was prepared in bulk. BisGMA and TEGDMA were combined (1:1 by weight) and stirred until homogeneous. The BisGMA/TEGDMA mixture was combined with BPO and CPQ in a mixing cup. The filled cup was placed in a FlackTek SPEEDMIXER (FlackTek Incorporated, Landrum, SC) and the contents were mixed at 2400 rpm until a homogeneous mixture was achieved. Fumed silica (AEROSIL R972) was added to the cup. The cup was placed in a FlackTeK SPEEDMIXER and the contents were mixed at 2400 rpm until a homogeneous mixture of Paste AA-1 was achieved. The viscosity of Paste AA-1 was 1130±9 cP (at 23° C. and shear rate of 100 $s^{-1}$).

The composition of Paste BB-1 is reported in Table 36 (each component reported in wt.-%). BisGMA and TEGDMA were combined (1:1 by weight) and stirred until homogeneous. The BisGMA/TEGDMA mixture was combined with DMAPE and BHT in a mixing cup. The filled cup was placed in a FlackTek SPEEDMIXER and the contents were mixed at 2400 rpm until a homogeneous mixture was achieved. Fumed silica (AEROSIL R972) was added to the cup. The cup was placed in a FlackTeK SPEEDMIXER and the contents were mixed at 2400 rpm until a homogeneous mixture was achieved. Encapsulated Material 1 was added to the cup. The cup was placed in a FlackTeK SPEEDMIXER and the contents were mixed at 2400 rpm until a homogeneous mixture of Paste BB-1 was achieved. The viscosity of Paste BB-1 was 1450±12 cP (at 23° C. and shear rate of 100 $s^{-1}$).

TABLE 35

Composition of Paste AA-1

| Component | Weight Percent (wt.-%) in the Composition |
|---|---|
| BisGMA/TEGDMA (1:1 by weight) | 93.97 |
| BPO | 0.94 |
| CPQ | 0.09 |
| Fumed Silica (AEROSIL R972) | 5.0 |

TABLE 36

Composition of Paste BB-1

| Component | Weight Percent (wt.-%) in the Composition |
|---|---|
| BisGMA/TEGDMA (1:1 by weight) | 83.66 |
| DMAPE | 1.25 |
| BHT | 0.09 |
| Fumed Silica (AEROSIL R972) | 5.0 |
| Encapsulated Material 1 | 10.0 |

Example 31

The composition of Paste BB-2 is reported in Table 37 (each component reported in wt.-%). BisGMA and TEGDMA were combined (1:1 by weight) and stirred until homogeneous. The BisGMA/TEGDMA mixture was combined with DMAPE and BHT in a mixing cup. The filled cup was placed in a FlackTek SPEEDMIXER and the contents were mixed at 2400 rpm until a homogeneous mixture was achieved. Fumed silica (AEROSIL R972) was added to the cup. The cup was placed in a FlackTeK SPEEDMIXER and the contents were mixed at 2400 rpm until a homogeneous mixture was achieved. Encapsulated Material 2 was added to the cup. The cup was placed in a FlackTeK SPEEDMIXER and the contents were mixed at 2400 rpm until a homogeneous mixture of Paste BB-1 was achieved.

Pastes AA-1 and BB-2 were equilibrated in a chamber at 37° C. and then combined in an approximately 1:1 volume ratio on a mixing pad. The resulting (e.g. sealant) composition hardened after two minutes.

When Pastes AA-1 and BB-2 were combined in a 1:1 volume ratio on a mixing pad at room temperature conditions (about 23° C.) without use of a curing light (dark curing), the sample was not hardened after two minutes.

Alternatively, Pastes AA-1 and BB-2 were combined in a 1:1 volume ratio on a mixing pad at room temperature conditions (about 23° C.) and immediately cured using an Elipar™ DeepCure-S LED curing light (3M Oral Care, Maplewood, MN). The resulting (e.g. sealant) composition hardened after exposure to the light for 10 seconds.

TABLE 37

Composition of Paste BB-2

| Component | Weight Percent (wt.-%) in the Composition |
|---|---|
| BisGMA/TEGDMA (1:1 by weight) | 83.66 |
| DMAPE | 1.25 |
| BHT | 0.09 |
| Fumed Silica (AEROSIL R972) | 5.0 |
| Encapsulated Material 2 | 10.0 |

Example 32

The composition of Paste AA-2 is reported in Table 38 (each component reported in wt.-%). Paste AA-2 was prepared in bulk. BisGMA and TEGDMA were combined (1:1 by weight) and stirred until homogeneous. The BisGMA/TEGDMA mixture was combined with BPO and CPQ in a mixing cup. The filled cup was placed in a FlackTek SPEEDMIXER and the contents were mixed at 2400 rpm until a homogeneous mixture was achieved. Fumed silica (AEROSIL R972) was added to the cup. The cup was placed in a FlackTeK SPEEDMIXER and the contents were mixed at 2400 rpm until a homogeneous mixture of Paste AA-2 was achieved.

The composition of Paste BB-3 is reported in Table 39 (each component reported in wt.-%). BisGMA and TEGDMA were combined (1:1 by weight) and stirred until homogeneous. The BisGMA/TEGDMA mixture was combined with DMAPE and BHT in a mixing cup. The filled cup was placed in a FlackTek SPEEDMIXER and the contents were mixed at 2400 rpm until a homogeneous mixture was achieved. Fumed silica (AEROSIL R972) was added to the cup. The cup was placed in a FlackTeK SPEEDMIXER and the contents were mixed at 2400 rpm until a homogeneous mixture was achieved. Encapsulated Material 2 was added to the cup. The cup was placed in a FlackTeK SPEEDMIXER and the contents were mixed at 2400 rpm until a homogeneous mixture of Paste BB-2 was achieved.

Pastes AA-2 and BB-3 were combined in a 1:1 volume ratio on a mixing pad at room temperature conditions (about 23° C.) without use of a curing light (dark curing). The resulting sealant composition hardened within 1 minute.

Alternatively, Pastes AA-2 and BB-3 were combined in a 1:1 volume ratio on a mixing pad at room temperature conditions (about 23° C.) and immediately cured using an Elipar™ DeepCure-S LED curing light (3M Oral Care). The resulting sealant composition hardened after exposure to the light for 10 seconds.

TABLE 38

Composition of Paste AA-2

| Component | Weight Percent (wt.-%) in the Composition |
|---|---|
| BisGMA/TEGDMA (1:1 by weight) | 89.92 |
| BPO | 2.81 |
| CPQ | 0.09 |
| Fumed Silica (AEROSIL R972) | 7.18 |

TABLE 39

Composition of Paste BB-3

| Component | Weight Percent (wt.-%) in the Composition |
|---|---|
| BisGMA/TEGDMA (1:1 by weight) | 81.22 |
| DMAPE | 4.13 |
| BHT | 0.09 |
| Fumed Silica (AEROSIL R972) | 4.85 |
| Encapsulated Material 2 | 9.71 |

Example 33

A two chamber syringe device with a dispensing nozzle and static mixer as described in FIGS. 1-4 was used. Dimensions of the syringe device were as follows: cartridge length=73.8 mm, cartridge exterior diameter=8.4 mm, volume of each chamber=1 mL, total volume of the dispensing nozzle=0.03 mL, diameter of dispensing nozzle outlet orifice=0.85 mm, nozzle tip length=9 mm, interior included angle of the nozzle tip=120°. A static mixer as described for FIG. 4 was inserted in the cannula portion of the dispensing nozzle. The overall length of the series of mixing paddles was 15 mm. The two chambers each had a substantially D-shaped cross section and the D-shapes were oriented in a mirrored fashion relative to each other.

One chamber of the syringe was partially filled (2/3 by volume) with Paste AA-2. The second chamber was partially filled (2/3 by volume) with Paste BB-3. Upon depressing the plunger, the filled syringe metered a 1:1 volume ratio of Paste AA-2 and Paste BB-3 into the dispensing nozzle. A typodont model of the upper arch of teeth in the human mouth was used with each tooth having deep fissures. The syringe device was used to apply a thin coating of the sealant composition onto the surfaces of 10 teeth in the model. It was observed that upon application the sealant composition penetrated into the fissures. The total time to apply the sealant composition to the ten teeth was about 45 seconds. The sealant composition hardened about 45 seconds after application to a tooth.

Example 34

A two chamber syringe device as described in Example 6 was used. One chamber of the syringe was partially filled (2/3 by volume) with Paste AA-1. The second chamber was partially filled (2/3 by volume) with Paste BB-1. Upon depressing the plunger, the filled syringe metered a 1:1 volume ratio of Paste AA-1 and Paste BB-1 into the dispensing nozzle. The syringe device was used to fill a Teflon disk mold (3.1 mm diameter and 1.3 mm height) with the paste. The paste was then cured using an ELIPAR S10 curing light (3M Oral Care) for 20 seconds on each side of the mold. The resulting molded disk was immediately removed from the mold and placed in a 2 mL plastic centrifuge tube that contained 0.5 mL of buffered solution, mixed as 15 g of deionized water and 10 g of a pH 4 buffer solution (Buffer BDH5018, VWR International). The disk was completely submerged in in the buffered solution. The tube was capped and stored at room temperature.

The pH of the buffered solution was measured using an ORION PERPHECT ROSS pH Micro Electrode (catalog number 8220BNWP, Thermo Fisher Scientific Company, Waltham, PA). The sample was gently shaken before each measurement. The pH measurements were taken immediately after submersion of the disk in the buffer solution ("0 hr" in Table), and at 15 hours and 39 hours after submersion.

A comparative example molded disk was prepared and tested according to the described procedure with the only change being that Paste BB-1 was replaced with Paste BB-C1 that did not contain any Encapsulated Material 1 (Table 40). The pH profiles are reported in Table 41.

TABLE 40

Composition of Paste BB-C1

| Component | Weight Percent (wt.-%) in the Composition |
|---|---|
| BisGMA/TEGDMA (1:1 by weight) | 92.52 |
| DMAPE | 1.39 |
| BHT | 0.09 |
| Fumed Silica (AEROSIL R972) | 6.0 |
| Encapsulated Material 1 | 0.0 |

Example 35 (Comparative)

The same procedure and test method as described in Example 6 was followed with the exception that the Encapsulated Material 1 in Paste BB-1 was replaced with an equivalent amount of non-encapsulated Portland cement (wt.-%=10%). to the described procedure with the only change being that Paste BB-1 did not contain any Encapsulated Material 2. The pH profiles are reported in Table 6.

TABLE 41 pH Measurements of PBS Solutions in Contact with Molded Disks Prepared from Examples 34 and 35

| | pH of PBS Solution | | |
|---|---|---|---|
| | 0 hr | 15 hr | 39 hr |
| Example 34 Disk (prepared with Paste BB-1 containing Encapsulated Material 1) | 4.123 | 4.315 | 4.377 |
| Example 35 Disk (Comparative Example prepared with a paste containing Non-Encapsulated Portland Cement) | 4.096 | 4.374 | 4.332 |
| Comparative Example Disk (prepared with Paste BB-C1) | 4.124 | 4.127 | 4.136 |

Example 36

The composition of Paste BB-4 is reported in Table 42 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-4 is achieved.

Pastes AA-1 and BB-4 are combined in an approximately 1:1 volume ratio on a mixing pad to provide the resulting sealant composition.

Example 37

The composition of Paste BB-5 is reported in Table 42 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-5 is achieved.

Pastes AA-1 and BB-5 are combined in an approximately 1:1 volume ratio on a mixing pad to provide the resulting sealant composition.

Example 38

The composition of Paste BB-6 is reported in Table 42 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-6 is achieved.

Pastes AA-1 and BB-6 are combined in an approximately 1:1 volume ratio on a mixing pad to provide the resulting sealant composition.

Example 39

The composition of Paste BB-7 is reported in Table 42 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-7 is achieved.

Pastes AA-1 and BB-7 are combined in an approximately 1:1 volume ratio on a mixing pad to provide the resulting sealant composition.

Example 40

The composition of Paste BB-8 is reported in Table 42 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-8 is achieved.

Pastes AA-1 and BB-8 are combined in an approximately 1:1 volume ratio on a mixing pad to provide the resulting sealant composition.

Example 41

The composition of Paste BB-9 is reported in Table 42 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-9 is achieved.

Pastes AA-1 and BB-9 are combined in an approximately 1:1 volume ratio on a mixing pad to provide the resulting sealant composition.

TABLE 42

Compositions of Pastes BB-4, BB-5, BB-6, BB-7, BB-8, and BB-9

| Component | Weight Percent (wt.-%) in the Composition (Pastes BB-4 to BB-9) | | | | | |
|---|---|---|---|---|---|---|
| | BB-4 | BB-5 | BB-6 | BB-7 | BB-8 | BB-9 |
| BisGMA/ TEGDMA (1:1 by weight) | 86.55 | 81.74 | 76.93 | 72.12 | 67.31 | 62.51 |
| DMAPE | 1.30 | 1.23 | 1.15 | 1.08 | 1.01 | 0.94 |
| BHT | 0.09 | 0.08 | 0.08 | 0.07 | 0.07 | 0.06 |
| Fumed Silica (AEROSIL R972) | 2.06 | 1.95 | 1.84 | 1.73 | 1.61 | 1.49 |
| Encapsulated Material 1 | 10.0 | 15.0 | 20.0 | 25.0 | 30.0 | 35.0 |

Example 42

Resin A can be prepared by mixing the components in Table 43 at 45° C. until all of the components are uniformly mixed. Resin A is mixed with ST Nanozirconia Nanoparticles, S/T 20 nm Silica Nanoparticles, ST Silica/Zirconia Nanoclusters, and Encapsulated Material 1 in the amounts (wt-% o) shown in Table 44 to form homogeneous dental compositions with varying amounts of Encapsulated Material 1 (16.8-67.2 wt.-%). The dental compositions are identified in Table 44 as Ex. 42-1, Ex. 42-2, Ex. 42-3, and Ex. 42-4.

TABLE 43

Composition of Resin A

| Component | Weight Percent (wt.-%) in the Composition |
|---|---|
| BisGMA | 24.575 |
| TEGDMA | 1.182 |
| UDMA | 34.401 |
| BisEMA-6 | 34.401 |
| PEG600 DM | 3.736 |
| CPQ | 0.220 |
| DPIHFP | 0.350 |
| IRGACURE 819 | 0.050 |
| ENMAP | 0.810 |
| BHT | 0.150 |
| BZT | 0.125 |

TABLE 44

Dental Compositions with Varying Amounts of Encapsulated Material 1

| Component | Weight Percent (wt.-%) in the Dental Compositions of Example 42 | | | |
|---|---|---|---|---|
| | Ex. 42-1 | Ex. 42-2 | Ex. 42-3 | Ex.42-4 |
| Resin A | 21.0 | 21.0 | 21.0 | 21.0 |
| S\T Nanozirconia Nanoparticles | 4.1 | 4.1 | 4.1 | 4.1 |
| S/T 20 nm Silica Nanoparticles | 7.7 | 7.7 | 7.7 | 7.7 |
| ST Silica/Zirconia Nanoclusters | 50.4 | 33.6 | 16.8 | 0 |
| Encapsulated Material 1 | 16.8 | 33.6 | 50.4 | 67.2 |

What is claimed is:

1. A two part hardenable dental composition comprising:

a first part comprising:

a polymerizable liquid;

an acid-reactive filler; and an encapsulated material comprising:

a core comprising:

a basic material or a basic compound characterized by a pKa of 8-14, and a source of calcium ions derived from the basic material or the basic compound, a calcium compound other than the basic material or the basic compound, or a combination thereof, wherein the core is characterized by an average particle size of at least 5 μm; and an inorganic shell comprising a metal oxide, wherein the inorganic shell surrounds the core; and a second part comprising, an acidic polymer, wherein the first part is characterized by a first viscosity of less than 25,000 cps as determined with a Brookfield viscometer and type-A T-bar spindle at 23° C. and a shear rate of 100 $s^{-1}$, or wherein the first part is characterized by a first viscosity of greater than 40,000 cps as determined with a Brookfield viscometer and type-A T-bar spindle at 23° C. and a shear rate of 100 $s^{-1}$, wherein the second part is characterized by a second viscosity, wherein the first viscosity and the second viscosity differ by an amount no greater than 85, 80, 75, 70, 65, 60, 55, 50, 45, 40, 35, 30, 25, 20, 15, or 10% as determined with a Brookfield viscometer and type-A T-bar spindle at 23° C. and a shear rate of 100 $s^{-1}$.

2. The two part hardenable dental composition of claim 1, further comprising:

a redox curing system.

3. The two part hardenable dental composition of claim 1, comprising:

the first part further comprising a reducing agent;

the second part further comprising an oxidizing agent selected from a peroxide compound, a persulfate compound, a perborate compound, and a perchlorate compound.

4. The two part hardenable composition of claim 1, wherein the inorganic shell is degradable by the second part.

5. The two part hardenable dental composition of the claim 1, wherein the inorganic shell is a continuous film having an average thickness less than 500 nm.

6. The two part hardenable dental composition of claim 1, wherein the core further comprising a dental filler comprising one or more neutral metal oxide.

7. The two part hardenable dental composition of claim 6, the dental filler being nanoscopic and comprising zirconia, silica, or a combination thereof.

8. The two part hardenable dental composition of claim 1, wherein contacting the first part and the second part provide for a delayed increase in basicity upon release of the core from the encapsulated material.

9. A dispensing device comprising the two part hardenable dental composition of claim 1.

10. The dispensing device of claim 9, wherein the device comprises:

a cartridge comprising two chambers, a nozzle comprising an outlet at one end of the cartridge; and a plunger at the opposing end of the cartridge for dispensing the two part hardenable composition from the cartridge.

11. The dispensing device of claim 10, further comprising a static mixer, and the plunger comprises two plunger rods that are connected.

12. The dispensing device of claim 11, wherein the outlet has a diameter no greater than 1.5 or 1 mm.

13. The two-part hardenable dental composition of claim 1, the core comprising tricalcium silicate, dicalcium silicate, calcium silicate, tricalcium aluminate, tetracalcium aluminoferrite, a bioactive glass, or a combination thereof.

14. The two-part hardenable dental composition of claim 1, the core comprising an oxide or hydroxide of Na, K, Ca, Sr, or Ba.

15. The two-part hardenable dental composition of claim 1, the basic material comprising Portland cement.

16. The two-part hardenable dental composition of claim 1, the metal oxide selected from titanium oxide, aluminum oxide, and a combination thereof.

17. The two-part hardenable dental composition of claim 1, the first part being a paste and the second part being a paste.

18. A hardenable dental composition comprising:

a liquid material, and an encapsulated material comprising:

a core comprising:

a basic material or a basic compound characterized by a pKa of 8-14, and a source of calcium ions derived from the basic material or the basic compound, a calcium compound other than the basic material or the basic compound, or a combination thereof, wherein the core is characterized by an average particle size of at least 5 μm; and an inorganic shell comprising a metal oxide, wherein the inorganic shell surrounds the core, wherein the hardenable dental composition is characterized by a viscosity of less than 25,000 cps as determined with a Brookfield viscometer and type-A T-bar spindle at 23° C. and shear rate of 100 $s^{-1}$, or is characterized by a viscosity greater than 40,000 cps as determined with a Brookfield viscometer and type-A T-bar spindle at 23° C. and shear rate of 100 $s^{-1}$.

19. The hardenable dental composition of claim 18, wherein the liquid material comprises a polymerizable material.

20. A dispensing device comprising the one-at-hardenable dental composition of claim 18.

* * * * *